(12) United States Patent
Goldman et al.

(10) Patent No.: US 12,303,549 B2
(45) Date of Patent: May 20, 2025

(54) METHODS OF TREATING OR INHIBITING ONSET OF HUNTINGTON'S DISEASE

(71) Applicants: University of Rochester, Rochester, NY (US); University of Copenhagen, Copenhagen (DK)

(72) Inventors: Steven A. Goldman, Webster, NY (US); Mikhail Osipovitch, Frederiksberg (DK)

(73) Assignees: University of Rochester, Rochester, NY (US); University of Copenhagen, Copenhagen K (DK)

( * ) Notice: Subject to any disclaimer, the term of this patent is extended or adjusted under 35 U.S.C. 154(b) by 1068 days.

(21) Appl. No.: 17/254,734

(22) PCT Filed: Jun. 19, 2019

(86) PCT No.: PCT/US2019/037987
§ 371 (c)(1),
(2) Date: Dec. 21, 2020

(87) PCT Pub. No.: WO2019/246262
PCT Pub. Date: Dec. 26, 2019

(65) Prior Publication Data
US 2022/0062378 A1   Mar. 3, 2022

Related U.S. Application Data

(60) Provisional application No. 62/688,174, filed on Jun. 21, 2018.

(51) Int. Cl.
*A61K 38/17* (2006.01)
*A61K 35/30* (2015.01)
*A61P 25/28* (2006.01)

(52) U.S. Cl.
CPC .......... *A61K 38/1709* (2013.01); *A61K 35/30* (2013.01); *A61P 25/28* (2018.01)

(58) Field of Classification Search
None
See application file for complete search history.

(56) References Cited

U.S. PATENT DOCUMENTS

| | | |
|---|---|---|
| 7,524,491 B2 | 4/2009 | Goldman et al. |
| 8,206,699 B2 | 6/2012 | Goldman et al. |
| 8,263,402 B1 | 9/2012 | Goldman et al. |
| 9,371,513 B2 | 6/2016 | Goldman et al. |
| 9,709,553 B2 | 7/2017 | Goldman et al. |
| 9,724,432 B2 | 8/2017 | Goldman |
| 10,190,095 B2 | 1/2019 | Goldman et al. |
| 10,279,051 B2 | 5/2019 | Goldman |
| 10,450,546 B2 | 10/2019 | Goldman et al. |
| 10,626,369 B2 | 4/2020 | Goldman et al. |
| 10,779,519 B2 | 9/2020 | Goldman et al. |
| 11,344,582 B2 | 5/2022 | Goldman et al. |
| 11,596,700 B2 | 3/2023 | Goldman |
| 11,690,876 B2 | 7/2023 | Goldman et al. |
| 2004/0014210 A1 | 1/2004 | Jessell |
| 2015/0139983 A1 | 5/2015 | Karni et al. |
| 2017/0182097 A1 | 6/2017 | Goldman |
| 2020/0048604 A1 | 2/2020 | Goldman et al. |
| 2020/0048605 A1 | 2/2020 | Goldman et al. |
| 2020/0197445 A1 | 6/2020 | Goldman et al. |
| 2021/0260002 A1 | 8/2021 | Goldman et al. |
| 2022/0025379 A1 | 1/2022 | Goldman et al. |
| 2022/0267737 A1 | 8/2022 | Goldman et al. |
| 2022/0273728 A1 | 9/2022 | Goldman et al. |
| 2022/0290099 A1 | 9/2022 | Goldman et al. |
| 2023/0057355 A1 | 2/2023 | Goldman et al. |
| 2023/0173110 A1 | 6/2023 | Goldman |
| 2023/0243811 A1 | 8/2023 | Goldman et al. |

FOREIGN PATENT DOCUMENTS

| WO | 2017027280 A1 | 2/2017 |
|---|---|---|
| WO | 2017/060884 A1 | 4/2017 |

OTHER PUBLICATIONS

Zhao et al. Nature Communications | 7:10883 | DOI: 10. 1038/ncomms10883 | Published Mar. 9, 2016.*
Chew Li-Jin et al: "Finding degrees of separation: Experimental approaches for astroglial and oligodendroglial cell isolation and genetic targeting", Journal of Neuroscience Methods, Elsevier Science Publisher B. V., Amsterdam, NL, vol. 236, Aug. 26, 2014 (Aug. 26, 2014), pp. 125-147.
Zhang Ningzhe et al: "iPSC-based drug screening for Huntington's disease", Brain Research, Elsevier, Amsterdam, NL, vol. 1638, Sep. 30, 2015 (Sep. 30, 2015), pp. 42-56.
Santos Ak et al: "Decoding cell signalling and regulation of oligodendrocyte differentiation", Seminars in Cell and Developmental Biology, Academic Press, GB, vol. 95, May 23, 2018 (May 23, 2018), pp. 54-73.
International Search Report and Written Opinion for PCT/US2019/037987, dated Jan. 20, 2020.
Khakh et al., "Unravelling and Exploiting Astrocyte Dysfunction in Huntington's Disease," Trends in Neurosciences 40(7):422-437 (2017).
Notice of Reasons for Rejection in Japanese Patent Application No. 2020-571689 (dated Jul. 13, 2023).
Second Office Action for China Patent Application No. 201980054882.0 (Jun. 26, 2023).
Office Action in Canadian Patent Application No. 3,103,675 (dated Jul. 20, 2023).

(Continued)

*Primary Examiner* — Blaine Lankford
(74) *Attorney, Agent, or Firm* — Fox Rothschild LLP

(57) ABSTRACT

The disclosure herein relates generally to a method of treating or inhibiting onset of Huntington's disease. This method involves selecting a subject having or at risk of having Huntington's disease and administering to the subject one or modulators of one or more genes as described herein, or proteins encoded therefrom, under conditions effective to treat or inhibit onset of Huntington's disease in the subject.

19 Claims, 41 Drawing Sheets
Specification includes a Sequence Listing.

(56) References Cited

OTHER PUBLICATIONS

International Preliminary Report on Patentability and Written Opinion for corresponding International Application No. PCT/US2019/037987, dated Dec. 30, 2020.
U.S. Appl. No. 18/135,543, filed Apr. 17, 2023, first named inventor Steven A. Goldman.
Translation of the First Office Action for China Patent Application No. 201980054882.0 (Sep. 5, 2022).
Re'guilier et al., "Early and Reversible Neuropathology Induced by Tetracycline-Regulated Lentiviral Overexpression of Mutant Huntingtin in Rat Striatum," Human Molecular Genetics 12(21):2827-2836 (2003).
Wegener et al., "Increased Sox10 Levels Directly Convert Satellite Glia into Oligodendrocyte-Like Cells In Vivo," GLIA 63:E194 (2015).
Huang et al., "Mutant Huntingtin Downregulates Myelin Regulatory Factor-Mediated Myelin Gene Expression and Affects Mature Oligodendrocytes," Neuron 85:1212-1226 (2015).
Gaudioso et al., "Glial Cell-Dysfunction and Therapeutic Potential of Trehalose in an Early Huntington's Disease Cellular Model," GLIA 63:E165 (2015).
U.S. Appl. No. 17/430,768, filed Aug. 13, 2021, first named inventor Steven A. Goldman.
U.S. Appl. No. 17/920,140, filed Oct. 20, 2022, first named inventor Steven A. Goldman.

\* cited by examiner

| Module | Term ID | Title | P Value | Total in Term | Observed | Expected | Fold Enrichment | Associated Genes |
|---|---|---|---|---|---|---|---|---|
| WT | GO:0045685 | regulation of glial cell differentiation | >1.00E-10 | 59 | 10 | 1.32 | 7.58 | BMP2, LINGO1, MAG, NKX2-2, NR2E1, NTRK3, OLIG2, SERPINE2, SIRT2, TCF7L2 |
| | GO:0042552 | myelination | >1.00E-10 | 100 | 15 | 2.24 | 6.71 | FA2H, GAL3ST1, MAG, MBP, MYRF, NFASC, OLIG2, OMG, PLLP, POU3F2, SIRT2, SLC8A3, TCF7L2, TF, UGT8 |
| | GO:0048709 | oligodendrocyte differentiation | >1.00E-10 | 81 | 12 | 1.81 | 6.63 | FA2H, GLI3, LINGO1, MYRF, NKX2-2, OLIG1, OLIG2, OMG, SIRT2, SLC8A3, SOX10, TCF7L2 |
| | GO:0014013 | regulation of gliogenesis | >1.00E-10 | 99 | 14 | 2.21 | 6.32 | BMP2, LINGO1, MAG, MYC, NKX2-2, NR2E1, NTRK3, OLIG2, SERPINE2, SIRT2, SOX10, TCF7L2, TF, ZCCHC24 |
| | GO:0007272 | ensheathment of neurons | >1.00E-10 | 113 | 15 | 2.53 | 5.94 | FA2H, GAL3ST1, MAG, MBP, MYRF, NFASC, OLIG2, OMG, PLLP, POU3F2, SIRT2, SLC8A3, TCF7L2, TF, UGT8 |
| | GO:0007411 | axon guidance | >1.00E-10 | 228 | 18 | 5.10 | 3.53 | ALCAM, BCL11B, DSCAM, FOXD1, GAS1, GLI3, HOXA1, HOXA2, MNX1, NFASC, PLXNC1, PRKCQ, PTPRO, ROBO2, SEMA6B, UNC5A, VAX1, WNT7B |
| | GO:0097485 | neuron projection guidance | >1.00E-10 | 231 | 18 | 5.16 | 3.49 | ALCAM, BCL11B, DSCAM, FOXD1, GAS1, GLI3, HOXA1, HOXA2, MNX1, NFASC, PLXNC1, PRKCQ, PTPRO, ROBO2, SEMA6B, UNC5A, VAX1, WNT7B |

*FIG. 3B*

| | | | | | |
|---|---|---|---|---|---|
| M2 | | | | | |
| GO:0007409 | axonogenesis | >1.00E-10 | 423 | 32 | 9.46 | 3.38 | ADGRB1, ALCAM, BCL11B, CACNA1A, DSCAM, FOXD1, GAS1, GLI3, HOXA1, HOXA2, LINGO1, LRRC4C, MAG, MBP, MNX1, NFASC, NR2E1, NTNG1, NTRK3, OMG, PLXNC1, POU3F2, PRKCQ, PTPRO, ROBO2, SEMA6B, SLITRK2, SLITRK3, SNAP91, UNC5A, VAX1, WNT7B |
| GO:0061564 | axon development | >1.00E-10 | 469 | 34 | 10.49 | 3.24 | ADGRB1, ALCAM, BCL11B, CACNA1A, DSCAM, FOXD1, GAS1, GLI3, HOXA1, HOXA2, LINGO1, LRRC4C, MAG, MBP, MNX1, NEFM, NFASC, NR2E1, NTNG1, NTRK3, OMG, PLXNC1, POU3F2, PRKCQ, PTPRO, ROBO2, RTN4RL2, SEMA6B, SLITRK2, SLITRK3, SNAP91, UNC5A, VAX1, WNT7B |
| GO:0048858 | cell projection morphogenesis | >1.00E-10 | 608 | 41 | 13.59 | 3.02 | ADGRB1, ALCAM, BCL11B, CACNA1A, CAMK2A, DSCAM, EHD3, FOXD1, GAS1, GLI3, HOXA1, HOXA2, KANK1, LINGO1, LRRC4C, MAG, MBP, MNX1, NEDD4L, NEURL1, NFASC, NR2E1, NTNG1, NTRK3, OMG, PODH15, PLXNC1, POU3F2, PRKCQ, PTPRO, ROBO2, SEMA6B, SGK1, SLITRK2, SLITRK3, SNAP91, SNX10, UGT8, UNC5A, VAX1, WNT7B |
| GO:0050803 | regulation of synapse structure or activity | >1.00E-10 | 132 | 21 | 2.95 | 7.12 | ADGRB1, ADGRL3, BCAN, CALB1, CAMK2A, FGF14, LRRTM1, NCDN, NETO1, NEURL1, NR2E1, NTRK3, PPFIA3, ROBO2, SERPINE2, SHISA7, SIX4, SLC8A3, SLITRK2, SLITRK3, SYNDIG1 |

FIG. 3B (cont.)

| | GO ID | Term | p-value | | | Genes |
|---|---|---|---|---|---|---|
| | GO:0099536 | synaptic signaling | >1.00E-10 | 604 | 38 | 13.50 | 2.81 | BCAN, CACNA1A, CACNA1G, CALB1, CAMK2A, CHRNA4, FGF12, FGF14, GRIA2, GRIA4, GRID2, GRIK4, KCND2, LRRTM1, MBP, MPZ, NCDN, NETO1, NEURL1, NOVA1, MR2E1, P2RX7, PDE7B, PLCL1, PPFIA3, RAPGEF4, RGS3, RIT2, S1PR2, SERPINE2, SHISA7, SLC18A1, SLC1A1, SLC1A2, SLC8A3, SNAP91, SNPH, SYT6 |
| | GO:0045202 | synapse | >1.00E-10 | 847 | 40 | 18.94 | 2.11 | ADGRB1, BCAN, BCAS1, CACNA1A, CALB1, CAMK2A, CHRNA4, CTTNBP2, DSCAM, GRIA2, GRIA4, GRID1, GRID2, GRIK4, HCN2, KCND2, LGI3, LRRC4C, LRRTM1, NETO1, NEURL1, NTM, P2RX7, PCDH15, PDE4B, PPFIA3, PRIMA1, PRKCQ, PTPRO, RAPGEF4, SERPINE2, SHISA7, SLC17A8, SLC18A1, SLC1A2, SLC8A3, SNAP91, SNPH, SYNDIG1, SYT6 |
| M3 | GO:0015672 | monovalent inorganic cation transport | 1.04E-06 | 586 | 30 | 13.10 | 2.29 | ABCC9, ASIC4, CACNA1A, CHRNA4, CNGB1, CNTN1, DPP10, DPP6, FGF12, FGF14, HCN2, KCND2, KCNJ9, KCNQ1, KCNS3, NALCN, NEDD4L, NKAIN4, P2RX7, PTGER3, SERPINE2, SGK1, SLC10A4, SLC17A8, SLC18A1, SLC22A3, SLC5A9, SLC8A3, SLC9A7 |
| | GO:0043005 | neuron projection | 4.17E-06 | 1251 | 44 | 27.97 | 1.57 | ADGRL3, ALCAM, BCAN, BCL11B, CACNA1A, CACNA1G, CALB1, CAMK2A, CHRNA4, CTTNBP2, DSCAM, GRIA2, GRIA4, GRID2, GRIK4, HCN2, KCND2, LGI3, LRRTM1, MAG, MBP, MYC, NCAM2, NCDN, NEFM, NEURL1, NFASC, NTM, PDE4B, PIK3R1, PTGER3, PTPRO, RAPGEF4, RGS3, ROBO2, SGK1, SIRT2, SLC17A8, SLC1A2, SLC8A3, SNAP91, SNPH, SYNDIG1, UNC5A |

FIG. 3B (cont.)

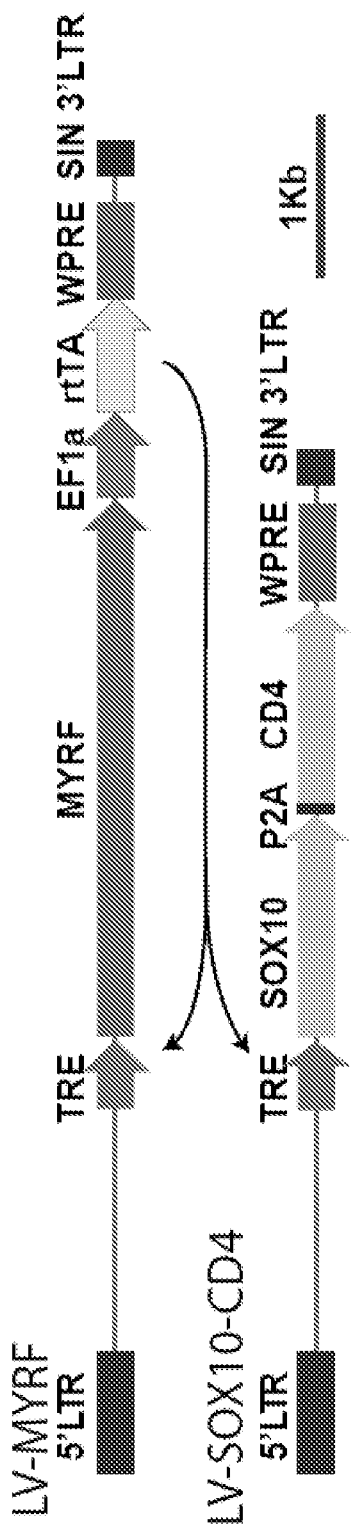
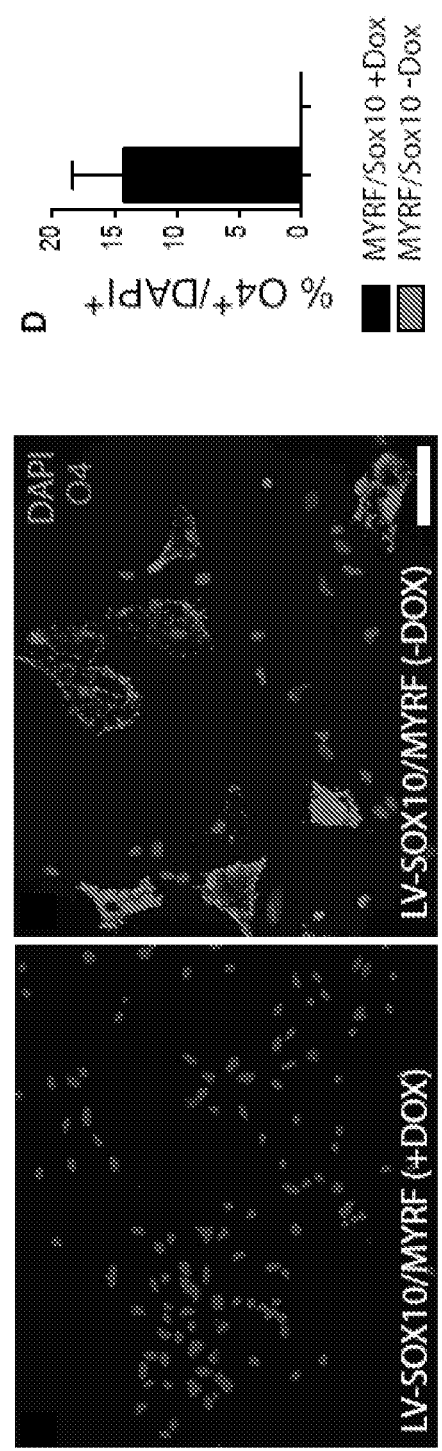
FIG. 11A
FIG. 11B
FIG. 11C
FIG. 11D

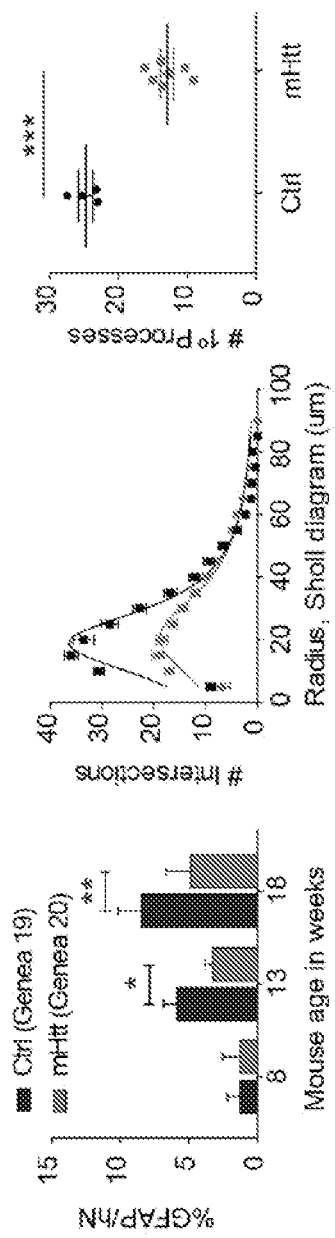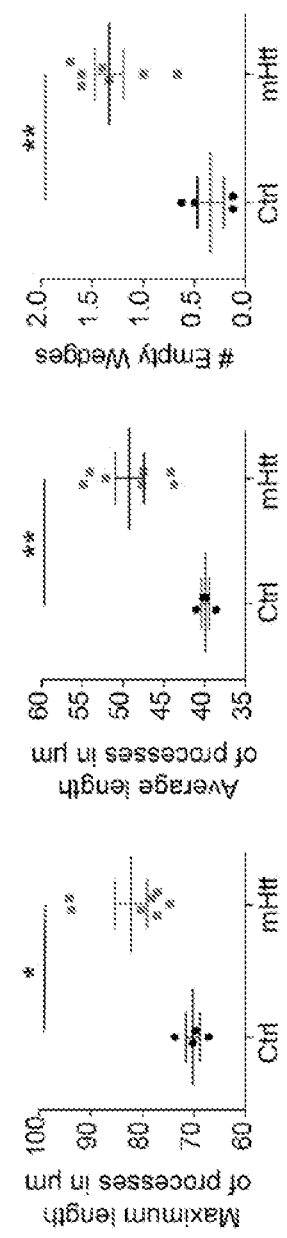
FIG. 12I  FIG. 12J  FIG. 12K
FIG. 12L  FIG. 12M  FIG. 12N

METHODS OF TREATING OR INHIBITING ONSET OF HUNTINGTON'S DISEASE

This application claims benefit of U.S. Provisional Patent Application Ser. No. 62/688,174, filed Jun. 21, 2018, which is hereby incorporated by reference in its entirety.

FIELD

The present application relates to methods of treating or inhibiting onset of Huntington's disease.

BACKGROUND

Huntington's disease (HD) is a fatal, autosomal-dominant neurodegenerative disorder characterized by progressive behavioral, cognitive, and motor dysfunction. HD is caused by a CAG trinucleotide repeat in the first exon of the huntingtin (HTT) gene, encoding a polyglutamine expansion. Its age of onset and severity are proportional to the length of this repeat expansion, with CAG lengths over 35 invariably leading to clinical disease. This is associated with the intracellular accumulation and aggregation of mutant HTT (mHTT), which leads to neuronal loss. While HD pathology is most reflected by the progressive loss of striatal medium spiny neurons (MSNs), and consequent striatal atrophy, MRI studies have revealed that HD is also characterized by the early appearance of demyelination and white matter loss, which can appear before symptoms arise (Tabrizi et al., "Potential Endpoints for Clinical Trials in Premanifest and Early Huntington's Disease in the TRACK-HD Study: Analysis of 24 Month Observational Data," *The Lancet Neurology* 11:42-53 (2012)). Similarly, studies in mouse models of HD have revealed early dysmyelination (Teo et al., "Structural and Molecular Myelination Deficits Occur Prior to Neuronal loss in the YAC128 and BACHD Models of Huntington Disease," *Human Molecular Genetics* 25:2621-2632 (2016)), attended by a deficit in the critical myelinogenic gene MYRF (Huang et al., "Mutant Huntingtin Downregulates Myelin Regulatory Factor-Mediated Myelin Gene Expression and Affects Mature Oligodendrocytes," *Neuron* 85:1212-1226 (2015); Jin et al., "Early White Matter Abnormalities, Progressive Brain Pathology and Motor Deficits in a Novel Knock-In Mouse Model of Huntington's Disease," *Human Molecular Genetics* 24:2508-2527 (2015)). Together, these observations suggest that HD pathology is associated with white matter loss, which may in turn reflect the dysfunction of myelin-producing oligodendrocytes.

Yet despite these data implicating white matter abnormalities and dysmyelination in HD, and parallel studies indicating that glial replacement may ameliorate symptoms in HD transgenic mice (Benraiss et al., "Human Glia can Both Induce and Rescue Aspects of Phenotype in Huntington Disease," *Nature Communications* 7:11758 (2016)), neither the cellular nor molecular underpinnings of glial pathology in human HD have been well-explored.

The present disclosure is directed to overcoming these and other deficiencies in the art.

SUMMARY

A first aspect of the present disclosure relates to a method of treating or inhibiting onset of Huntington's disease. This method involves selecting a subject having or at risk of having Huntington's disease and administering to the selected subject one or more modulators of a glial cell differentiation regulation gene selected from the group consisting of BMP2, LINGO1, MAG, NKX2-2, NR2E1, NTRK3, OLIG2, SERPINE2, SIRT2, and TCF7L2, or a protein encoded therefrom under conditions effective to treat or inhibit onset of Huntington's disease in the subject.

Another aspect of the present disclosure relates to a method of treating or inhibiting onset of Huntington's disease. This method involves selecting a subject having or at risk of having Huntington's disease and administering to the selected subject one or more modulators of a myelination-associated gene selected from the group consisting of FA2H, GAL3ST1, MAG, MBP, MYRF, NFASC, OLIG2, OMG, PLLP, POU3F2, SIRT2, SLC8A3, TCF7L2, TF, and UGT8, or a protein encoded therefrom under conditions effective to treat or inhibit onset of Huntington's disease in the subject.

Another aspect of the present disclosure relates to a method of treating or inhibiting onset of Huntington's disease. This method involves selecting a subject having or at risk of having Huntington's disease and administering to the selected subject one or more modulators of an oligodendrocyte differentiation gene selected from the group consisting of FA2H, GLI3, LINGO1, MYRF, NKX2-2, OLIG1, OLIG2, OMG, SIRT2, SLC8A3, SOX10, and TCF7L2, or a protein encoded therefrom under conditions effective to treat or inhibit onset of Huntington's disease in the subject.

Another aspect of the present disclosure relates to a method of treating or inhibiting onset of Huntington's disease. This method involves selecting a subject having or at risk of having Huntington's disease and administering to the selected subject one or more modulators of a gliogenesis regulation gene selected from the group consisting of BMP2, LINGO1, MAG, MYC, NKX2-2, NR2E1, NTRK3, OLIG2, SERPINE2, SIRT2, SOX10, TCF7L2, TF, and ZCCHC24, or a protein encoded therefrom under conditions effective to treat or inhibit onset of Huntington's disease in the subject.

Another aspect of the present disclosure relates to a method of treating or inhibiting onset of Huntington's disease. This method involves selecting a subject having or at risk of having Huntington's disease and administering to the selected subject one or more modulators of a neuron ensheathment gene selected from the group consisting of FA2H, GAL3ST1, MAG, MBP, MYRF, NFASC, OLIG2, OMG, PLLP, POU3F2, SIRT2, SLC8A3, TCF7L2, TF, and UGT8, or a protein encoded therefrom under conditions effective to treat or inhibit onset of Huntington's disease in the subject.

Another aspect of the present disclosure relates to a method of treating or inhibiting onset of Huntington's disease. This method involves selecting a subject having or at risk of having Huntington's disease and administering to the selected subject one or more modulators of an axon guidance gene selected from the group consisting of ALCAM, BCL11B, DSCAM, FOXD1, GAS1, GLI3, HOXA1, HOXA2, MNX1, NFASC, PLXNC1, PRKCQ, PTPRO, ROBO2, SEMA6B, UNC5A, VAX1, and WNT7B, or a protein encoded therefrom under conditions effective to treat or inhibit onset of Huntington's disease in the subject.

Another aspect of the present disclosure relates to a method of treating or inhibiting onset of Huntington's disease. This method involves selecting a subject having or at risk of having Huntington's disease and administering to the selected subject one or more modulators of a neuron projection guidance gene selected from the group consisting of ALCAM, BCL11B, DSCAM, FOXD1, GAS1, GLI3, HOXA1, HOXA2, MNX1, NFASC, PLXNC1, PRKCQ, PTPRO, ROBO2, SEMA6B, UNC5A, VAX1, and WNT7B, or a protein encoded therefrom under conditions effective to treat or inhibit onset of Huntington's disease in the subject.

Another aspect of the present disclosure relates to a method of treating or inhibiting onset of Huntington's disease. This method involves selecting a subject having or at risk of having Huntington's disease and administering to the selected subject one or more modulators of an axonogenesis gene selected from the group consisting of ADGRB1, ALCAM, BCL11B, CACNA1A, DSCAM, FOXD1, GAS1, GLI3, HOXA1, HOXA2, LINGO1, LRRC4C, MAG, MBP, MNX1, NFASC, NR2E1, NTNG1, NTRK3, OMG, PLXNC1, POU3F2, PRKCQ, PTPRO, ROBO2, SEMA6B, SLITRK2, SLITRK3, SNAP91, UNC5A, VAX1, and WNT7B, or a protein encoded therefrom under conditions effective to treat or inhibit onset of Huntington's disease in the subject.

Another aspect of the present disclosure relates to a method of treating or inhibiting onset of Huntington's disease. This method involves selecting a subject having or at risk of having Huntington's disease and administering to the selected subject one or more modulators of an axon development gene selected from the group consisting of ADGRB1, ALCAM, BCL11B, CACNA1A, DSCAM, FOXD1, GAS1, GLI3, HOXA1, HOXA2, LINGO1, LRRC4C, MAG, MBP, MNX1, NEFM, NFASC, NR2E1, NTNG1, NTRK3, OMG, PLXNC1, POU3F2, PRKCQ, PTPRO, ROBO2, RTN4RL2, SEMA6B, SLITRK2, SLITRK3, SNAP91, UNC5A, VAX1, and WNT7B, or a protein encoded therefrom under conditions effective to treat or inhibit onset of Huntington's disease in the subject.

Another aspect of the present disclosure relates to a method of treating or inhibiting onset of Huntington's disease. This method involves selecting a subject having or at risk of having Huntington's disease and administering to the selected subject one or more modulators of a cell projection morphogenesis gene selected from the group consisting of ADGRB1, ALCAM, BCL11B, CACNA1A, CAMK2A, DSCAM, EHD3, FOXD1, GAS1, GLI3, HOXA1, HOXA2, KANK1, LINGO1, LRRC4C, MAG, MBP, MNX1, NEDD4L, NEURL1, NFASC, NR2E1, NTNG1, NTRK3, OMG, PCDH15, PLXNC1, POU3F2, PRKCQ, PTPRO, ROBO2, SEMA6B, SGK1, SLITRK2, SLITRK3, SNAP91, SNX10, UGT8, UNC5A, VAX1, and WNT7B, or protein encoded therefrom under conditions effective to treat or inhibit onset of Huntington's disease in the subject.

Another aspect of the present disclosure relates to a method of treating or inhibiting onset of Huntington's disease. This method involves selecting a subject having or at risk of having Huntington's disease and administering to the selected subject one or more modulators of a synapse structure or activity regulation gene selected from the group consisting of ADGRB1, ADGRL3, BCAN, CALB1, CAMK2A, FGF14, LRRTIM1, NCDN, NETO1, NEURL1, NR2E1, NTRK3, PPFIA3, ROBO2, SERPINE2, SHISA7, SIX4, SLC8A3, SLITRK2, SLITRK3, and SYNDIG1, or protein encoded therefrom under conditions effective to treat or inhibit onset of Huntington's disease in the subject.

Another aspect of the present disclosure relates to a method of treating or inhibiting onset of Huntington's disease. This method involves selecting a subject having or at risk of having Huntington's disease and administering to the selected subject one or more modulators of a synaptic signaling pathway gene selected from the group consisting of BCAN, CACNA1A, CACNA1G, CALB1, CAMK2A, CHRNA4, FGF12, FGF14, GRIA2, GRIA4, GRID2, GRIK4, KCND2, LRRTM1, MBP, MPZ, NCDN, NETO1, NEURL1, NOVA1, NR2E1, P2RX7, PDE7B, PLCL1, PPFIA3, RAPGEF4, RGS8, RIT2, S1PR2, SERPINE2, SHISA7, SLC18A1, SLC1A1, SLC1A2, SLC8A3, SNAP91, SNPH, and SYT6, or protein encoded therefrom under conditions effective to treat or inhibit onset of Huntington's disease in the subject.

Another aspect of the present disclosure relates to a method of treating or inhibiting onset of Huntington's disease. This method involves selecting a subject having or at risk of having Huntington's disease and administering to the selected subject one or more modulators of a synapse gene selected from the group consisting of ADGRB1, BCAN, BCAS1, CACNA1A, CALB1, CAMK2A, CHRNA4, CTTNBP2, DSCAM, GRIA2, GRID1, GRID2, GRIK4, HCN2, KCND2, LGI3, LRRC4C, LRRTM1, NETO1, NEURL1, NTM, P2RX7, PCDH15, PDE4B, PPFIA3, PRIMA1, PRKCQ, PTPRO, RAPGEF4, SERPINE2, SHISA7, SLC17A8, SLC18A1, SLC1A1, SLC1A2, SLC8A3, SNAP91, SNPH, SYNDIG1, and SYT6, or protein encoded therefrom under conditions effective to treat or inhibit onset of Huntington's disease in the subject.

Another aspect of the present disclosure relates to a method of treating or inhibiting onset of Huntington's disease. This method involves selecting a subject having or at risk of having Huntington's disease and administering to the selected subject one or more modulators of a monovalent inorganic cation transport gene selected from the group consisting of ABCC9, ASIC4, CACNA1A, CHRNA4, CNGB1, CNTN1, DPP10, DPP6, FGF12, FGF14, HCN2, KCND2, KCNJ9, KCNQ1, KCNS3, NALCN, NEDD4L, NKAIN4, P2RX7, PTGER3, SERPINE2, SGK1, SLC10A4, SLC17A8, SLC18A1, SLC22A3, SLC2A13, SLC5A9, SLC8A3, and SLC9A7, or protein encoded therefrom under conditions effective to treat or inhibit onset of Huntington's disease in the subject.

Another aspect of the present disclosure relates to a method of treating or inhibiting onset of Huntington's disease. This method involves selecting a subject having or at risk of having Huntington's disease and administering to the selected subject one or more modulators of a neuron projection gene selected from the group consisting of ADGRL3, ALCAM, BCAN, BCL11B, CACNA1A, CACNA1G, CALB1, CAMK2A, CHRNA4, CTTNBP2, DSCAM, GRIA2, GRIA4, GRID2, GRIK4, HCN2, KCND2, LGI3, LRRTM1, MAG, MBP, MYC, NCAM2, NCDN, NEFM, NEURL1, NFASC, NTM, PDE4B, PIK3R1, PTGER3, PTPRO, RAPGEF4, RGS8, ROBO2, SGK1, SIRT2, SLC17A8, SLC1A2, SLC8A3, SNAP91, SNPH, SYNDIG1, and UNC5A, or protein encoded therefrom under conditions effective to treat or inhibit onset of Huntington's disease in the subject.

Another aspect of the present disclosure relates to a method of treating or inhibiting onset of Huntington's disease. This method involves selecting a subject having or at risk of having Huntington's disease and administering to the selected subject one or more modulators of a TCF7L2 target gene selected from the group consisting of BMP4, CCND1, CCND2, DOCK10, DOCK9, DUSP15, ENPP4, EPAS1, EPHB1, ERBB3, EVI2A, EVI2B, FA2H, GJB1, HAPLN2, HSPA2, ID3, LGI3, MBP, MOG, MYC, MYRF, NFASC, NKAIN1, NKX6-2, OLIG2, PLEKHB1, PLP1, PPP1R16B, RAB33A, RASGEF1B, RTKN, SIRT2, SLC1A2, SOX10, ST18, TMEM125, TMEM2, TPPP, TSPAN15, UGT8, and AATK, or protein encoded therefrom under conditions effective to treat or inhibit onset of Huntington's disease in the subject.

Another aspect of the present disclosure relates to a method of treating or inhibiting onset of Huntington's disease. This method involves selecting a subject having or at risk of having Huntington's disease and administering to the selected subject one or more modulators of a gene involved in the NKX2.2→OLIG2→SOX10→MYRF regulatory cascade or protein encoded therefrom under conditions effective to treat or inhibit onset of Huntington's disease in the subject.

The present disclosure examines whether the gene expression patterns of mHTT-expressing human glial progenitor cells (hGPCs) might reflect cell-autonomous molecular pathology and, if so, whether that might predict the white matter disease of HD. Bipotential oligodendrocyte-astrocyte hGPCs were first generated from human embryonic stem cells (hESCs) derived from either huntingtin mutant embryos or their sibling controls. Fluorescence-activated cell sorting (FACS) was then used to isolate these cells based on their expression of the GPC-selective CD140a (Sim et al., "CD140a Identifies a Population of Highly Myelinogenic, Migration-Competent and Efficiently Engrafting Human Oligodendrocyte Progenitor Cells," *Nat. Biotechnol.* 29:934-941 (2011); Wang et al., "Human iPSC-Derived Oligodendrocyte Progenitor Cells Can Myelinate and Rescue a Mouse Model of Congenital Hypomyelination," *Cell Stem Cell* 12:252-264 (2013), which are hereby incorporated by reference in their entirety), followed by whole-transcriptome RNA sequencing (RNA-seq) analysis to assess mHTT-dependent changes in their gene expression. It was found that in hGPCs produced from hESCs derived from three different HD embryos, a coherent set of key transcription factors associated with both astroglial and oligodendroglial differentiation, as well as with downstream myelin biosynthesis, was significantly downregulated relative to controls as a function of mHTT expression. Accordingly, when HD hESC-derived hGPCs were transplanted into neonatal myelin-deficient and immunodeficient shiverer mice (MBP$^{shi/shi}$), the resultant glial chimeras myelinated more slowly and less completely than did littermate controls transplanted with hGPCs derived from normal control hESCs. In addition, chimeras established with HD hGPCs manifested a marked delay and disruption in astrocytic morphogenesis relative to mice chimerized with normal sibling hGPCs. Together, these data suggest that rather than being secondary to neuronal loss, white matter failure and hypomyelination in human HD might instead be the result of a cell-autonomous defect in the terminal glial differentiation of mHTT-expressing hGPCs, the occurrence of which may be central to the pathogenesis and neurological manifestations of HD.

BRIEF DESCRIPTION OF THE DRAWINGS

FIG. 1A shows principal-component analysis (PCA) based on expression of rv26,000 transcripts. The expression data are shown as transcripts per million (TPM), with post-normalization to account for variance (Risso et al., "Normalization of RNA-seq Data Using Factor Analysis of Control Genes or Samples," *Nat. Biotechnol.* 32:896-902 (2014), which is hereby incorporated by reference in its entirety). The PCA plot shows the distinct transcriptome-wide expression signature of HD-derived human glial progenitor cells (hGPCs). FIG. 1B is a Venn diagram showing intersections of lists of differentially expressed genes (DEGs) (green, downregulated; red, upregulated; fold change [FC]>2.0, FDR 1%), obtained by comparing hGPCs derived from 3 different HD patients to pooled control hGPCs from 2 donors. The list of DEGs shared by the 3 HD patients was then filtered by intersecting with those DEGs (FC>2.0, FDR 1%) found in patient HD20 (GENEA20 derived) versus a normal sibling CTR19 (GENEA19); this filtration step further increased the specificity of mHTT-associated DEGs. The gray-highlighted intersections together comprise the entire set of genes differentially expressed by all HD lines relative to their pooled controls. FIG. 1C shows an expression heatmap based on TPM values for 429 DEGs highlighted in FIG. 1B showing clustering of hGPCs by disease status. Dendrogram shows hierarchical clustering based on Euclidean distance calculated from log 2-TPM values from the three HD-ESCs lines (HD-17, HD-18, and HD-20) and the two matched control lines (CTR19 and CTR02). FIG. 1D shows a network representation of functional annotations (Gene Ontology: Biological Process and Cellular Component, Bonferroni-corrected p<0.01) for the 429 intersection DEGs highlighted in FIG. 1B. Genes are round nodes with border colors representing their direction of dysregulation (green, downregulated; red, upregulated). Rounded rectangle nodes represent annotation terms. Nodes are sized by degree and colored by closely interconnected modules (M1-M3) identified by community detection. For each module, 3 of the top annotations by significance and fold enrichment are listed. Selected gene nodes are labeled and include genes encoding key hGPC lineage transcription factors and stage-regulated proteins. FIG. 1E is an expression heatmap of 63 conserved DEGs identified in M1 (purple in (FIG. 1D), with annotations related to glial cell differentiation and myelination. FIG. 1F is an expression heatmap of 56 conserved DEGs identified in M2 (lilac in (FIG. 1D), annotations related to axon guidance and axonogenesis. FIG. 1G is an expression heatmap of 68 conserved DEGs identified in M3 (yellow in FIG. 1D), with annotations related to regulation of synapse structure and synaptic signaling. All differentially expressed (DE) results are 1% FDR and FC>2; Gene Ontology (GO) annotation results are Bonferroni corrected to p<0.01.

FIGS. 2A-2B show gene set intersection plots for differentially expressed genes obtained from comparisons of each CD140a-sorted HD-derived GPC line (HD17, HD18, and HD20), compared to pooled control-derived GPCs (FIG. 2A, up-regulated genes; FIG. 2B, down-regulated genes). Differentially expressed genes in HD GPCs are significant at 1% FDR and FC>2.00. FIGS. 2C-2D show CD44-sorted HD-derived APC line (HD17, HD18, and HD20) against control-derived APCs (FIG. 2C, up-regulated; FIG. 2D, down-regulated). Differentially expressed genes in HD APCs are significant at 5% FDR. In both, 20 vs 19 denotes the comparison of HD line HD20 (Genea20) against its sibling control line CTR19 (Genea19). Horizontal bars represent total sizes of gene sets, and vertical bars represent sizes of gene set intersections. Vertical bars are ordered first by the number of gene sets in the intersection, and then by the size of the intersection. The dots correspond to those gene sets comprising each intersection.

FIGS. 3A-3B show functional annotation reveals HD-associated impairment in transcription of glial differentiation, myelination, and synaptic transmission-related genes. Gene Ontology (GO) functional annotation was performed for the 429 differentially expressed genes (DEGs) in the 3 lines of mHTT hGPCs relative to pooled control hGPCs (see FIGS. 1B-1C). 50 significantly associated GO annotation terms (Biological Process and Cellular Component, Bonferroni-corrected p<0.01) were identified by the ToppCluster annotation tool (Kaimal et al., "ToppCluster: a Multiple Gene List Feature Analyzer for Comparative Enrichment Clustering and Network-based Dissection of Biological Systems," *Nucleic Acids Res.* 38:W96-W102 (2010), which is hereby incorporated by reference in its entirety). By network analysis, these GO terms together with their associated DEGs were grouped into three functionally related modules (M1 through M3, see FIG. 1D). For each GO term, the net-expected value assumes a constant ratio, given the number of annotated DEGs and the total number of human protein-coding genes found in the term. The fold enrichment is the ratio of the number of observed DEGs found in the term, to the expected number. Within each functional module, the GO terms were ranked first by p value, then by fold-enrichment. Three GO terms, GO:0007268 (chemical synaptic transmission), GO:0098916 (anterograde trans-synaptic signaling), and GO:0099537 (trans-synaptic signaling), were respectively ranked 3 through 5 within module M3. They contained an identical set of 37 associated DEGs, which were contained within the 38 DEGs associated to GO:0099536 (synaptic signaling) ranked at number 2 in M3. To reduce redundancy, these three GO terms were thus omitted from the figure. FIG. 3A is a bar graph showing the top 5 GO terms for each functional module. FIG. 3B is a table listing the calculated values and the associated DEGs for each of the top-ranked terms. Associated DEGs are color-coded according to their direction of dysregulation in HD- vs. control-derived hGPCs (green, down-regulated; red, up-regulated).

FIG. 4A shows an expression heatmap based on TPM values calculated from raw counts of 429 DEGs (1% FDR, FC>2.0) found in the intersection of DEGs by comparisons of hGPCs derived from each of the three different HD patients against pooled control hGPCs from two different donors. Row side colors show the Pearson's correlation coefficient (R) between the FC of that gene in each HD-derived hGPC line versus pooled controls, and the corresponding CAG repeat number in that HD line (HD17=40×CAG, HD18=46×CAG, and HD20=48×CAG). Selected genes encoding transcription factors and stage-regulated proteins involved in glial differentiation and myelination are listed. FIG. 4B shows a combined scatterplot with linear fit lines, obtained by regression of fold-changes of each of the 429 DEGs shown in the heatmap in FIG. 4A against the CAG repeat number in the corresponding hGPC line. FIG. 4C is a histogram showing the distribution of Pearson's coefficients (R) for correlation between FCs of DEGs in 3 HD lines to corresponding CAG length. For 255 of the 429 genes (|Pearson's R|>0.75), the correlation analysis indicated that the absolute magnitude of the FC increased with CAG repeat number; 228 of these genes displayed an inverse correlation of gene expression level to the CAG repeat number, with longer repeats associated with diminished glial gene expression.

FIG. 5A shows the representative lists of differentially expressed genes (DEGs) obtained from the HD-derived CD140-sorted GPCs, and the HD-derived CD44-sorted APCs were compared against the differential expression results of the mouse mHtt allelic series (FIGS. 5A and 5B) and the 6-month Q175 profiled tissues (FIGS. 5C and 5D) from (Langfelder et al., "Integrated Genomics and Proteomics Define Huntingtin CAG Length-Dependent Networks in Mice," *Nat. Neurosci.* 19:623-633 (2016), which is hereby incorporated by reference in its entirety). The network plots in FIGS. 5A and 5C show the significant pairwise set intersections between the CD140 and CD44 HD Genea-derived DEGs sets (yellow nodes), and the DEGs sets from the Langfelder et al., "Integrated Genomics and Proteomics Define Huntingtin CAG Length-Dependent Networks in Mice," *Nat. Neurosci.* 19:623-633 (2016), which is hereby incorporated by reference in its entirety, analysis (grey nodes) (Fisher's exact test, p<0.05). The nodes are sized according to the total number of DEGs, indicated in parenthesis for each node. The numbers of DEGs in the HD Genea sets are post-ID conversion to mouse orthologue genes. The edge thickness indicates the significance of the gene set intersection, calculated as −log 10 (Fisher's exact test p value). Edge color and label show the number of genes in the pairwise set intersection. Only the Langfelder et al., "Integrated Genomics and Proteomics Define Huntingtin CAG Length-Dependent Networks in Mice," *Nat. Neurosci.* 19:623-633 (2016), which is hereby incorporated by reference in its entirety, DEG sets that had a significant overlap to either of the two HD Genea sets are shown. The dot plots in FIGS. 5B and 5D show the comparisons of Gene Ontology (GO): Biological Process annotation results for the DEGs sets in FIGS. 5A and 5C, respectively. The dots are sized according to the gene ratio with respect to the DEGs set. The dot color represents the significance of the association to the GO term. All DEGs sets that had significant annotation (BH-corrected p<0.01) are shown. The most significant intersections were observed between the CD140 DEGs set and the DEGs in the 6-month striatum Q175 samples (p=1.10E-06; 150 genes) in the comparison to the allelic series DEGs and between the CD140 DEGs set and the 6-month Q175 cerebellum DEGs for the Q175 tissues (p=9.86E-13; 85 genes). These intersections included the glial modulators Nkx2-2, Olig1, and Olig2 as well as the genes encoding proteins involved in myelination, ion channel activity, and synaptic transmission. Overall, a number of similar significant annotations were observed for the HD Genea CD140 DEGs and the brain-derived DEGs from Langfelder et al., "Integrated Genomics and Proteomics Define Huntingtin CAG Length-Dependent Networks in Mice," *Nat. Neurosci.* 19:623-633 (2016), which is hereby incorporated by reference in its entirety, implicating functions that included gliogenesis, myelination, axon development, and ion channel activity.

FIG. 6A shows genes encoding key GPC lineage transcription factors and stage-regulated, myelin-related proteins. 44 genes are shown, excluding MOBP and MOG, which were noted to have a high proportion of unreliable reactions. FIG. 6B shows transcriptional targets of TCF7L2, as predicted by upstream regulator analysis in IPA. A total of 42 genes are shown, excluding four genes that had a high proportion of unreliable reactions.

FIGS. 8A-8N show myelination was impaired in mice chimerized with mHTT-expressing human GPCs. Human glial chimeric mice were established by neonatal injection of hGPCs into shiverer×rag2 hosts, which were sacrificed at 8, 13, and 18 weeks. FIGS. 8A and 8D show that, whereas myelin basic protein (MBP) expression by control hGPCs (GENEA19) was evident by 8 weeks after neonatal graft (FIG. 8A), mice engrafted with HD-derived, mHTT-expressing hGPCs (GENEA20) manifested little or no MBP immunolabeling by that point (FIG. 8D). FIGS. 8B and 8E shows that by 13 weeks, by which time mice engrafted with control hGPCs exhibited robust myelin production (FIG. 8B), only scattered islands of MBP expression were noted in matched recipients of HD-derived GPCs (FIG. 8E). FIGS. 8C and 8F show control GPC-derived myelination was increasingly robust by 18 weeks (FIG. 8C) relative to mHTT GPC chimeric mice (FIG. 8F). FIGS. 8M and 8N show that neither the density (FIG. 8G) nor the distribution of engrafted human GPCs (FIGS. 8M and 8N, dot maps) differed significantly between control and HD-derived hGPCs, indicating that the myelination defect in mHTT hGPC-engrafted brains was due to impaired oligodendroglial differentiation and myelinogenesis, rather than to differential engraftment. Scale bar, 50 mm. Values are presented as mean±SEM. p<0.01 and *p<0.001 by two-way ANOVA with Bonferroni post hoc tests.

FIGS. 9A-9F are confocal images of hGPC-engrafted shiverer corpus callosum showing the greater MBP expression and higher proportion of ensheathed axons in mice engrafted with GENEA19 control hGPCs (FIGS. 9A-9C) compared to mice engrafted with GENEA20-derived mHTT-expressing hGPCs (FIGS. 9D-9F). FIGS. 9D' and 9E' show confocal z stacks with orthogonal views of donor-derived MBP+ oligodendrocytes. FIG. 9F' shows a higher magnification of FIG. 9F, showing MBP immunoreactivity surrounding ensheathed axons. FIGS. 9G and 9H show the proportion of MBP-ensheathed NF+ host axons overall (FIG. 9G) and per MBP+ donor-derived oligodendrocyte (FIG. 9H). Scale bars represent 20 mm (FIGS. 9A-9F) and 5 mm (FIGS. 9A'-9C'). Values represent mean±SEM. p<0.01 and *p<0.001 by 2-way ANOVA with Bonferroni post hoc tests.

TABLE 1

SOX10-MYRF Transduction Restores Myelin Gene Expression in mHTT GPCs

| Target gene | GENEA-20 (mHTT) ddCt ± SEM (p-value) | GENEA-19 (normal HTT) ddCt ± SEM (p-value) |
|---|---|---|
| LINGO1 | 0.78 ± 0.64 (p = 0.41) | 0.14 ± 0.39 (p = 0.57) |
| MAG | 8.29 ± 0.92 (p = 0.0001)* | 6.21 ± 1.72 (p = 0.01)* |
| MBP | 1.97 ± 0.63 (p = 0.005)* | 0.67 ± 0.66 (p = 0.4) |
| MOG | 3.26 ± 0.53 (p = 0.02)* | 3.04 ± 0.86 (p = 0.009)* |
| MYRF-Endot | 0.33 ± 0.49 (p = 0.6) | −0.34 ± 0.23 (p = 0.18) |
| NKX2.2 | 0.57 ± 0.49 (p = 0.6) | −0.30 ± 1.06 (p = 0.85) |
| OLIG2 | −0.01 ± 0.65 (p = 0.99) | −0.57 ± 1.09 (p = 0.79) |
| OMG | −0.01 ± 0.41 (p = 0.98) | −0.81 ± 0.66 (p = 0.22) |
| PDGFRA | 2.25 ± 0.51 (p = 0.05) | 0.63 ± 0.89 (p = 0.57) |
| PLP1 | 2.10 ± 1.01 (p = 0.04)* | 1.31 ± 0.69 (p = 0.19) |
| SOX10-Endo† | 0.00 ± 0.58 (p > 0.99) | −0.68 ± 1.01 (p = 0.59) |
| TF | 4.18 ± 1.03 (p = 0.008)* | 3.52 ± 0.68 (p = 0.004)* |
| MYRF-viral†† | 10.18 ± 0.90 (p < 0.0001)* | 9.41 ± 1.15 (p = 0.0003)* |
| SOX10-viral†† | 9.89 ± 1.16 (p = 0.0002)* | 10.75 ± 0.68 (p < 0.0001)* |

These qPCR data show the ddCT values, reflecting the relative mRNA levels, of selected oligoneogenic and myelinogenic genes in normal and mHTT-expressing hGPCs, after transfection with a bicistronic plasmid expressing SOX10 and MYRF, after normalization to 18S and then control plasmid-transfected cells. Welch's t-test.
†Primers located on coding sequence
††Primers located in 3'UTRs.
Endo: endogenous gene;
Viral: viral transgene product.
*p < 0.05.

Expression values normalized to 18S and control plasmid-transfected cells of selected oligoneogenic and myelinogenic genes in both normal (Genea19, black bars) and mHTT-expressing (Genea 20, red) hGPCs, after transfection with a bicistronic plasmid expressing SOX10 and MYRF. Welch's t-test comparisons of: 1) SOX10-MYRF- vs EGFP-transfected for each line independently, significance indicated by asterisks; or 2) SOX10-MYRF-transfected Genea 20, vs. EGFP control-transfected Genea19 (significance indicated by hash marks). */#p<0.05. /##p<0.01.; */###p<0.001. †; ****/####p<0.0001. †, Primers located on coding sequence; ††, primers located in 3'UTRs.

Figures 11E, 11F, 11G, 11H, 11I, 11J, 11K, 11L, 11M:
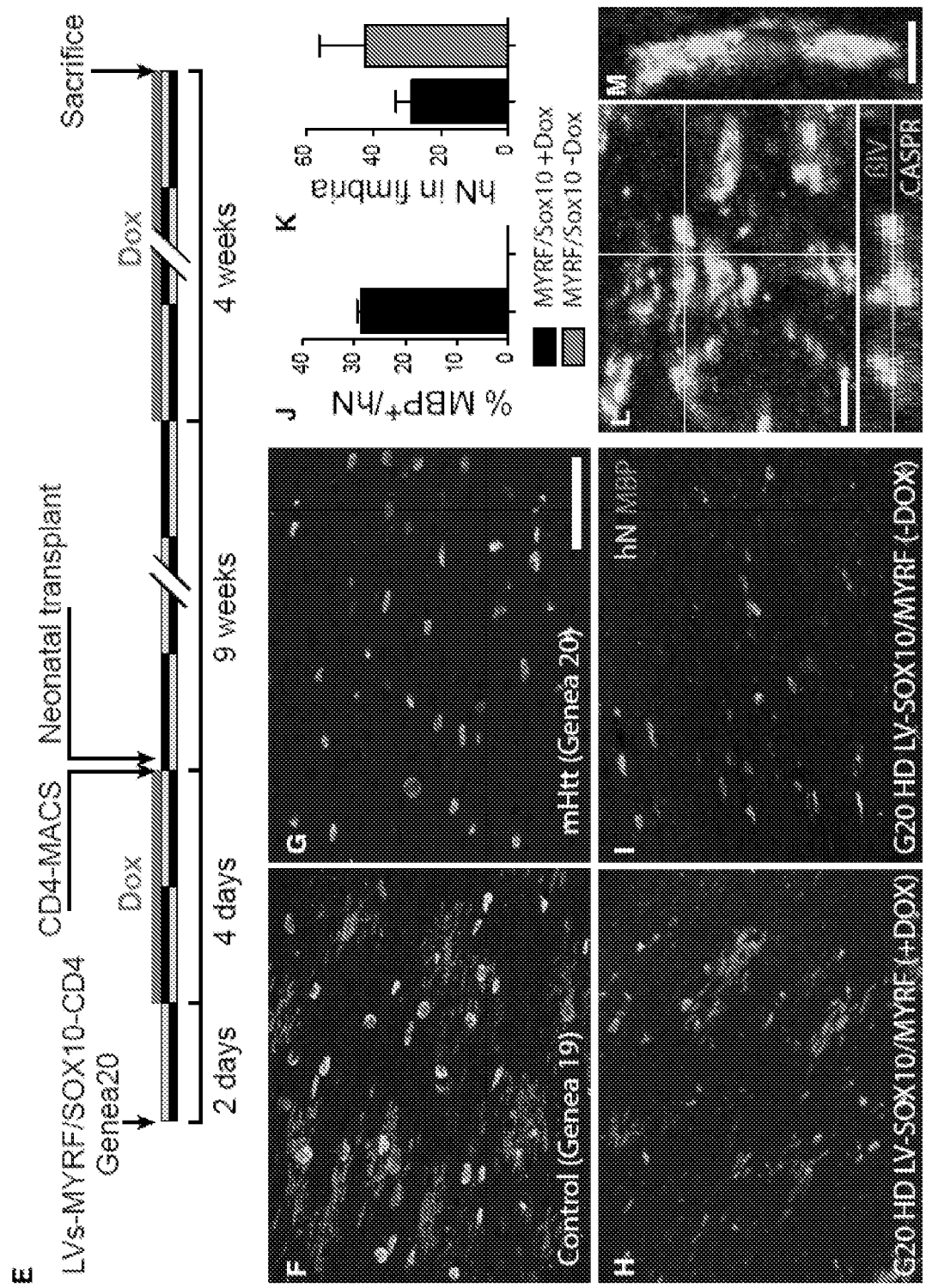

FIGS. 11A-11M show SOX10 and MYRF rescued oligodendrocyte differentiation and myelinogenesis by mHTT GPCs. FIG. 11A shows a doxycycline-regulated dual vector lentiviral (LV) transduction strategy that allows the doxycycline (DOX)-triggered, interdependent overexpression of SOX10 and MYRF, with concurrent expression of CD4 to permit FACS-based immunoisolation of SOX10-MYRF-transduced hGPCs. FIGS. 11B-11D show the effects of SOX10 and MYRF overexpression in mHTT-expressing hGPCs were assessed by transducing matched sets of 180 DIV GENEA20-derived hGPCs with DOX-regulated lentiviral SOX10/MYRF and exposing some cultures to DOX while leaving matched control cultures untreated. After an additional week in vitro, the cells were immunostained using mAb O4, which recognizes oligodendrocytic sulfatide. Without DOX, the mHTT hGPCs were stably maintained and expressed no detectable O4 (FIG. 11B). In contrast, those mHTT hGPCs raised in DOX (FIG. 11C), with upregulated SOX10 and MYRF expression, exhibited a sharp and significant increase in oligodendrocyte differentiation (FIG. 11D). This schematic outlines the experimental design used to assess the in vivo myelinogenic competence of HD-derived hGPCs, with and without rescue of SOX10 and MYRF expression. All cells were exposed transiently to DOX in vitro so as to initiate CD4 expression and permit FACS isolation before transplant into neonatal immunodeficient shiverer mice. At 9 weeks of age, the engrafted mice were either given DOX for another 4 weeks to initiate SOX10 and MYRF expression (+DOX) or not so treated (–DOX, controls). Shiverer mice engrafted neonatally with hGPCs derived from normal HTT-expressing hESCs (GENEA19) developed abundant MBP expression and oligodendrocytic morphologies by 13 weeks in vivo. In contrast, mice engrafted with mHTT-expressing hGPCs produced from HD hESCs (GENEA20 [G20]) developed little detectable MBP by that point. FIGS. 11H and 11I show that at 9 weeks of age, some GENEA20 mHTT hGPC-engrafted mice were given oral DOX to trigger SOX10 and MYRF expression (FIG. 11H), while matched controls were not given dox (FIG. 11I). The DOX(+) mice exhibited significant numbers of MBP+ myelinating oligodendrocytes in the engrafted white matter (FIG. 11H). FIGS. 11J and 11K show that by that same time point, no donor cells in the DOX(–) control mice had developed MBP expression (FIG. 11J), despite analogous donor cell engraftment (FIG. 11K). FIGS. 11L and 11M show that in the DOX(+) mice engrafted with SOX10/MYRF-transduced GENEA20 hGPCs, the donor-derived oligodendrocytes induced the robust formation of nodes of Ranvier (FIG. 11L), evidenced by the clustering of BIV-spectrin flanked by Caspr protein that typifies nodal architecture (FIG. 11M), which is otherwise absent in untreated shiverer brain. Scale bars represent 50 mm (FIGS. 11B, 11C, and 11F-11I,), 1 mm (FIG. 11L), and 0.5 mm (FIG. 11M). Values represent means±SEM. ***p<0.001 (t test).

Figures 12A, 12B, 12C, 12D, 12E, 12F, 12G, 12H:
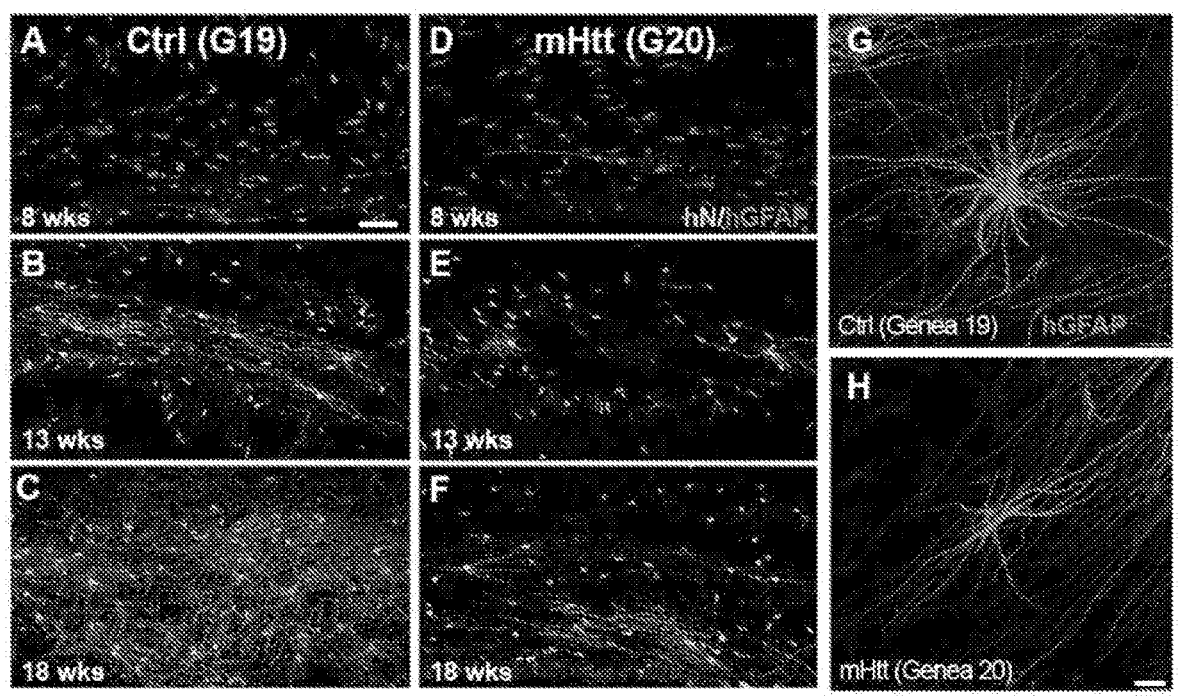
Figures 12O, 12P:
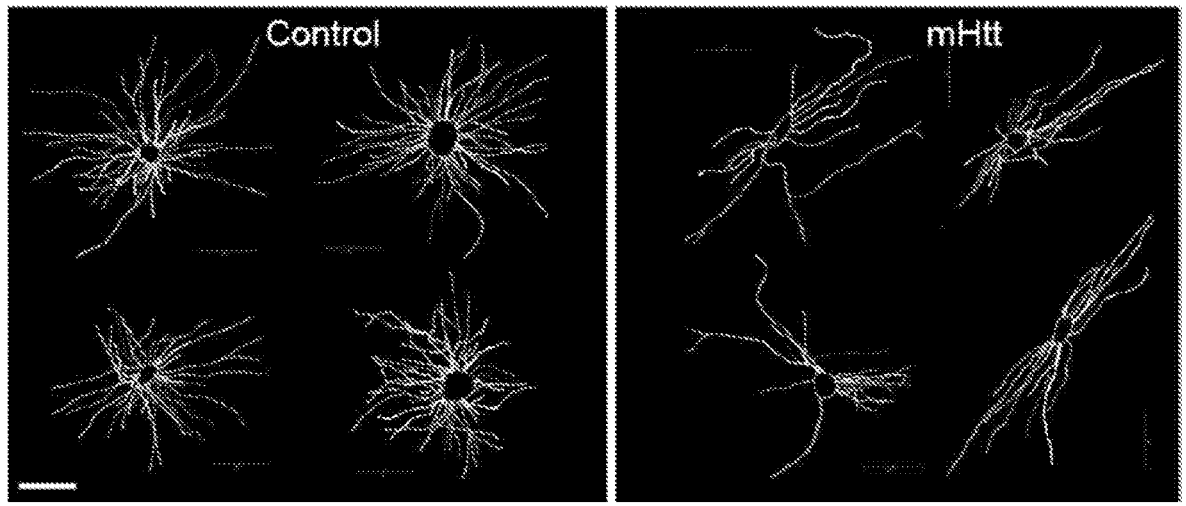

FIGS. 12A-12P show astrocytic differentiation is delayed in mHTT GPCs. FIGS. 12A-12C show astrocytic differentiation was significantly delayed in mHTT glial chimeras. Mice neonatally transplanted with normal HTT GENEA19-derived hGPCs began to develop significant donor-derived GFAP+ astrocytes by 8 weeks (FIG. 12A), robustly so by 13 weeks (FIG. 12B), with dense astrocytic colonization of the callosal white matter by 18 weeks (FIG. 12C). FIGS. 12D-12F show, in contrast, mHTT-expressing hGPCs derived from GENEA20 sibling hESCs developed astrocytic phenotype more slowly, with little evident GFAP expression at 8 weeks (FIG. 12D) and 13 weeks (FIG. 12E) and only modest GFAP+ astrocytic maturation at 18 weeks (FIG. 12F). FIGS. 12G and 12H show the mature astrocytic morphologies of control (FIG. 12G) and mHTT-expressing (FIG. 12H) astrocytes differed in that mHTT astrocytes typically failed to manifest the degree of radial symmetry of their control-derived counterparts. FIG. 12I show that the proportion of GFAP-expressing cells among all donor cells was consistently lower in mHTT hGPC-engrafted mice than control-engrafted mice. FIGS. 12J-12M show Sholl analysis of cells traced in NeuroLucida in 3D, and shown flattened in FIG. 12O and FIG. 12P, revealed that normal donor astrocytes exhibited greater fiber complexity (FIG. 12J) and more primary processes (FIG. 12K) yet shorter average and maximal fiber lengths (FIGS. 12L and 12M) than mHTT-expressing astroglia. FIGS. 12N-12P show Fan-in radial analysis of volume occupancy (Dang et al., "Formoterol, a Long-Acting β2 Adrenergic Agonist, Improves Cognitive Function and Promotes Dendritic Complexity in a Mouse Model of Down Syndrome," *Biol. Psychiatry* 75:179-188 (2014), which is hereby incorporated by reference in its entirety) revealed that mHTT astrocytes had significantly more regions unoccupied by glial processes than did control astrocytes (FIG. 12N). Illustrations in FIG. 12O and FIG. 12P indicate their discontiguous domain structure. Values represent mean±SEM. *p<0.05; p<0.01; *p<0.001 by 2-way ANOVA with Bonferroni's post hoc tests (FIG. 12I), comparison of nonlinear regressions (p<0.0001) (FIG. 12J), and unpaired t tests comparing per-mouse average values across all cells scored (FIGS. 12K-12N) (n=4 control, 7 mHTT mice). Scale bars represent 25 mm (FIGS. 12A-12F) and 10 mm (FIGS. 12G, 12H, 12O, and 12P).

Figure 13A:
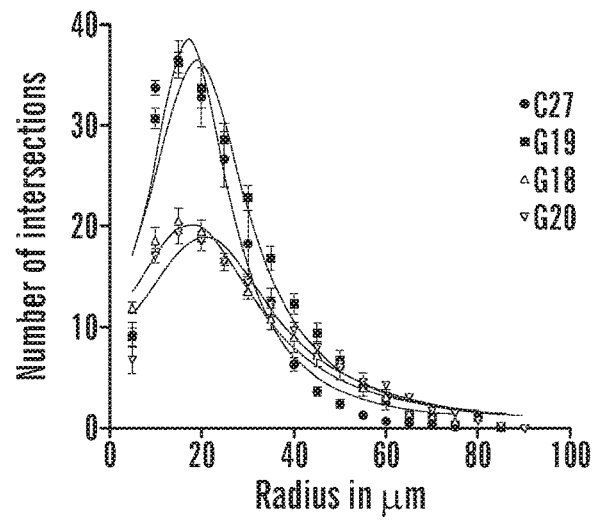
Figure 13B:
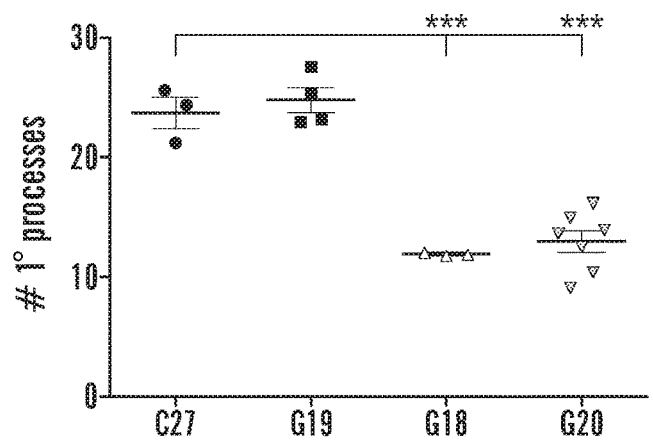
Figure 13C:
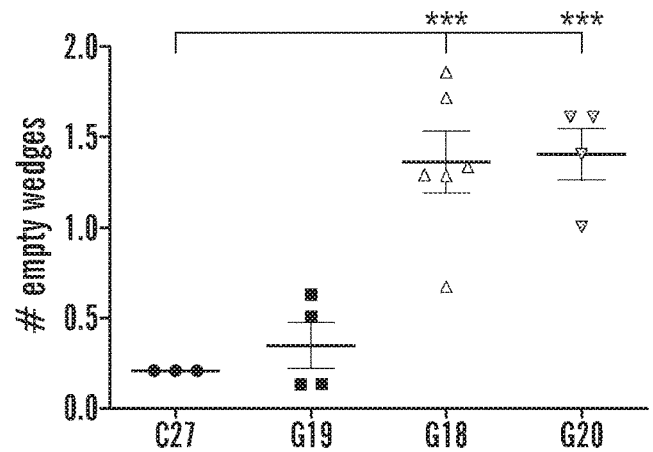
Figure 13E:
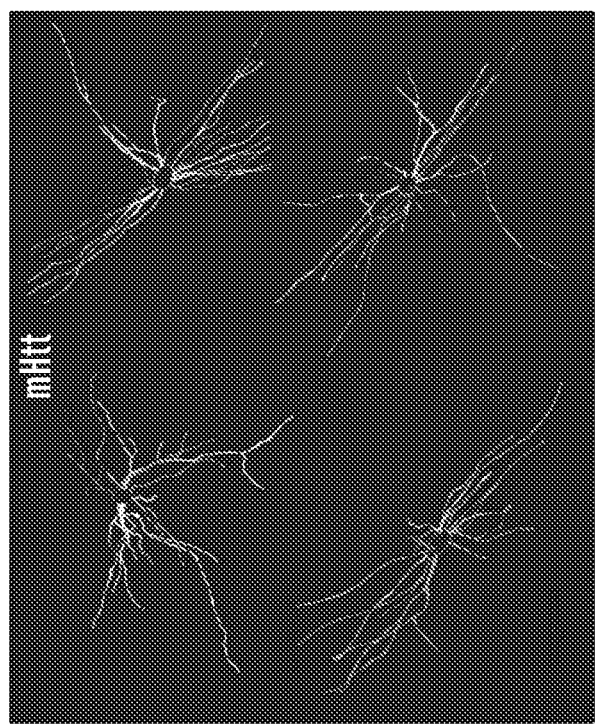
Figure 13D:
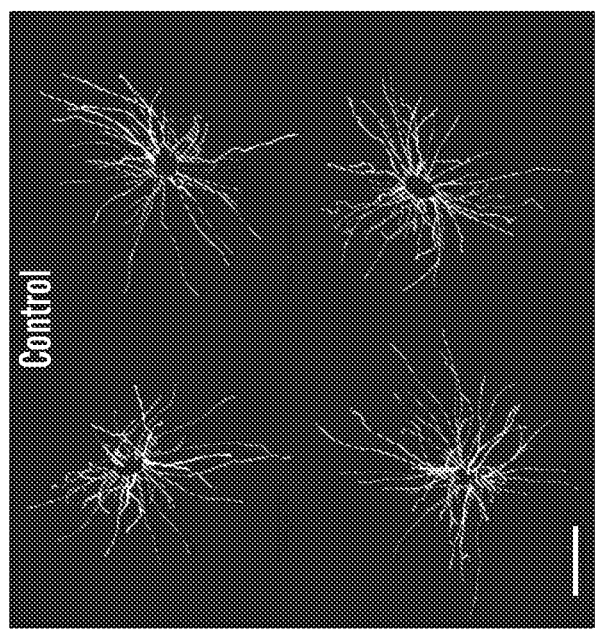

FIGS. 13A-13E show mHTT-expressing astrocytes exhibit diminished complexity and incomplete domain structures. FIG. 13A shows Sholl analysis of GFAP-immunostained human cells in human glial chimeras, 18 weeks after neonatal implantation. Non-linear regression curves of radial intersections for each cell line (Lorentizan curve-fit), as a function of branch order are shown. Comparison of control (N=7) vs mHTT mice (N=10); p<0.0001. FIG. 13B shows both the normal HTT control line GENEA19, and the unrelated normal HTT hiPS cell line C27 have more primary processes than the mHTT-expressing GENEA lines, GENEA18 and GENEA20. The controls GENEA19 and C27 are no different from one another, but both GENEA18 and GENEA20 are significantly different from the controls (1-way ANOVA with Dunnett's post-ttest; p<0.0001). FIG. 13C shows the fiber distributions of astrocytes derived from the two control lines, C27 and GENEA19, are more radially symmetric than those of either mHTT line. One-way ANOVA with Dunnett's post-test, and C27 as the control, p<0.0001. Both GENEA18 and GENEA20 are significantly different from C27, p<0.0001. FIGS. 13A-13C, Controls: C27, gray; and GENEA 19, black. HD-derived: GENEA 18, orange; GENEA 20, red. FIG. 13D shows flattened 3-dimensional coronal tracings of astrocytes from the corpus callosum of mice transplanted with C27-derived control hGPCs, compared to those of mice transplanted with GENEA18-derived hGPCs (FIG. 13E). Scale: FIG. 13D, 25 μm.

Figure 14A:
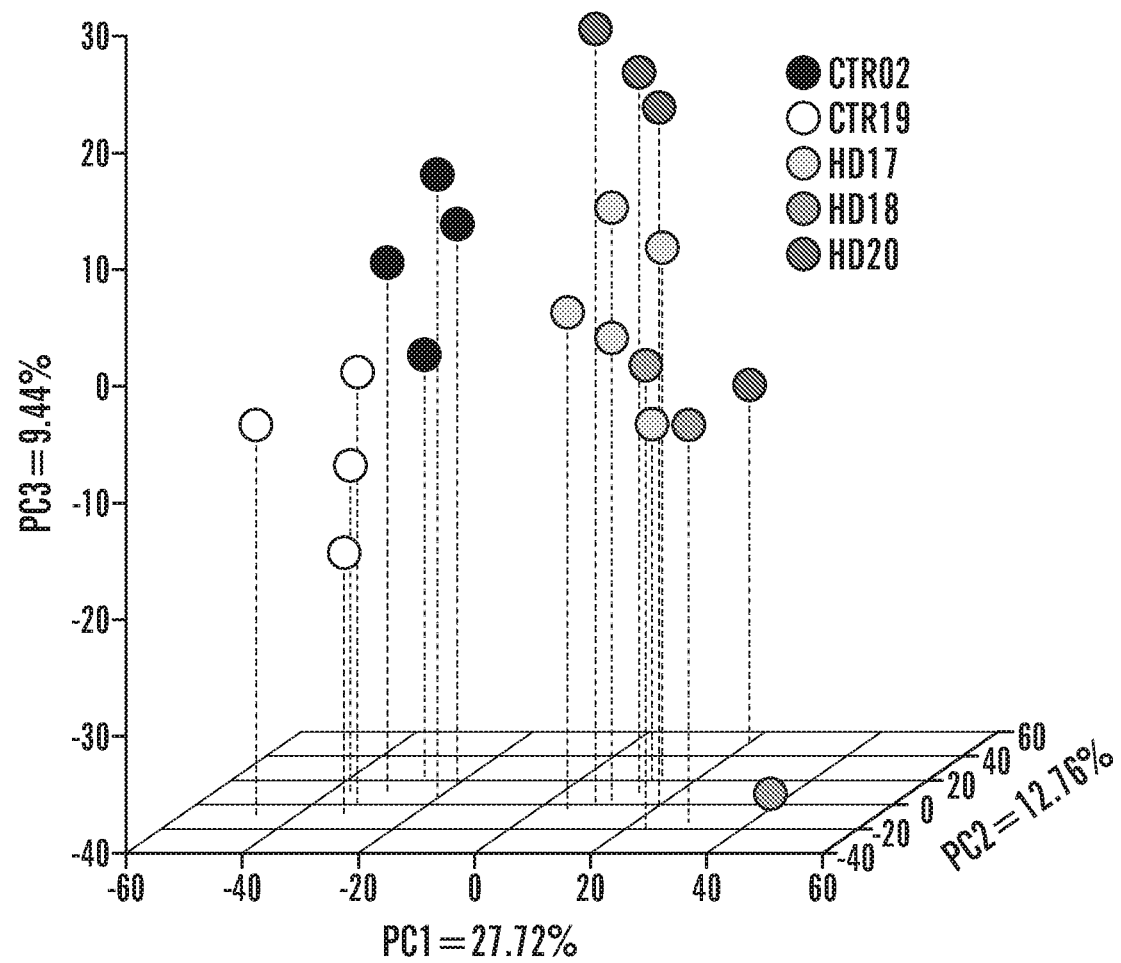
Figure 14B:
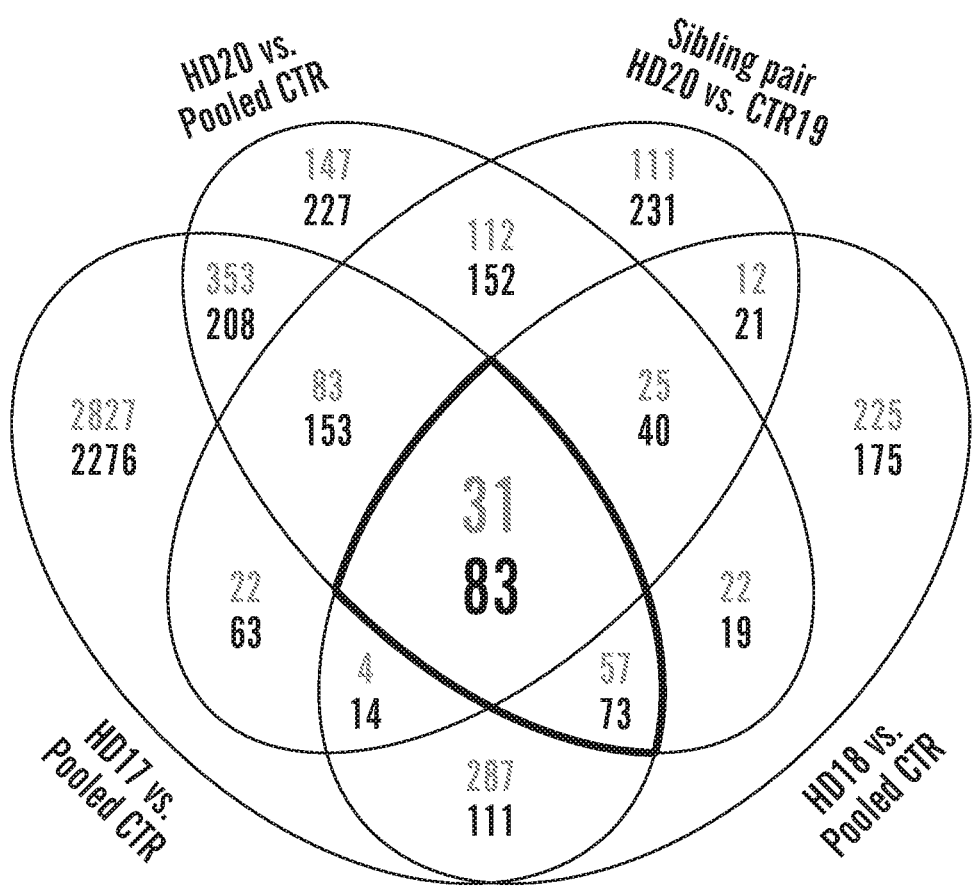
Figure 14C:
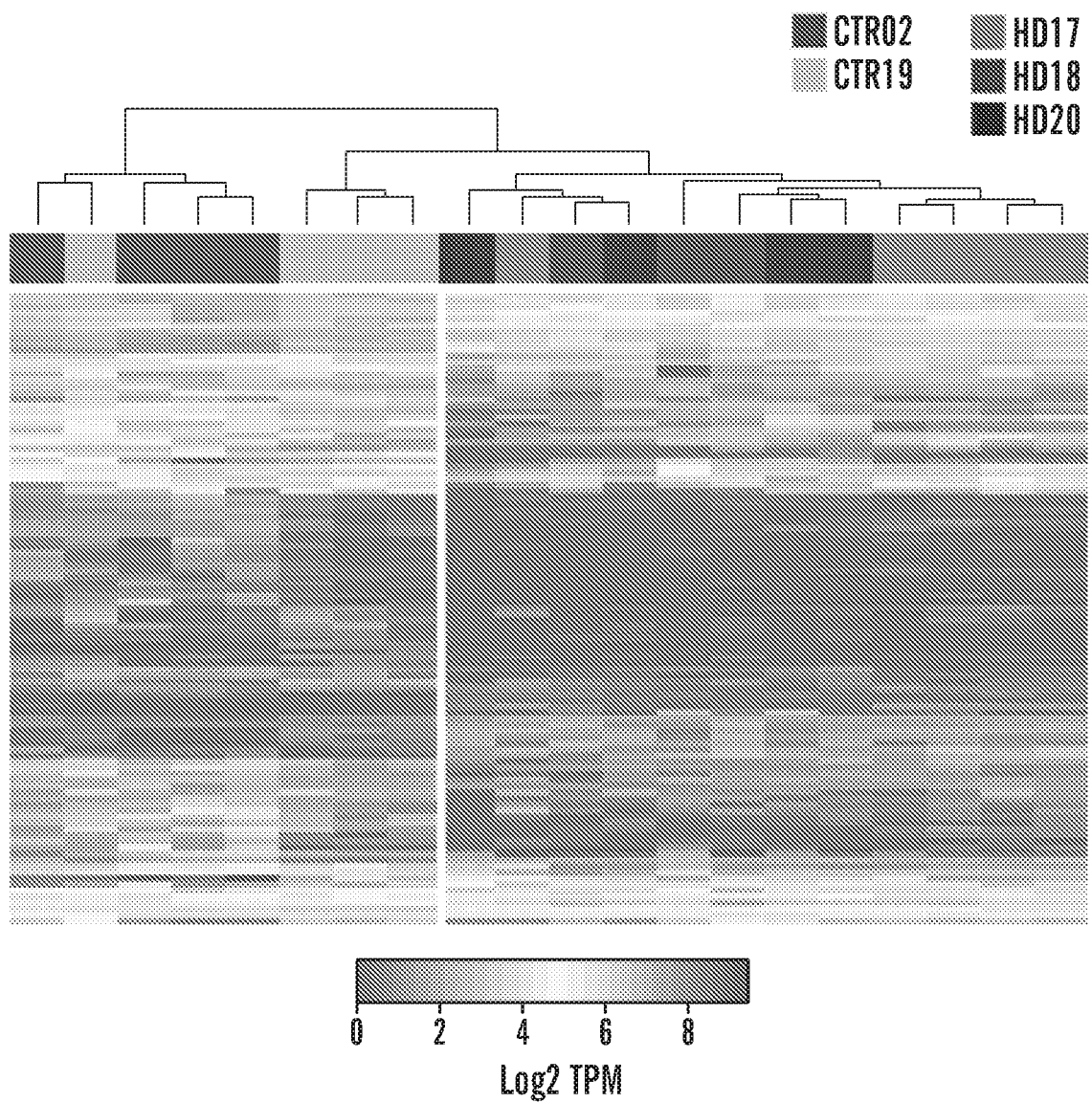
Figure 14D:
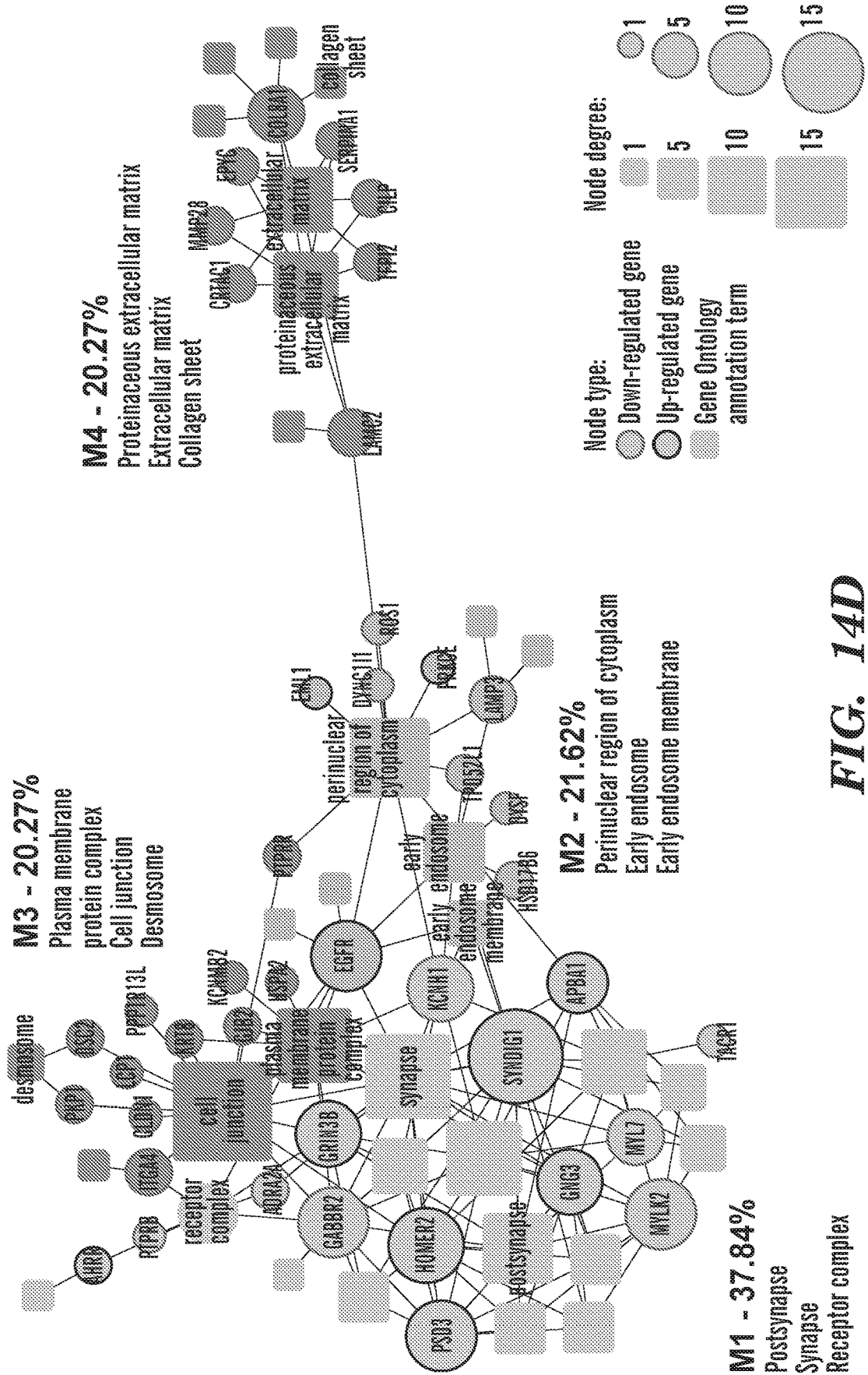
Figure 14E:
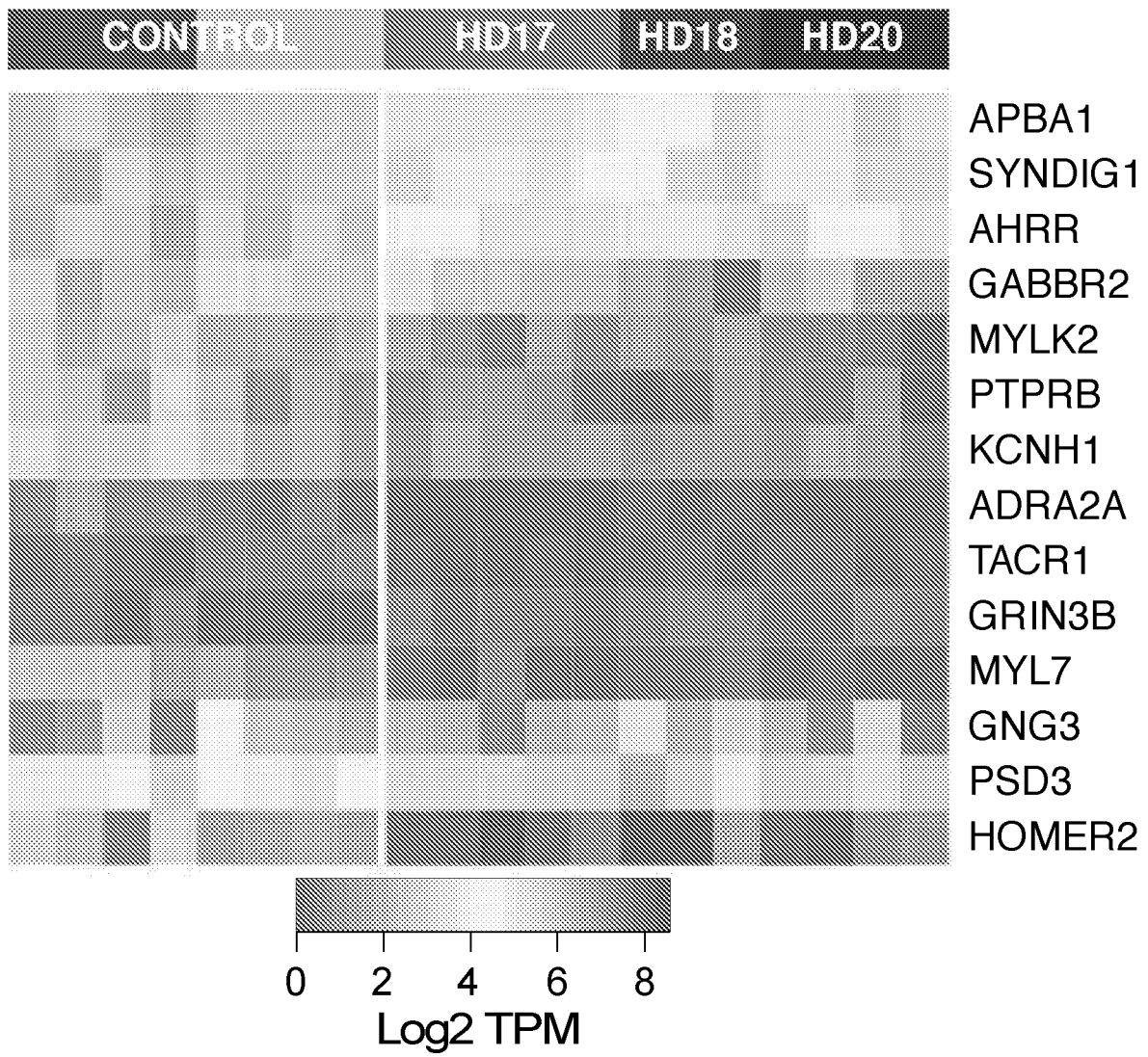
Figure 14F:
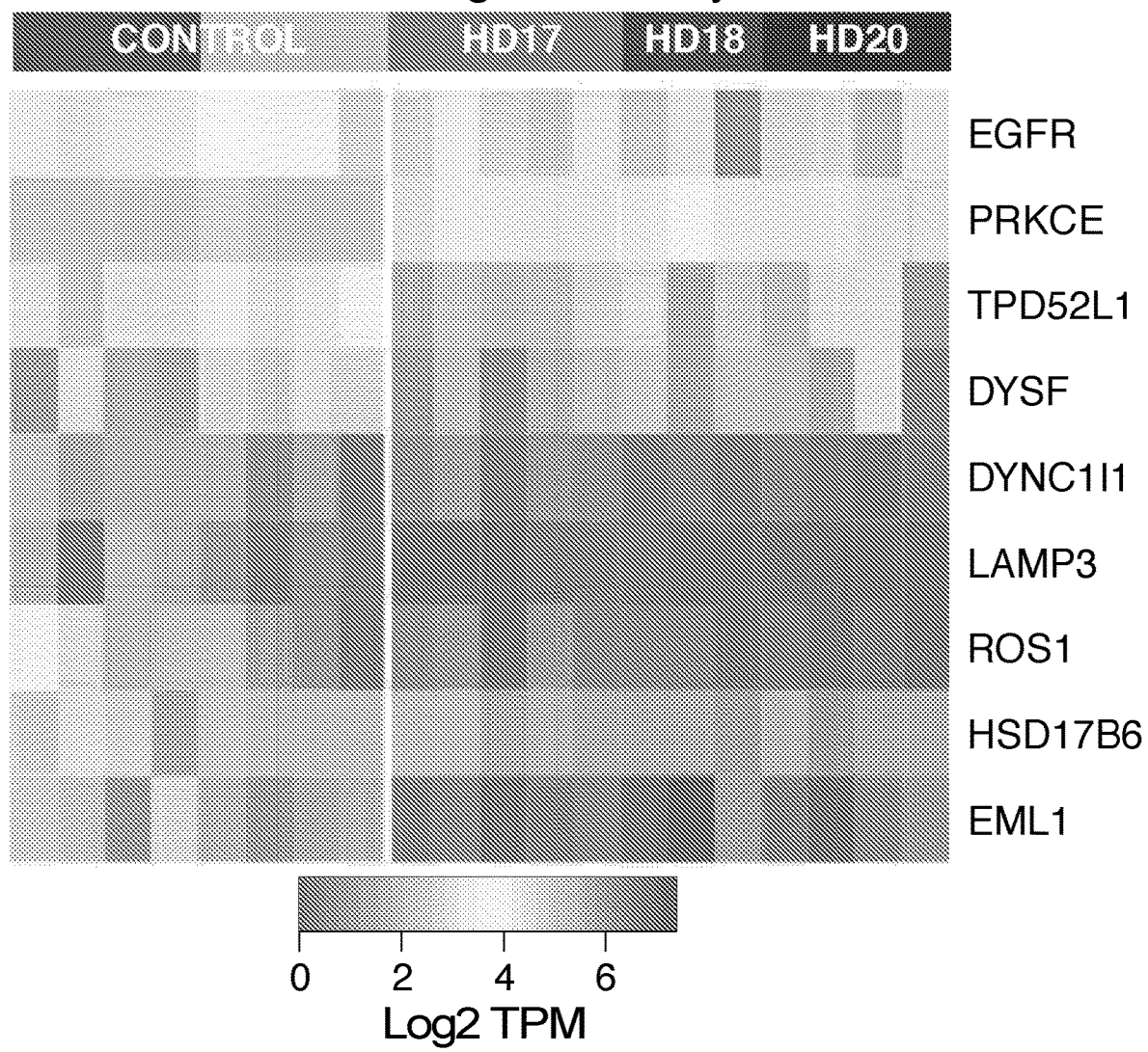
Figure 14G:
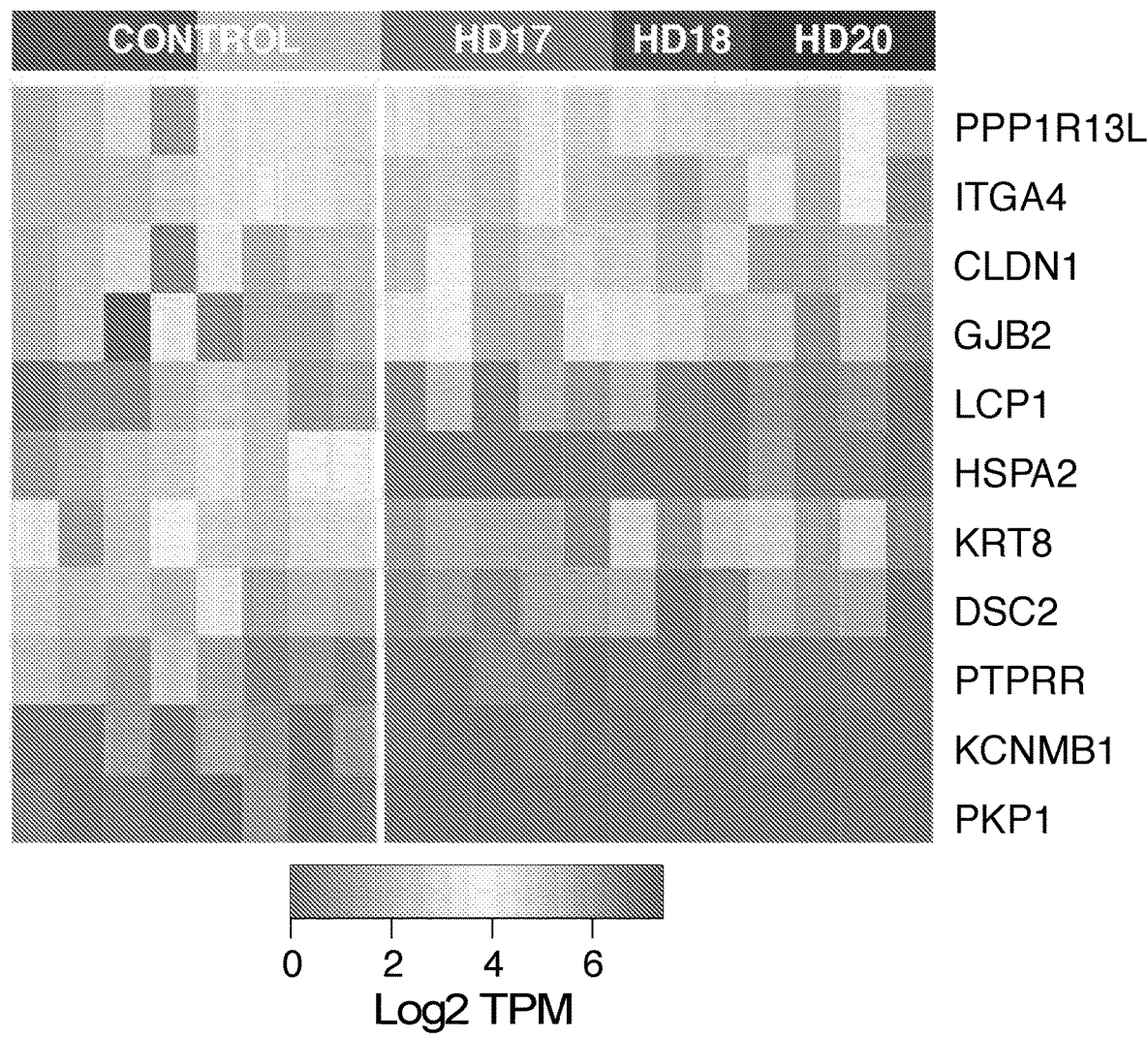
Figure 14H:
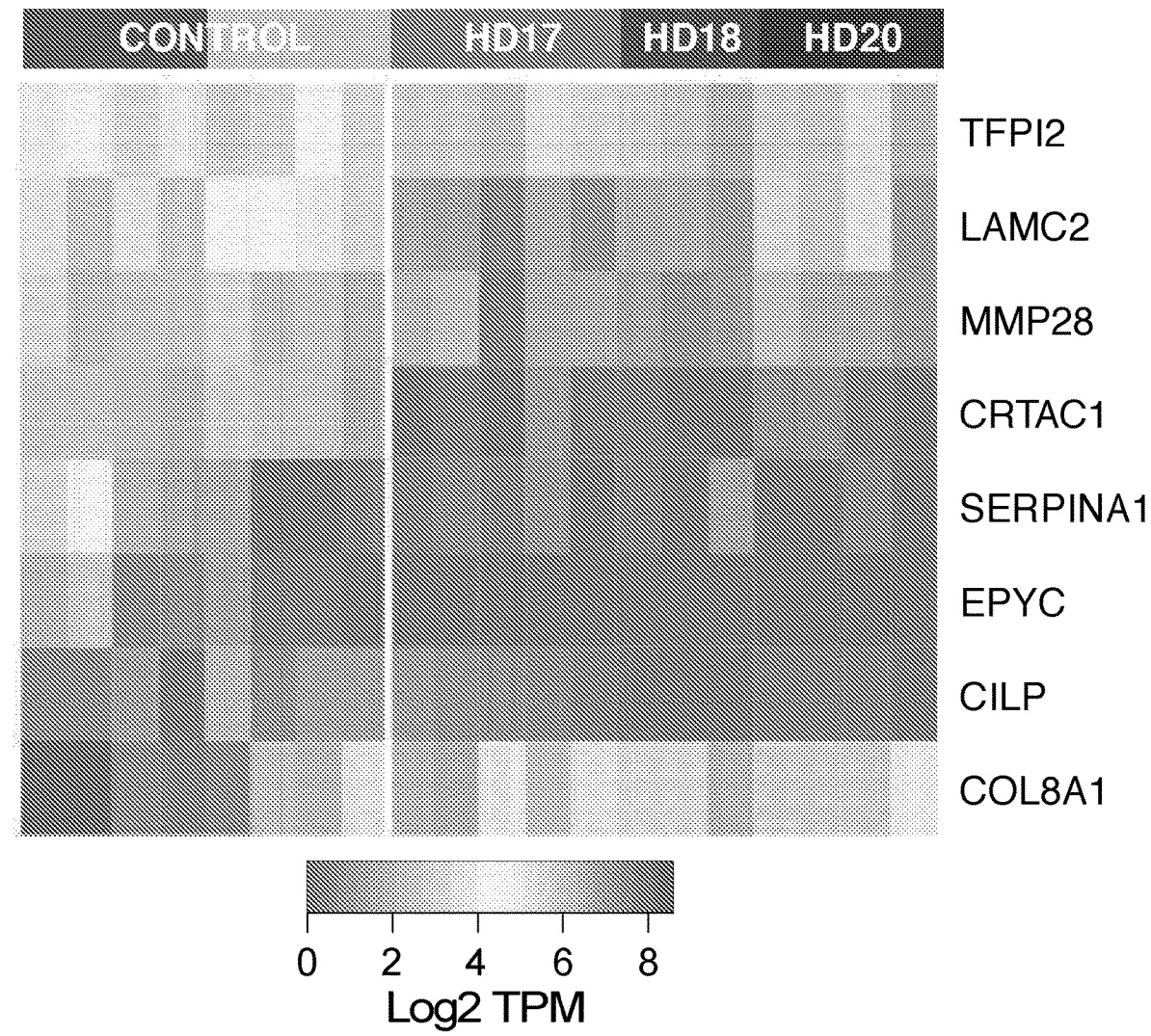

FIGS. 14A-14H show HD hESC-derived CD44+ astroglia exhibit mHTT-dependent changes in gene expression. FIG. 14A shows PCA performed as in FIG. 1A but using CD44-sorted astroglia and their precursors validates the segregated expression signatures of HD-derived and normal cells. FIG. 14B shows a Venn diagram that highlights the intersection of lists of DEGs (green, downregulated; red, upregulated; FDR 5%) obtained by comparing astroglia derived from 3 HD patients against pooled control cells and using the same cell lines and analytic pipeline as in FIG. 1. The list of DEGs shared by the 3 HD patients was filtered by those genes differentially expressed by patient HD20 (GENEA20) relative to its sibling donor CTR19 (GENEA19). FIG. 14C shows a heatmap based on log 2-transformed TPM values calculated from raw counts of the 114 DEGs highlighted in (FIG. 14B) showing clustering by disease status. FIG. 14D shows a network representation of functional annotations (Gene Ontology: Cellular Component, FDR-corrected p<0.1) for the 114 intersection DEGs highlighted in (FIG. 14B). Genes are designated as round nodes (green, down-regulated; red, upregulated; rounded rectangular nodes represent annotation terms. Nodes are sized by degree and grouped as interconnected modules (M1-M4) identified by community detection. For each colored module, three of the top significant annotations are listed and labeled in the network. FIG. 14E shows an expression heatmap of 14 conserved DEGs identified in M1 (yellow in (FIG. 14D), with annotations related to post-synaptic and receptor complex components. FIG. 14F shows a heatmap of 9 conserved DEGs identified in M2 (gray in (FIG. 14D), annotated to perinuclear and early endosome components. FIG. 14G shows a heatmap of 11 conserved DEGs identified in M3 (blue in (FIG. 14D), with annotations related to plasma membrane, cell-cell junction, and desmosomal components. FIG. 14H shows a heatmap of 8 DEGs identified in M4 (orange in (FIG. 14D), with annotations related to extracellular matrix components.

DETAILED DESCRIPTION

The disclosure herein relates generally to a method of treating or inhibiting onset of Huntington's disease. This method involves selecting a subject having or at risk of having Huntington's disease and administering to the subject one or modulators of one or more genes as described in Table 2 or Table 3, or proteins encoded therefrom, under conditions effective to treat or inhibit onset of Huntington's disease in the subject.

TABLE 2

| Genes Enriched in HD-derived hGPCS Compared to Controls | | | |
|---|---|---|---|
| BARD1 | BRCA1 associated RING domain 1 | ABCC9 | ATP binding cassette subfamily C member 9 |
| ASAH2 | N-acylsphingosine amidohydrolase 2 | SLC1A2 | solute carrier family 1 member 2 |
| RGS8 | regulator of G protein signaling 8 | MGAT4C | MGAT4 family member C |
| ARL4C | ADP ribosylation factor like GTPase 4C | LINC01158 | long intergenic non-protein coding RNA 1158 |
| SHB | SH2 domain containing adaptor protein B | RND3 | Rho family GTPase 3 |
| RFTN1 | raftlin, lipid raft linker 1 | SRRM4 | serine/arginine repetitive matrix 4 |
| FGD4 | FYVE, RhoGEF and PH domain containing 4 | ZNF718 | zinc finger protein 718 |
| GLI3 | GLI family zinc finger 3 | GRAMD1C | GRAM domain containing 1C |
| KIF15 | kinesin family member 15 | GAS1 | growth arrest specific 1 |
| CCDC109B | mitochondrial calcium uniporter dominant negative beta subunit | TMSB4XP6 | thymosin beta 4, X-linked pseudogene 6 |
| ZNF217 | zinc finger protein 217 | BCL11B | B-cell CLL/lymphoma 11B |
| CDCA7L | cell division cycle associated 7 like | OSTM1-AS1 | OSTM1 antisense RNA 1 |
| LDB2 | LIM domain binding 2 | VAX1 | ventral anterior homeobox 1 |
| ROBO2 | roundabout guidance receptor 2 | SVIL-AS1 | SVIL antisense RNA 1 |
| FAM111B | family with sequence similarity 111 member B | LOC100507616 | |
| MAML3 | mastermind like transcriptional coactivator 3 | NEDD4L | neural precursor cell expressed, developmentally down-regulated 4-like, E3 ubiquitin protein ligase |
| KITLG | KIT ligand | SLC10A4 | solute carrier family 10 member 4 |
| GAS2L3 | growth arrest specific 2 like 3 | LINC01550 | long intergenic non-protein coding RNA 1550 |
| ST8SIA2 | ST8 alpha-N-acetyl-neuraminide alpha-2,8-sialyltransferase 2 | FDPSP8 | farnesyl diphosphate synthase pseudogene 8 |
| TRIM36 | tripartite motif containing 36 | WIPF3 | WAS/WASL interacting protein family member 3 |
| CCND2 | cyclin D2 | ZNF572 | zinc finger protein 572 |
| LOC105370423 | | LINC01159 | long intergenic non-protein coding RNA 1159 |
| RIMKLA | ribosomal modification protein rimK like family member A | SLFN11 | schlafen family member 11 |
| POU3F2 | POU class 3 homeobox 2 | SLFN13 | schlafen family member 13 |
| LINC01563 | long intergenic non-protein coding RNA 1563 | AMBN | ameloblastin |
| HAT1 | histone acetyltransferase 1 | OAS3 | 2'-5'-oligoadenylate synthetase 3 |
| LOC646903 | uncharacterized LOC646903 | LOC105378132 | uncharacterized LOC105378132 |
| LOC105373502 | uncharacterized LOC105373502 | MICB | MHC class I polypeptide-related sequence B |
| CCNE2 | cyclin E2 | LOC107985928 | |
| NR2E1 | nuclear receptor subfamily 2 group E member 1 | HS3ST4 | heparan sulfate-glucosamine 3-sulfotransferase 4 |
| GCA | grancalcin | LOC107987330 | |
| PLXNC1 | plexin C1 | | |
| BLACAT1 | bladder cancer associated transcript 1 (non-protein coding) | | |

TABLE 3

| Genes Downregulated in HD-derived hGPCS Compared to Controls | | | |
|---|---|---|---|
| LOC105377382 | uncharacterized LOC105377382 | ASIC4 | acid sensing ion channel subunit family member 4 |
| MEG3 | maternally expressed 3 (non-protein coding) | SNX22 | sorting nexin 22 |
| BCAS1 | breast carcinoma amplified sequence 1 | TCERG1L | transcription elongation regulator 1 like |
| MOG | myelin oligodendrocyte glycoprotein | CDH22 | cadherin 22 |
| KLRC4-KLRK1 | killer cell lectin like receptor K1 | BAMBI | BMP and activin membrane bound inhibitor |
| SOX10 | SRY-box 10 | TMEFF2 | transmembrane protein with EGF like and two follistatin like domains 2 |
| NKX2-2 | NK2 homeobox 2 | FOXD1 | forkhead box D1 |
| MAG | myelin associated glycoprotein | P2RX7 | purinergic receptor P2X 7 |
| VGLL2 | vestigial like family member 2 | EXTL1 | exostosin like glycosyltransferase 1 |
| SPATA8 | spermatogenesis associated 8 | OXCT2 | 3-oxoacid CoA-transferase 2 |
| GPR17 | G protein-coupled receptor 17 | XKR4 | XK related 4 |
| UGT8 | UDP glycosyltransferase 8 | NR3C2 | nuclear receptor subfamily 3 group C member 2 |
| ANO3 | anoctamin 3 | KIZ | kizuna centrosomal protein |
| HSPA2 | heat shock protein family A (Hsp70) member 2 | REPS2 | RALBP1 associated Eps domain containing 2 |
| MBP | myelin basic protein | NCAM2 | neural cell adhesion molecule 2 |
| CA10 | carbonic anhydrase 10 | PLEKHH2 | pleckstrin homology, MyTH4 and FERM domain containing H2 |
| RHOH | ras homolog family member H | MRVI1 | murine retrovirus integration site 1 homolog |
| CNGB1 | cyclic nucleotide gated channel beta 1 | LOC101927699 | uncharacterized LOC101927699 |
| PPP1R16B | protein phosphatase 1 regulatory subunit 16B | LOC107985847 | uncharacterized LOC107985847 |
| LOC105372556 | uncharacterized LOC105372556 | PLLP | plasmolipin |
| PLPPR1 | phospholipid phosphatase related 1 | ADGRL3 | adhesion G protein-coupled receptor L3 |
| FA2H | fatty acid 2-hydroxylase | DIRAS2 | DIRAS family GTPase 2 |
| VSTM2B | V-set and transmembrane domain containing 2B | ATP13A5 | ATPase 13A5 |
| SLCO4A1-AS1 | SLCO4A1 antisense RNA 1 | LOC100129455 | uncharacterized LOC100129455 |
| LOC105377656 | | NEU4 | neuraminidase 4 |
| EYA1 | EYA transcriptional coactivator and phosphatase 1 | LOC105378745 | uncharacterized LOC105378745 |
| LOC105378404 | uncharacterized LOC105378404 | ADGRG2 | adhesion G protein-coupled receptor G2 |
| KLRC3 | killer cell lectin like receptor C3 | DGKG | diacylglycerol kinase gamma |
| CNTN3 | contactin 3 | FBXW4 | F-box and WD repeat domain containing 4 |
| SLITRK3 | SLIT and NTRK like family member 3 | CSMD1 | CUB and Sushi multiple domains 1 |
| ACAN | aggrecan | LOC107985796 | |
| COL20A1 | collagen type XX alpha 1 chain | FREM1 | FRAS1 related extracellular matrix 1 |
| KCND2 | potassium voltage-gated channel subfamily D member 2 | PPFIBP2 | PPFIA binding protein 2 |
| COL6A4P2 | collagen type VI alpha 4 pseudogene 2 | LOC101928100 | uncharacterized LOC101928100 |
| SLC17A8 | solute carrier family 17 member 8 | CMTM8 | CKLF like MARVEL transmembrane domain containing 8 |
| PRKG2 | protein kinase, cGMP-dependent, type II | SIRT2 | sirtuin 2 |
| LIMS2 | LIM zinc finger domain containing 2 | TPTE2P1 | transmembrane phosphoinositide 3-phosphatase and tensin homolog 2 pseudogene 1 |
| ENPP6 | ectonucleotide pyrophosphatase/ phosphodiesterase 6 | SKAP2 | src kinase associated phosphoprotein 2 |
| PADI2 | peptidyl arginine deiminase 2 | C14orf39 | chromosome 14 open reading frame 39 |
| C2orf27B | chromosome 2 open reading frame 27A | OLIG1 | oligodendrocyte transcription factor 1 |
| RIT2 | Ras like without CAAX 2 | LINC00936 | ATP2B1 antisense RNA 1 |
| PCDH15 | protocadherin related 15 | TMEM121 | transmembrane protein 121 |
| C2orf27A | chromosome 2 open reading frame 27A | CHADL | chondroadherin like |
| CSMD3 | CUB and Sushi multiple domains 3 | MMP17 | matrix metallopeptidase 17 |
| GRIA4 | glutamate ionotropic receptor AMPA type subunit 4 | CABLES1 | Cdk5 and Abl enzyme substrate 1 |
| CNTN1 | contactin 1 | TMEM63C | transmembrane protein 63C |
| DOCK10 | dedicator of cytokinesis 10 | NOVA1-AS1 | NOVA1 antisense RNA 1 (head to head) |
| LOC105375469 | uncharacterized LOC105375469 | CAPSL | calcyphosine like |
| HMX1 | H6 family homeobox 1 | GDNF-AS1 | GDNF antisense RNA 1 (head to head) |

TABLE 3-continued

Genes Downregulated in HD-derived hGPCS Compared to Controls

| | | | |
|---|---|---|---|
| SLC18A1 | solute carrier family 18 member A1 | ALCAM | activated leukocyte cell adhesion molecule |
| HOXA4 | homeobox A4 | LRRTM1 | leucine rich repeat transmembrane neuronal 1 |
| LOC105376244 | uncharacterized LOC105376244 | SPNS2 | sphingolipid transporter 2 |
| DLK1 | delta like non-canonical Notch ligand 1 | RTN4RL2 | reticulon 4 receptor like 2 |
| ADAMTS20 | ADAM metallopeptidase with thrombospondin type 1 motif 20 | KCNQ1 | potassium voltage-gated channel subfamily Q member 1 |
| LGR5 | leucine rich repeat containing G protein-coupled receptor 5 | HMCN2 | hemicentin 2 |
| KIAA0087 | KIAA0087 lncRNA | PPP2R2B | protein phosphatase 2 regulatory subunit Bbeta |
| ISM1 | isthmin 1 | SHROOM4 | shroom family member 4 |
| ZNF469 | zinc finger protein 469 | KHDRBS3 | KH RNA binding domain containing, signal transduction associated 3 |
| NETO1 | neuropilin and tolloid like 1 | KIF6 | kinesin family member 6 |
| LOC105373406 | uncharacterized LOC105373406 | OPN5 | opsin 5 |
| LHFPL3 | lipoma HMGIC fusion partner-like 3 | LOC103091866 | uncharacterized LOC103091866 |
| KLRC4 | killer cell lectin like receptor C4 | SEMA6B | semaphorin 6B |
| NXPH1 | neurexophilin 1 | UNC5A | unc-5 netrin receptor A |
| MYRF | myelin regulatory factor | MYH15 | myosin heavy chain 15 |
| RNF125 | ring finger protein 125 | CCND1 | cyclin D1 |
| GALNT13 | polypeptide N-acetylgalactosaminyltransferase 13 | NFASC | neurofascin |
| FGF12 | fibroblast growth factor 12 | LOC105371818 | uncharacterized LOC105371818 |
| DMRT2 | doublesex and mab-3 related transcription factor 2 | ADAP1 | ArfGAP with dual PH domains 1 |
| OMG | oligodendrocyte myelin glycoprotein | RINL | Ras and Rab interactor like |
| EVI2A | ecotropic viral integration site 2A | FRZB | frizzled-related protein |
| SLCO4A1 | solute carrier organic anion transporter family member 4A1 | TRIM67 | tripartite motif containing 67 |
| GPR45 | G protein-coupled receptor 45 | TSPAN15 | tetraspanin 15 |
| SYT6 | synaptotagmin 6 | DGKB | diacylglycerol kinase beta |
| SLC22A3 | solute carrier family 22 member 3 | ENPP5 | ectonucleotide pyrophosphatase/phosphodiesterase 5 (putative) |
| LOC100505797 | myosin heavy chain IB-like | STK32A | serine/threonine kinase 32A |
| WNT7B | Wnt family member 7B | SLC5A9 | solute carrier family 5 member 9 |
| MIR503HG | MIR503 host gene | KCNJ9 | potassium voltage-gated channel subfamily J member 9 |
| GRID2 | glutamate ionotropic receptor delta type subunit 2 | BCAN | brevican |
| TGFA | transforming growth factor alpha | TMEM100 | transmembrane protein 100 |
| GAL3ST1 | galactose-3-O-sulfotransferase 1 | DAAM2 | dishevelled associated activator of morphogenesis 2 |
| LOC107985505 | uncharacterized LOC107985505 | APCDD1 | APC down-regulated 1 |
| KCNS3 | potassium voltage-gated channel modifier subfamily S member 3 | NCKAP5 | NCK associated protein 5 |
| MATN1 | matrilin 1, cartilage matrix protein | MACROD2 | MACRO domain containing 2 |
| DCAF4L2 | DDB1 and CUL4 associated factor 4 like 2 | EPB41L2 | erythrocyte membrane protein band 4.1 like 2 |
| CTTNBP2 | cortactin binding protein 2 | NTNG1 | netrin G1 |
| CHRNA4 | cholinergic receptor nicotinic alpha 4 subunit | LOC107984006 | |
| GRID1 | glutamate ionotropic receptor delta type subunit 1 | LOC101926969 | uncharacterized LOC101926969 |
| PDE7B | phosphodiesterase 7B | LOC102724528 | uncharacterized LOC102724528 |
| OPCML | opioid binding protein/cell adhesion molecule like | PNPLA4 | patatin like phospholipase domain containing 4 |
| FAM89A | family with sequence similarity 89 member A | CDS1 | CDP-diacylglycerol synthase 1 |
| DACH2 | dachshund family transcription factor 2 | NTM | neurotrimin |
| KIAA1644 | KIAA1644 | AQP7P1 | aquaporin 7 pseudogene 1 |
| STK32B | serine/threonine kinase 32B | SERPINE2 | serpin family E member 2 |
| LINC01170 | long intergenic non-protein coding RNA 1170 | CDH10 | cadherin 10 |
| UBE2E2 | ubiquitin conjugating enzyme E2 E2 | LOC101927359 | uncharacterized LOC101927359 |
| LOC107984008 | | CALB1 | calbindin 1 |
| SLC35F3 | solute carrier family 35 member F3 | MPZ | myelin protein zero |
| HOXA2 | homeobox A2 | MSX1 | msh homeobox 1 |
| MDGA2 | MAM domain containing glycosylphosphatidylinositol anchor 2 | PDE4B | phosphodiesterase 4B |
| DSCAM | DS cell adhesion molecule | STAMBPL1 | STAM binding protein like 1 |
| SLC1A1 | solute carrier family 1 member 1 | HEY2 | hes related family bHLH transcription factor with YRPW motif 2 |
| ARFGEF3 | ARFGEF family member 3 | PLCL1 | phospholipase C like 1 |

TABLE 3-continued

Genes Downregulated in HD-derived hGPCS Compared to Controls

| | | | |
|---|---|---|---|
| LOC100507460 | uncharacterized LOC100507460 | PNMA3 | paraneoplastic Ma antigen 3 |
| MNX1 | motor neuron and pancreas homeobox 1 | LOC101927905 | |
| HOXA-AS2 | HOXA cluster antisense RNA 2 | CKMT1A | creatine kinase, mitochondrial 1B |
| LINC00320 | long intergenic non-protein coding RNA 320 | PDE4A | phosphodiesterase 4A |
| MYO7B | myosin VIIB | DEPTOR | DEP domain containing MTOR interacting protein |
| C1orf94 | chromosome 1 open reading frame 94 | KIFC3 | kinesin family member C3 |
| LINC00643 | long intergenic non-protein coding RNA 643 | CKMT1B | creatine kinase, mitochondrial 1B |
| TIMP4 | TIMP metallopeptidase inhibitor 4 | TUB | tubby bipartite transcription factor |
| GHR | growth hormone receptor | NECAB2 | N-terminal EF-hand calcium binding protein 2 |
| DPP10 | dipeptidyl peptidase like 10 | LOC100506114 | uncharacterized LOC100506114 |
| RAPGEF4 | Rap guanine nucleotide exchange factor 4 | GREB1L | growth regulation by estrogen in breast cancer 1 like |
| CMTM5 | CKLF like MARVEL transmembrane domain containing 5 | LOC107987002 | |
| ELFN2 | extracellular leucine rich repeat and fibronectin type III domain containing 2 | ARHGAP6 | Rho GTPase activating protein 6 |
| NBEAP2 | | ARL4A | ADP ribosylation factor like GTPase 4A |
| WFDC1 | WAP four-disulfide core domain 1 | NEURL1 | neuralized E3 ubiquitin protein ligase 1 |
| EN1 | engrailed homeobox 1 | CGREF1 | cell growth regulator with EF-hand domain 1 |
| MATK | megakaryocyte-associated tyrosine kinase | STXBP5-AS1 | STXBP5 antisense RNA 1 |
| ADGRB1 | adhesion G protein-coupled receptor B1 | NRG2 | neuregulin 2 |
| LOC105375304 | uncharacterized LOC105375304 | SOX13 | SRY-box 13 |
| ADAMTS17 | ADAM metallopeptidase with thrombospondin type 1 motif 17 | PKDCC | protein kinase domain containing, cytoplasmic |
| SIX6 | SIX homeobox 6 | CFAP52 | cilia and flagella associated protein 52 |
| SLC8A3 | solute carrier family 8 member A3 | NKAIN4 | sodium/potassium transporting ATPase interacting 4 |
| EPB41L4B | erythrocyte membrane protein band 4.1 like 4B | S1PR2 | sphingosine-1-phosphate receptor 2 |
| AFAP1L2 | actin filament associated protein 1 like 2 | RGMB-AS1 | RGMB antisense RNA 1 |
| OLIG2 | oligodendrocyte transcription factor 2 | PIK3R1 | phosphoinositide-3-kinase regulatory subunit 1 |
| LOC100130587 | uncharacterized LOC100130587 | EGFEM1P | EGF like and EMI domain containing 1, pseudogene |
| RIPPLY2 | ripply transcriptional repressor 2 | ETNK2 | ethanolamine kinase 2 |
| MUM1L1 | MUM1 like 1 | IRX2 | iroquois homeobox 2 |
| ETNPPL | ethanolamine-phosphate phospholyase | SCD5 | stearoyl-CoA desaturase 5 |
| PLD1 | phospholipase D1 | FRMPD2 | FERM and PDZ domain containing 2 |
| HOTAIRM1 | HOXA transcript antisense RNA, myeloid-specific 1 | ENPP4 | ectonucleotide pyrophosphatase/phosphodiesterase 4 (putative) |
| SUSD4 | sushi domain containing 4 | PKNOX2 | PBX/knotted 1 homeobox 2 |
| SGK1 | serum/glucocorticoid regulated kinase 1 | DOCK6 | dedicator of cytokinesis 6 |
| BMP8B | bone morphogenetic protein 8b | LOC646588 | uncharacterized LOC646588 |
| GALNT9 | polypeptide N acetylgalactosaminyltransferase 9 | MYC | MYC proto-oncogene, bHLH transcription factor |
| PTGER3 | prostaglandin E receptor 3 | MIR4697HG | MIR4697 host gene |
| LGI3 | leucine rich repeat LGI family member 3 | KLHL32 | kelch like family member 32 |
| PHF24 | PHD finger protein 24 | PLEKHA6 | pleckstrin homology domain containing A6 |
| DPP10-AS1 | DPP10 antisense RNA 1 | FLJ16779 | uncharacterized LOC100192386 |
| SLC2A13 | solute carrier family 2 member 13 | EHD3 | EH domain containing 3 |
| TBX2 | T-box 2 | USP54 | ubiquitin specific peptidase 54 |
| PRIMA1 | proline rich membrane anchor 1 | RHBDF1 | rhomboid 5 homolog 1 |
| PPARGC1B | PPARG coactivator 1 beta | RNF144A | ring finger protein 144A |
| HOXA1 | homeobox A1 | SIX4 | SIX homeobox 4 |
| SLITRK2 | SLIT and NTRK like family member 2 | LOC100422473 | |
| RNF144B | ring finger protein 144B | PRKCQ | protein kinase C theta |
| NEFM | neurofilament medium | SNAP91 | synaptosome associated protein 91 |
| SHISA7 | shisa family member 7 | ZCCHC24 | zinc finger CCHC-type containing 24 |
| LINGO1 | leucine rich repeat and Ig domain containing 1 | DUSP15 | dual specificity phosphatase 15 |
| LOC105378180 | uncharacterized LOC105378180 | RGS9 | regulator of G protein signaling 9 |

TABLE 3-continued

Genes Downregulated in HD-derived hGPCS Compared to Controls

| | | | |
|---|---|---|---|
| TF | transferrin | DCDC5 | doublecortin domain containing 1 |
| LOC105378516 | uncharacterized LOC105378516 | TCF7L2 | transcription factor 7 like 2 |
| CACNA1A | calcium voltage-gated channel subunit alpha1 A | NTRK3 | neurotrophic receptor tyrosine kinase 3 |
| LRRC4C | leucine rich repeat containing 4C | LOC100996643 | monofunctional C1-tetrahydrofolate synthase, mitochondrial-like |
| GRIK4 | glutamate ionotropic receptor kainate type subunit 4 | CGN | cingulin |
| KANK1 | KN motif and ankyrin repeat domains 1 | NOVA1 | NOVA alternative splicing regulator 1 |
| SERPINI1 | serpin family I member 1 | DOCK9 | dedicator of cytokinesis 9 |
| SNX10 | sorting nexin 10 | ADGRA1 | adhesion G protein-coupled receptor A1 |
| LOC101928216 | uncharacterized LOC101928216 | MYLIP | myosin regulatory light chain interacting protein |
| HAS2-AS1 | HAS2 antisense RNA 1 | RTKN | rhotekin |
| SULF2 | sulfatase 2 | BCL6 | B-cell CLL/lymphoma 6 |
| ACSL6 | acyl-CoA synthetase long-chain family member 6 | KCNQ1OT1 | KCNQ1 opposite strand/antisense transcript 1 (non-protein coding) |
| CFAP47 | cilia and flagella associated protein 47 | PCSK6 | proprotein convertase subtilisin/kexin type 6 |
| FGF14 | fibroblast growth factor 14 | LOC101928383 | uncharacterized LOC101928383 |
| VAV3 | vav guanine nucleotide exchange factor 3 | NCDN | neurochondrin |
| PTPRO | protein tyrosine phosphatase, receptor type O | ST3GAL6 | ST3 beta-galactoside alpha-2,3-sialyltransferase 6 |
| SYNDIG1 | synapse differentiation inducing 1 | SLC9A7 | solute carrier family 9 member A7 |
| NALCN | sodium leak channel, non-selective | HCN2 | hyperpolarization activated cyclic nucleotide gated potassium channel 2 |
| NID2 | nidogen 2 | FAM19A5 | family with sequence similarity 19 member A5, C-C motif chemokine like |
| ASTN2 | astrotactin 2 | CAMK2A | calcium/calmodulin dependent protein kinase II alpha |
| CSMD2 | CUB and Sushi multiple domains 2 | LOC101929959 | ribosome biogenesis protein BMS1 homolog |
| DPP6 | dipeptidyl peptidase like 6 | KLHL29 | kelch like family member 29 |
| BMP2 | bone morphogenetic protein 2 | CACNA1G | calcium voltage-gated channel subunit alpha1 G |
| DMGDH | dimethylglycine dehydrogenase | C2orf72 | chromosome 2 open reading frame 72 |
| MYRFL | myelin regulatory factor-like | KIF13A | kinesin family member 13A |
| ABCA4 | ATP binding cassette subfamily A member 4 | PPFIA3 | PTPRF interacting protein alpha 3 |
| HSPB8 | heat shock protein family B (small) member 8 | GJC2 | gap junction protein gamma 2 |
| GRIA2 | glutamate ionotropic receptor AMPA type subunit 2 | SNPH | syntaphilin |
| ETS2 | ETS proto-oncogene 2, transcription factor | BMS1P10 | BMS1, ribosome biogenesis factor pseudogene 10 |
| LOC151174 | uncharacterized LOC151174 | LINC00888 | long intergenic non-protein coding RNA 888 |
| | | SFMBT2 | Scm-like with four mbt domains 2 |

Huntington's disease is an autosomal dominant neurodegenerative disease characterized by a relentlessly progressive movement disorder with devastating psychiatric and cognitive deterioration. Huntington's disease is associated with a consistent and severe atrophy of the neostriatum which is related to a marked loss of the GABAergic medium-sized spiny projection neurons, the major output neurons of the striatum. Huntington's disease is characterized by abnormally long CAG repeat expansions in the first exon of the Huntingtin gene ("HTT"). The encoded polyglutamine expansions of mutant huntingtin protein disrupt its normal functions and protein-protein interactions, ultimately yielding widespread neuropathology, most rapidly evident in the neostriatum.

As used herein, the term "glial cells" refers to a population of non-neuronal cells that provide support and nutrition, maintain homeostasis, either form myelin or promote myelination, and participate in signal transmission in the nervous system. "Glial cells" as used herein encompasses fully differentiated cells of the glial lineage, such as oligodendrocytes or astrocytes, and well as glial progenitor cells. Glial progenitor cells are cells having the potential to differentiate into cells of the glial lineage such as oligodendrocytes and astrocytes.

As used herein, "treating" or "treatment" refers to any indication of success in amelioration of an injury, pathology, or condition, including any objective or subjective parameter such as abatement; remission; diminishing of symptoms or making the injury, pathology, or condition more tolerable to the patient; slowing the rate of degeneration or decline; making the final point of degeneration less debilitating; or improving a subject's physical or mental well-being. The treatment or amelioration of symptoms can be based on objective or subjective parameters; including the results of a physical examination, neurological examination, and/or psychiatric evaluation. "Treating" includes the administration of glial progenitor cells to prevent or delay, to alleviate, or to arrest or inhibit development of the symptoms or conditions associated with the disease, condition or disorder. "Therapeutic effect" refers to the reduction, elimination, or prevention of the disease, symptoms of the disease, or side effects of a disease, condition or disorder in the subject. Treatment may be prophylactic (to prevent or delay the onset or worsening of the disease, condition or disorder, or to prevent the manifestation of clinical or subclinical symptoms thereof) or therapeutic suppression or alleviation of symptoms after the manifestation of the disease, condition or disorder.

Suitable subjects for treatment in accordance with the methods described herein include any mammalian subject having or at risk of having Huntington's disease. Exemplary mammalian subjects include humans, mice, rats, guinea pigs, and other small rodents, dogs, cats, sheep, goats, and monkeys. In one embodiment, the subject is human.

The one or more modulators for use in the methods described herein can be, without limitation, a peptide, nucleic acid molecule, or small molecule compound. The modulator may be, for example, a naturally occurring, semi-synthetic, or synthetic agent. For example, the modulator may be a drug that targets a specific function of one or more genes. In certain embodiments, the one or more modulators may be an antagonist or an agonist.

The modulators of the present invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions.

The modulators of the present invention may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these modulators may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 and 250 mg of active compound.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

These modulators may also be administered parenterally. Solutions or suspensions of these modulators can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The modulators of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

If modulation is to be achieved at the DNA level, this may be done using gene therapy to knock-out or disrupt the target gene. As used herein, a "knock-out" can be a gene knockdown or the gene can be knocked out by a mutation such as, a point mutation, an insertion, a deletion, a frameshift, or a missense mutation by techniques known in the art, including, but not limited to, retroviral gene transfer.

In one embodiment, the one or more modulators may repress the expression of one or more of the genes described herein via a zinc finger nuclease. Zinc-finger nucleases (ZFNs) are artificial restriction enzymes generated by fusing a zinc finger DNA-binding domain to a DNA-cleavage domain. Zinc finger domains can be engineered to target desired DNA sequences, which enable zinc-finger nucleases to target unique sequence within a complex genome (Urnov et al., "Genome Editing with Engineered Zinc Finger Nucleases," *Nat. Rev. Genet.* 11: 636-646 (2010), which is hereby incorporated by reference in its entirety). By taking advantage of endogenous DNA repair machinery, these reagents can be used to precisely alter the genomes of higher organisms.

The one or more modulators may also be a meganuclease and TAL effector nuclease (TALENs, Cellectis Bioresearch) (Joung & Sander, "TALENs: A Widely Applicable Technology for Targeted Genome Editing," *Nat. Rev. Mol. Cell Biol.* 14: 49-55 (2013), which is hereby incorporated by reference in its entirety). A TALEN® is composed of a TALE DNA binding domain for sequence-specific recognition fused to the catalytic domain of an endonuclease that introduces double strand breaks (DSB). The DNA binding domain of a TALEN® is capable of targeting with high precision a large recognition site (for instance 17 bp). Meganucleases are sequence-specific endonucleases, naturally occurring "DNA scissors", originating from a variety of single-celled organisms such as bacteria, yeast, algae and some plant organelles. Meganucleases have long recognition sites of between 12 and 30 base pairs. The recognition site of natural meganucleases can be modified in order to target native genomic DNA sequences (such as endogenous genes).

In another embodiment, the one or more modulators is a CRISPR-Cas9 guided nuclease (Wiedenheft et al., "RNA-Guided Genetic Silencing Systems in Bacteria and Archaea," *Nature* 482:331-338 (2012); Zhang et al., "Multiplex Genome Engineering Using CRISPR/Cas Systems," *Science* 339(6121): 819-23 (2013); and Gaj et al., "ZFN, TALEN, and CRISPR/Cas-based Methods for Genome Engineering," *Cell* 31(7):397-405 (2013), which are hereby incorporated by reference in their entirety). Like the TALENs and ZFNs, CRISPR-Cas9 interference is a genetic technique which allows for sequence-specific control of gene expression in prokaryotic and eukaryotic cells by guided nuclease double-stranded DNA cleavage. It is based on the bacterial immune system-derived CRISPR (clustered regularly interspaced palindromic repeats) pathway.

Modulation of the one or more genes described herein can also be carried out using antisense oligonucleotides (ASO). Suitable therapeutic ASOs for inhibition of one or more of the genes described herein include, without limitation, antisense RNAs, DNAs, RNA/DNA hybrids (e.g., gapmer), and chemical analogues thereof, e.g., morpholinos, peptide nucleic acid oligomer, ASOs comprised of locked nucleic acids. With the exception of RNA oligomers, PNAs, and morpholinos, all other antisense oligomers act in eukaryotic cells through the mechanism of RNase H-mediated target cleavage. PNAs and morpholinos bind complementary DNA and RNA targets with high affinity and specificity, and thus act through a simple steric blockade of the RNA translational machinery, and appear to be completely resistant to nuclease attack.

An "antisense oligomer" refers to an antisense molecule or anti-gene agent that comprises an oligomer of at least about 10 nucleotides in length. In embodiments an antisense oligomer comprises at least 15, 18, 20, 25, 30, 35, 40, or 50 nucleotides. Antisense approaches involve the design of oligonucleotides (either DNA, RNA, DNA/RNA, or chemically modified derivatives thereof) that are complementary to an RNA encoded by polynucleotide sequences of the genes identified herein. Antisense RNA may be introduced into a cell to inhibit translation or activity of a complementary mRNA by base pairing to it and physically obstructing its translation or its activity. This effect is therefore stoichiometric. Absolute complementarity, although preferred, is not required. A sequence "complementary" to a portion of an RNA, as referred to herein, means a sequence having sufficient complementarity to be able to hybridize with the RNA, forming a stable duplex. In the case of double stranded antisense polynucleotide sequences, a single strand of the duplex DNA may thus be tested, or triplex formation may be assayed. The ability to hybridize will depend on both the degree of complementarity and the length of the antisense polynucleotide sequence. Generally, the longer the hybridizing polynucleotide sequence, the more base mismatches with an RNA it may contain and still form a stable duplex (or triplex, as the case may be). One skilled in the art can ascertain a tolerable degree of mismatch by use of standard procedures to determine the melting point of the hybridized complex.

In one embodiment, the one or more modulators is an antisense oligonucleotide that specifically binds to and inhibits the functional expression of one or more genes described herein. For example, common modifications to an ASO to increase duplex stability include the incorporation of 5-methyl-dC, 2-amino-dA, locked nucleic acid, and/or peptide nucleic acid bases. Common modifications to enhance nuclease resistance include conversion of the normal phosphodiester linkages to phosphorothioate or phosphorodithioate linkages, or use of propyne analog bases, 2'-O-Methyl or 2'-O-Methyloxyethyl RNA bases.

RNA interference (RNAi) using small interfering RNA (siRNA) is another form of post-transcriptional gene silencing that can be utilized for modulating one or more genes in a subject as described herein.

Accordingly, in one embodiment, the one or more modulators is an siRNA. siRNAs are double stranded synthetic RNA molecules approximately 20-25 nucleotides in length with short 2-3 nucleotide 3' overhangs on both ends. The double stranded siRNA molecule represents the sense and anti-sense strand of a portion of the target mRNA molecule. siRNA molecules are typically designed to target a region of the mRNA target approximately 50-100 nucleotides downstream from the start codon. The siRNAs of the invention can comprise partially purified RNA, substantially pure RNA, synthetic RNA, or recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siRNA or to one or more internal nucleotides of the siRNA, including modifications that make the siRNA resistant to nuclease digestion. Upon introduction into a cell, the siRNA complex triggers the endogenous RNAi pathway, resulting in the cleavage and degradation of the target mRNA molecule. Various improvements of siRNA compositions, such as the incorporation of modified nucleosides or motifs into one or both strands of the siRNA molecule to enhance stability, specificity, and efficacy, have been described and are suitable for use in accordance with this aspect of the invention (see e.g., WO2004/015107 to Giese et al.; WO2003/070918 to McSwiggen et al.; WO1998/39352 to Imanishi et al.; U.S. Patent Application Publication No. 2002/0068708 to Jesper et al.; U.S. Patent Application Publication No. 2002/0147332 to Kaneko et al; U.S. Patent Application Publication No. 2008/0119427 to Bhat et al., which are hereby incorporated by reference in their entirety).

In another embodiment, the one or more modulators comprises endoribonuclease-prepared siRNAs (esiRNA), which comprise a mixture of siRNA oligonucleotides formed from the cleavage of long double stranded RNA with an endoribonuclease (e.g., RNase III or dicer). Digestion of synthetic long double stranded RNA produces short overlapping fragments of siRNAs with a length of between 18-25 bases that all target the same mRNA sequence. The complex mixture of many different siRNAs all targeting the same mRNA sequence leads to increased silencing efficacy. The use of esiRNA technology to target long non-coding RNA has been described in the art (Theis et al., "Targeting Human Long Noncoding Transcripts by Endoribonuclease-Prepared siRNAs," *J. Biomol. Screen* 20(8):1018-1026 (2015), which is hereby incorporated by reference in its entirety).

The one or more modulators may also be a short or small hairpin RNA. Short or small hairpin RNA molecules are similar to siRNA molecules in function, but comprise longer RNA sequences that make a tight hairpin turn. shRNA is cleaved by cellular machinery into siRNA and gene expression is silenced via the cellular RNA interference pathway.

Nucleic acid aptamers that specifically bind to one or more of the genes described herein are also useful in the methods of the present invention. Nucleic acid aptamers are single-stranded, partially single-stranded, partially double-stranded, or double-stranded nucleotide sequences, advantageously a replicatable nucleotide sequence, capable of specifically recognizing a selected non-oligonucleotide molecule or group of molecules by a mechanism other than Watson-Crick base pairing or triplex formation. Aptamers include, without limitation, defined sequence segments and sequences comprising nucleotides, ribonucleotides, deoxyribonucleotides, nucleotide analogs, modified nucleotides, and nucleotides comprising backbone modifications, branchpoints, and non-nucleotide residues, groups, or bridges. Nucleic acid aptamers include partially and fully single-stranded and double-stranded nucleotide molecules and sequences; synthetic RNA, DNA, and chimeric nucleotides; hybrids; duplexes; heteroduplexes; and any ribonucleotide, deoxyribonucleotide, or chimeric counterpart thereof and/or corresponding complementary sequence, promoter, or primer-annealing sequence needed to amplify, transcribe, or replicate all or part of the aptamer molecule or sequence.

In the embodiments described supra, the one or more modulators may be packaged in a suitable delivery vehicle or carrier for delivery to the subject. Suitable delivery vehicles include, but are not limited to viruses, virus-like particles, bacteria, bacteriophages, biodegradable microspheres, microparticles, nanoparticles, exosomes, liposomes, collagen minipellets, and cochleates. These and other biological gene delivery vehicles are well known to those of skill in the art (see e.g., Seow and Wood, "Biological Gene Delivery Vehicles: Beyond Viral Vectors," *Mol. Therapy* 17(5):767-777(2009), which is hereby incorporated by reference in its entirety).

In one embodiment, the modulator is packaged into a therapeutic expression vector to facilitate delivery. Suitable expression vectors are well known in the art and include, without limitation, viral vectors such as adenovirus vectors, adeno-associated virus vectors, retrovirus vectors, lentivirus vectors, or herpes virus vectors. The viral vectors or other suitable expression vectors comprise sequences encoding the inhibitory nucleic acid molecule (e.g., siRNA, ASO, etc.) of the invention and any suitable promoter for expressing the inhibitory sequences. Suitable promoters include, for example, and without limitation, the U6 or HI RNA pol III promoter sequences and the cytomegalovirus promoter. Selection of other suitable promoters is within the skill in the art. The expression vectors may also comprise inducible or regulatable promoters for expression of the inhibitory nucleic acid molecules in a tissue or cell-specific manner.

Gene therapy vectors carrying the therapeutic inhibitory nucleic acid molecule are administered to a subject by, for example, intravenous injection, local administration (U.S. Pat. No. 5,328,470 to Nabel et al., which is hereby incorporated by reference in its entirety) or by stereotactic injection (see e.g., Chen et al. "Gene Therapy for Brain Tumors: Regression of Experimental Gliomas by Adenovirus Mediated Gene Transfer In Vivo," *Proc. Nat'l. Acad. Sci. USA* 91:3054-3057 (1994), which is hereby incorporated by reference in its entirety). The pharmaceutical preparation of the therapeutic vector can include the therapeutic vector in an acceptable diluent, or can comprise a slow release matrix in which the therapeutic delivery vehicle is imbedded. Alternatively, where the complete therapeutic delivery vector can be produced intact from recombinant cells, e.g., retroviral vectors, the pharmaceutical preparation can include one or more cells which produce the therapeutic delivery system. Gene therapy vectors typically utilize constitutive regulatory elements which are responsive to endogenous transcriptions factors.

Another suitable approach for the delivery of the modulators of the present disclosure, involves the use of liposome delivery vehicles or nanoparticle delivery vehicles.

In one embodiment, the pharmaceutical composition or formulation containing an inhibitory nucleic acid molecule (e.g., siRNA molecule) is encapsulated in a lipid formulation to form a nucleic acid-lipid particle as described in Semple et al., "Rational Design of Cationic Lipids for siRNA Delivery," *Nature Biotech*. 28:172-176 (2010) and WO2011/034798 to Bumcrot et al., WO2009/111658 to Bumcrot et al., and WO2010/105209 to Bumcrot et al., which are hereby incorporated by reference in their entirety. Other cationic lipid carriers suitable for the delivery of ASO include, without limitation, N-[1-(2,3-dioleoyloxy)propyl]-N,N,N-trimethylammonium chloride (DOTMA) and N-[1-(2,3-dioleoyloxy)propyl]-N,N,N-trimethylammonium methyl sulphate (DOTAP) (see Chan et al., "Antisense Oligonucleotides: From Design to Therapeutic Application," *Clin. Exp. Pharm. Physiol.* 33: 533-540 (2006), which is hereby incorporated by reference in its entirety).

In another embodiment of the present invention, the delivery vehicle is a nanoparticle. A variety of nanoparticle delivery vehicles are known in the art and are suitable for delivery of the modulators of the invention (see e.g., van Vlerken et al., "Multi-functional Polymeric Nanoparticles for Tumour-Targeted Drug Delivery," *Expert Opin. Drug Deliv.* 3(2):205-216 (2006), which is hereby incorporated by reference in its entirety). Suitable nanoparticles include, without limitation, poly(beta-amino esters) (Sawicki et al., "Nanoparticle Delivery of Suicide DNA for Epithelial Ovarian Cancer Cell Therapy," *Adv. Exp. Med. Biol.* 622:209-219 (2008), which is hereby incorporated by reference in its entirety), polyethylenimine-alt-poly(ethylene glycol) copolymers (Park et al., "Degradable Polyethylenimine-alt-Poly (ethylene glycol) Copolymers As Novel Gene Carriers," *J. Control Release* 105(3):367-80 (2005) and Park et al., "Intratumoral Administration of Anti-KITENIN shRNA-Loaded PEI-alt-PEG Nanoparticles Suppressed Colon Carcinoma Established Subcutaneously in Mice," *J Nanosci. Nanotechnology* 10(5):3280-3 (2010), which are hereby incorporated by reference in their entirety), poly(d,1-lactide-coglycolide) (Chan et al., "Antisense Oligonucleotides: From Design to Therapeutic Application," *Clin. Exp. Pharm. Physiol.* 33: 533-540 (2006), which is hereby incorporated by reference in its entirety), and liposome-entrapped siRNA nanoparticles (Kenny et al., "Novel Multifunctional Nanoparticle Mediates siRNA Tumor Delivery, Visualization and Therapeutic Tumor Reduction In Vivo," *J. Control Release* 149(2): 111-116 (2011), which is hereby incorporated by reference in its entirety). Other nanoparticle delivery vehicles suitable for use in the present invention include microcapsule nanotube devices disclosed in U.S. Patent Publication No. 2010/0215724 to Prakash et al., which is hereby incorporated by reference in its entirety.

In another embodiment, the pharmaceutical composition is contained in a liposome delivery vehicle. The term "liposome" means a vesicle composed of amphiphilic lipids arranged in a spherical bilayer or bilayers. Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

Several advantages of liposomes include: their biocompatibility and biodegradability, incorporation of a wide range of water and lipid soluble drugs; and they afford protection to encapsulated drugs from metabolism and degradation. Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Methods for preparing liposomes for use in the present invention include those disclosed in Bangham et al., "Diffusion of Univalent Ions Across the Lamellae of Swollen Phospholipids," *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau et al.; and U.S. Pat. No. 5,059,421 to Loughrey et al., which are hereby incorporated by reference in their entirety.

In one aspect, one or more modulators of a glial cell differentiation regulation gene selected from the group consisting of BMP2, LINGO1, MAG, NKX2-2, NR2E1, NTRK3, OLIG2, SERPINE2, SIRT2, and TCF7L2, or a protein encoded therefrom, are administered to the selected subject under conditions effective to treat or inhibit onset of Huntington's disease in the subject.

Exemplary modulators for these genes include, without limitation: the synthetic non-peptidyl small molecule, Hh-Ag 1.1, and related molecules Hh-Ag 1.2, Hh-Ag 1.3, Hh-Ag 1.4, and Hh Ag 1.5, which effect the Hedgehog signaling pathway (Frank-Kamenetsky et al., "Small-molecule Modulators of Hedgehog Signaling: Identification and Characterization of Smoothened Agonists and Antagonists," *J. Biol.* 1(2):10 (2002), which is hereby incorporated by reference in its entirety and agonists of the Wnt Signaling pathway including, without limitation, 2-amino-4-(3,4-(methylenedioxy)benzylamino)-6-(3-methoxyphenyl)pyrimidine (2-AMBMP), curcumin, and Simvastatin, as described in Blagodatski et al., "Targeting the Wnt Pathways for Therapies," *Mol. Cell Ther.* 2:28 (2014), which is hereby incorporated by reference in its entirety; Opicinumab; GSK-249320; sodium lauryl sufate; repaglinide; altiratinib; chembl2007421; PLX-3397; radicicol; thyroxine; entrectinib; LOXO-101; CEP-2563; lestaurtinib; PLX-7486; AZD-6918; AZD-7451; midostaurin; and combinations thereof.

In another aspect, one or more modulators of a myelination-associated gene selected from the group consisting of FA2H, GAL3ST1, MAG, MBP, MYRF, NFASC, OLIG2, OMG, PLLP, POU3F2, SIRT2, SLC8A3, TCF7L2, TF, and UGT8, or a protein encoded therefrom, are administered to the selected subject under conditions effective to treat or inhibit onset of Huntington's disease in the subject.

Exemplary modulators for these genes include, without limitation: agonists of the Wnt Signaling pathway including, without limitation, 2-amino-4-(3,4-(methylenedioxy)benzylamino)-6-(3-methoxyphenyl)pyrimidine (2-AMBMP), curcumin, and Simvastatin, as described in Blagodatski et al., "Targeting the Wnt Pathways for Therapies," *Mol. Cell Ther.* 2:28 (2014), which is hereby incorporated by reference in its entirety; GSK-249320; sodium lauryl sulfate; Repaglinide; cyclosporine; interferon beta-1A; prednisone; quercetin; and rutin; and combinations thereof.

In yet another aspect, one or more modulators of an oligodendrocyte differentiation gene selected from the group consisting of FA2H, GLI3, LINGO1, MYRF, NKX2-2, OLIG1, OLIG2, OMG, SIRT2, SLC8A3, SOX10, and TCF7L2, or a protein encoded therefrom, are administered to the selected subject under conditions effective to treat or inhibit onset of Huntington's disease in the subject.

Exemplary modulators for these genes include, without limitation: the synthetic non-peptidyl small molecule, Hh-Ag 1.1, and related molecules Hh-Ag 1.2, Hh-Ag 1.3, Hh-Ag 1.4, and Hh Ag 1.5, which effect the Hedgehog signaling pathway (Frank-Kamenetsky et al., "Small-molecule Modulators of Hedgehog Signaling: Identification and Characterization of Smoothened Agonists and Antagonists," *J. Biol.* 1(2):10 (2002), which is hereby incorporated by reference in its entirety and agonists of the Wnt Signaling pathway including, without limitation, 2-amino-4-(3,4-(methylenedioxy)benzylamino)-6-(3-methoxyphenyl)pyrimidine (2-AMBMP), curcumin, and Simvastatin, as described in Blagodatski et al., "Targeting the Wnt Pathways for Therapies," *Mol. Cell Ther.* 2:28 (2014), which is hereby incorporated by reference in its entirety; Opicinumab; sodium lauryl sulfate; Repaglinide; Vemurafenib; and combinations thereof.

In a further aspect, one or more modulators of a gliogenesis regulation gene selected from the group consisting of BMP2, LINGO1, MAG, MYC, NKX2-2, NR2E1, NTRK3, OLIG2, SERPINE2, SIRT2, SOX10, TCF7L2, TF, and ZCCHC24, or a protein encoded therefrom, are administered to the selected subject under conditions effective to treat or inhibit onset of Huntington's disease in the subject.

Exemplary modulators for these genes include, without limitation: the synthetic non-peptidyl small molecule, Hh-Ag 1.1, and related molecules Hh-Ag 1.2, Hh-Ag 1.3, Hh-Ag 1.4, and Hh Ag 1.5, which effect the Hedgehog signaling pathway (Frank-Kamenetsky et al., "Small-molecule Modulators of Hedgehog Signaling: Identification and Characterization of Smoothened Agonists and Antagonists," *J. Biol.* 1(2):10 (2002), which is hereby incorporated by reference in its entirety and agonists of the Wnt Signaling pathway including, without limitation, 2-amino-4-(3,4-(methylenedioxy)benzylamino)-6-(3-methoxyphenyl)pyrimidine (2-AMBMP), curcumin, and Simvastatin, as described in Blagodatski et al., "Targeting the Wnt Pathways for Therapies," *Mol. Cell Ther.* 2:28 (2014), which is hereby incorporated by reference in its entirety; Opicinumab; GSK-249320; sodium lauryl sulfate; Vemurafenib; Repaglinide; Nadroparin calcium; 4'-hydroxytamoxifen; Azacitidine; Thioguanine; Acivin; Adozelesin; Amifostine; Aminopterin; antibiotic; Bizelesin; Bromocriptin; Bryostatin; Calcitriol; Diethyl stilbestrol; Elsamitrucin; Estrone; folic acid; glutamine; Hypoxanthine; Imatinib; Cilmostin; melatonin; methylprednisolone; N-methyl-n-nitrosurea; Novobiocin; Chembl35482; phorbol myristate acetate; prednisone; Quinapril; Vorinostat; Sulindac; thrombin; thyrotropin; sodium beta-nicotinamide adenine dinucleotide phosphate; troglitazone; verapamil; Chembl100014; Chembl1213492; chorionic gonadotropin; perillyl alcohol; AMG-900; Alisertib; Dinaciclib; Roniciclib; Temozolomide; Prexasertib; altiratinib; chemb12007421; PLX-3397; radicicol; thyroxine; entrectinib; LOXO-101; CEP-2563; lestaurtinib; PLX-7486; AZD-6918; AZD-7451; midostaurin; and combinations thereof.

In another aspect of the present disclosure one or more modulators of a neuron ensheathment gene selected from the group consisting of FA2H, GAL3ST1, MAG, MBP, MYRF, NFASC, OLIG2, OMG, PLLP, POU3F2, SIRT2, SLC8A3, TCF7L2, TF, and UGT8, or a protein encoded therefrom, are administered to the selected subject under conditions effective to treat or inhibit onset of Huntington's disease in the subject.

Exemplary modulators for these genes include, without limitation: agonists of the Wnt Signaling pathway including, without limitation, 2-amino-4-(3,4-(methylenedioxy)benzylamino)-6-(3-methoxyphenyl)pyrimidine (2-AMBMP), curcumin, and Simvastatin, as described in Blagodatski et al., "Targeting the Wnt Pathways for Therapies," *Mol. Cell Ther.* 2:28 (2014), which is hereby incorporated by reference in its entirety; GSK-249320; cyclosporine; interferon beta-1A; prednisone; quercetin; rutin; sodium lauryl sulfate; Repaglinide; and combinations thereof.

In another aspect one or more modulators of an axon guidance gene selected from the group consisting of ALCAM, BCL11B, DSCAM, FOXD1, GAS1, GLI3, HOXA1, HOXA2, MNX1, NFASC, PLXNC1, PRKCQ, PTPRO, ROBO2, SEMA6B, UNC5A, VAX1, and WNT7B, or a protein encoded therefrom, are administered to the selected subject under conditions effective to treat or inhibit onset of Huntington's disease in the subject.

Exemplary modulators for these genes include, without limitation, agonists of the Wnt Signaling pathway including, without limitation, 2-amino-4-(3,4-(methylenedioxy)benzylamino)-6-(3-methoxyphenyl)pyrimidine (2-AMBMP), curcumin, and Simvastatin, as described in Blagodatski et al., "Targeting the Wnt Pathways for Therapies," *Mol. Cell Ther.* 2:28 (2014), which is hereby incorporated by reference in its entirety); fluorouracil; CEP-2563; staurosporine; Chembl369507; Dexfosfoserine; Ticlopidine; GSK-690693; sotrastaurin; (7S)-Hydroxyl-staurosporine; midostaurin; quercetin; bryostatin; sotrastaurin acetate; ingenol mebutate; carboplatin; paclitaxel; and combinations thereof.

In a further aspect one or more modulators of a neuron projection guidance gene selected from the group consisting of ALCAM, BCL11B, DSCAM, FOXD1, GAS1, GLI3, HOXA1, HOXA2, MNX1, NFASC, PLXNC1, PRKCQ, PTPRO, ROBO2, SEMA6B, UNC5A, VAX1, and WNT7B, or a protein encoded therefrom, are administered to the selected subject under conditions effective to treat or inhibit onset of Huntington's disease in the subject.

Exemplary modulators for these genes include, without limitation: agonists of the Wnt Signaling pathway including, without limitation, 2-amino-4-(3,4-(methylenedioxy)benzylamino)-6-(3-methoxyphenyl)pyrimidine (2-AMBMP), curcumin, and Simvastatin, as described in Blagodatski et al., "Targeting the Wnt Pathways for Therapies," *Mol. Cell Ther.* 2:28 (2014), which is hereby incorporated by reference in its entirety; fluorouracil; CEP-2563; staurosporine; Chembl369507; dexfosfoserine; Ticlopidine; GSK-690693; sotrastaurin; (7S)-Hydroxyl-staurosporine; midostaurin; quercetin; bryostatin; sotrastaurin acetate; ingenol mebutate; carboplatin; paclitaxel; and combinations thereof.

In another aspect one or more modulators of an axonogenesis gene selected from the group consisting of ADGRB1, ALCAM, BCL11B, CACNA1A, DSCAM, FOXD1, GAS1, GLI3, HOXA1, HOXA2, LINGO1, LRRC4C, MAG, MBP, MNX1, NFASC, NR2E1, NTNG1, NTRK3, OMG, PLXNC1, POU3F2, PRKCQ, PTPRO, ROBO2, SEMA6B, SLITRK2, SLITRK3, SNAP91, UNC5A, VAX1, and WNT7B, or a protein encoded therefrom, are administered to the selected subject under conditions effective to treat or inhibit onset of Huntington's disease in the subject.

Exemplary modulators for these genes include, without limitation: agonists of the Wnt Signaling pathway including, without limitation, 2-amino-4-(3,4-(methylenedioxy)benzylamino)-6-(3-methoxyphenyl)pyrimidine (2-AMBMP), curcumin, and Simvastatin, as described in Blagodatski et al., "Targeting the Wnt Pathways for Therapies," *Mol. Cell Ther.* 2:28 (2014), which is hereby incorporated by reference in its entirety; Opicinumab; GSK-249320; cyclosporine; interferon beta-1A; prednisone; quercetin; rutin; fluorouracil; CEP-2563; staurosporine; Chembl369507; Dexfosfoserine; ticlopidine; GSK-690693; sotrastaurin; (7S)-Hydroxyl-staurosporine; midostaurin; bryostatin; sotrastaurin acetate; ingenol mebutate; carboplatin; paclitaxel; pregabalin; verapamil; bepridil; celecoxib; nisoldipine; gabapentin; gabapentin enacarbil; elpetrigine; atagabalin; bepridil hydrochloride; imagabalin; altiratinib; chembl2007421; PLX-3397; radicicola; thyroxine; entrectinib; Loxo-101; CEP-2563; lestaurtinib; PLX-7486; AZD-6918; AZD-7451; and combinations thereof.

In another aspect one or more modulators of an axon development gene selected from the group consisting of ADGRB1, ALCAM, BCL11B, CACNA1A, DSCAM, FOXD1, GAS1, GLI3, HOXA1, HOXA2, LINGO1, LRRC4C, MAG, MBP, MNX1, NEFM, NFASC, NR2E1, NTNG1, NTRK3, OMG, PLXNC1, POU3F2, PRKCQ, PTPRO, ROBO2, RTN4RL2, SEMA6B, SLITRK2, SLITRK3, SNAP91, UNC5A, VAX1, and WNT7B, or a protein encoded therefrom, are administered to the selected subject under conditions effective to treat or inhibit onset of Huntington's disease in the subject.

Exemplary modulators for these genes include, without limitation: agonists of the Wnt Signaling pathway including, without limitation, 2-amino-4-(3,4-(methylenedioxy)benzylamino)-6-(3-methoxyphenyl)pyrimidine (2-AMBMP), curcumin, and Simvastatin, as described in Blagodatski et al., "Targeting the Wnt Pathways for Therapies," *Mol. Cell Ther.* 2:28 (2014), which is hereby incorporated by reference in its entirety; Opicinumab; dexfosfoserine; fluorouracil; CEP-2563; staurosporine; Chembl369507; GSK-249320; Ticlopidine; GSK-690693; sotrastaurin; (7S)-Hydroxyl-staurosporine; midostaurin; quercetin; bryostatin; sotrastaurin acetate; and ingenol mebutate; carboplatin; paclitaxel; pregabalin; verapamil; bepridil; celecoxib; nisoldipine; gabapentin; gabapentin enacarbil; elpetrigine; atagabalin; bepridil hydrochloride; imagabalin; altiratinib; chemb12007421; PLX-3397; radicicola; thyroxine; entrectinib; Loxo-101; CEP-2563; lestaurtinib; PLX-7486; AZD-6918; AZD-7451; cyclosporine; interferon beta-1A; prednisone; rutin; and combinations thereof.

In a further aspect of the present disclosure one or more modulators of a cell projection morphogenesis gene selected from the group consisting of ADGRB1, ALCAM, BCL11B, CACNA1A, CAMK2A, DSCAM, EHD3, FOXD1, GAS1, GLI3, HOXA1, HOXA2, KANK1, LINGO1, LRRC4C, MAG, MBP, MNX1, NEDD4L, NEURL1, NFASC, NR2E1, NTNG1, NTRK3, OMG, PCDH15, PLXNC1, POU3F2, PRKCQ, PTPRO, ROBO2, SEMA6B, SGK1, SLITRK2, SLITRK3, SNAP91, SNX10, UGT8, UNC5A, VAX1, and WNT7B, or protein encoded therefrom, are administered to the selected subject under conditions effective to treat or inhibit onset of Huntington's disease in the subject.

Exemplary modulators for these genes include, without limitation: agonists of the Wnt Signaling pathway including, without limitation, 2-amino-4-(3,4-(methylenedioxy)benzylamino)-6-(3-methoxyphenyl)pyrimidine (2-AMBMP), curcumin, and Simvastatin, as described in Blagodatski et al., "Targeting the Wnt Pathways for Therapies," *Mol. Cell Ther.* 2:28 (2014), which is hereby incorporated by reference in its entirety; Opicinumab; GSK-249320; cyclosporine; interferon beta-1A; prednisone; quercetin; rutin; dexfosfoserine; fluorouracil; CEP-2563; staurosporine; Chembl369507; ticlopidine; GSK-690693; sotrastaurin; (7S)-Hydroxyl-staurosporine; midostaurin; bryostatin; sotrastaurin acetate; and ingenol mebutate; carboplatin; paclitaxel; pregabalin; verapamil; bepridil; celecoxib; nisoldipine; gabapentin; gabapentin enacarbil; elpetrigine; atagabalin; bepridil hydrochloride; imagabalin; altiratinib; Chembl2007421; PLX-3397; radicicola; thyroxine; entrectinib; Loxo-101; CEP-2563; lestaurtinib; PLX-7486; AZD-6918; AZD-7451; hydrochlorothiazide; chemb1549906; chemb1550795; sodium chloride; GSK-650394; and combinations thereof.

In another aspect of the present disclosure one or more modulators of a synapse structure or activity regulation gene selected from the group consisting of ADGRB1, ADGRL3, BCAN, CALB1, CAMK2A, FGF14, LRRTIM1, NCDN, NETO1, NEURL1, NR2E1, NTRK3, PPFIA3, ROBO2, SERPINE2, SHISA7, SIX4, SLC8A3, SLITRK2, SLITRK3, and SYNDIG1, or protein encoded therefrom, are administered to the selected subject under conditions effective to treat or inhibit onset of Huntington's disease in the subject.

Exemplary modulators for these genes include, without limitation: dexfosfoserine; altiratinib; chemb12007421; PLX-3397; radicicola; thyroxine; entrectinib; Loxo-101; CEP-2563; lestaurtinib; PLX-7486; AZD-6918; AZD-7451; midostaurin; and combinations thereof.

In a further aspect one or more modulators of a synaptic signaling pathway gene selected from the group consisting of BCAN, CACNA1A, CACNA1G, CALB1, CAMK2A, CHRNA4, FGF12, FGF14, GRIA2, GRIA4, GRID2, GRIK4, KCND2, LRRTM1, MBP, MPZ, NCDN, NETO1, NEURL1, NOVA1, NR2E1, P2RX7, PDE7B, PLCL1, PPFIA3, RAPGEF4, RGS8, RIT2, S1PR2, SERPINE2, SHISA7, SLC18A1, SLC1A1, SLC1A2, SLC8A3, SNAP91, SNPH, and SYT6, or protein encoded therefrom, are administered to the selected subject under conditions effective to treat or inhibit onset of Huntington's disease in the subject.

Exemplary modulators for these genes include, without limitation: pregabalin; verapamil; bepridil; celecoxib; nisoldipine; gabapentin; gabapentin enacarbil; elpetrigine; atagabalin; bepridil hydrochloride; imagabalin; cyclosporine; interferon beta-1A; prednisone; quercetin; rutin; nicotine polacrilex; talbutal; butabarbital; butalbital; secobarbital; metharbital; thiopental; primidone; mephobarbital; phenobarbital; varenicline; amobarbital; aprobarbital; butethal; heptabarbital; hexobarbital; barbital; pozanicline; cytisine; rivanicline; epibatidine; chembl1876219; chembl3103988; atracurium; chembl490153; hexamethonium; chembl407217; TC-2216; ABT-560; ispronicline; sofinicline; TC-6499; AZD1446; CP-601927; dexmecamylamine; nicotine; varenicline tartrate; benztropine mesylate; pentolinium; azd0328; bradanicline; pentobarbital; chembl1201135; dexefaroxan; mecamylamine (chemb1267936); dianicline; altinicline; trimethaphan; oleic acid; tebanicline tosylate; mibampator; butethal; (r,s)-ampa; chembl123132; aniracetam; chembl136800; chembl1255648; cyclothiazide; chemb177862; chembl334920; chembl1097939; piracetam; chemb1320642; chembl265301; gyki-52466; nbqx; chembl222418; tezampanel; (s)-ampa; chemb1594840; chembl121915; quisqualate; chembl337577; chembl27130; dnqx; chembl333964; (s)-willardiine; chemb128472; talampanel; perampanel; irampanel; CX1739; dasolampanel; becampanel; farampator; mk-8777; zonampanel; pentobarbital; pf-04958242; Selurampanel; dalfampridine; guanidine hydrochloride; tedisamil; nerispirdine; evt401; adenosine triphosphate; chembl335550; chelerythrine; acebutolol; moclobemide; ivermectin; chemb377219; chembl255787; methylclothiazide; chemb1550637; sodium orthovanadate; chembl2338352; benzonatate; GSK1482160; AZD9056, CE224535; dyphylline; chemb1484928; dipyridamole; flavoxate hydrochloride; pentoxifylline; quinacrine; chembl2313646; chembl570352; ozanimod; chembl225155; chemb11368758; fingolimod hydrochloride; amiselimod hydrochloride; reserpine; norepinephrine; chemb1126506; methamphetamine; ketanserin; tetrabenazine; L-glutamate; dihydrokainate; 2s,4r-4-methylglutamate; o-benzyl-1-serine; chemb11628669; and mesalamine; tezampanel; domoic acid; dysiherbaine; kainic acid; mesalamine; topiramate; aspartic acid; clozapine; alcohol; haloperidol; wortmannin; olanzapine; phorbol myristate acetate; risperidone; lidocaine; pregabalin; gabapentin enacarbil; mibefradil dihydrochloride; trimethadione; cinnarizine; ethosuximide; zonisamide; anandamide; mibefradil; chembl1684954; flunarizine; methsuximide; bepridil hydrochloride; gabapentin; phensuximide; paramethadione; atagabalin; celecoxib; imagabalin; and combinations thereof.

In another aspect one or more modulators of a synapse gene selected from the group consisting of ADGRB1, BCAN, BCAS1, CACNA1A, CALB1, CAMK2A, CHRNA4, CTTNBP2, DSCAM, GRIA2, GRID1, GRID2, GRIK4, HCN2, KCND2, LGI3, LRRC4C, LRRTM1, NETO1, NEURL1, NTM, P2RX7, PCDH15, PDE4B, PPFIA3, PRIMA1, PRKCQ, PTPRO, RAPGEF4, SERPINE2, SHISA7, SLC17A8, SLC18A1, SLC1A1, SLC1A2, SLC8A3, SNAP91, SNPH, SYNDIG1, and SYT6, or protein encoded therefrom, are administered to the selected subject under conditions effective to treat or inhibit onset of Huntington's disease in the subject.

Exemplary modulators for these genes include, without limitation: dexfosfoserine; pregabalin; verapamil; bepridil; celecoxib; nisoldipine; gabapentin; gabapentin enacarbil; elpetrigine; atagabalin; bepridil hydrochloride; imagabalin; mibampator; butethal; butabarbital; butalbital; talbutal; secobarbital; metharbital; thiopental; primidone; mephobarbital; phenobarbital; (r,s)-ampa; chembl123132; aniracetam; chembl136800; chembl1255648; cyclothiazide; chemb177862; chembl334920; chembl1097939; piracetam; chemb1320642; chembl265301; gyki-52466; nbqx; chembl222418; tezampanel; amobarbital; aprobarbital; heptabarbital; hexobarbital; barbital; (s)-ampa; chembl594840; chembl1121915; quisqualate; chembl337577; chembl27130; dnqx; chembl333964; (s)-willardiine; chembl28472; talampanel; perampanel; irampanel; cx1739; dasolampanel; becampanel; farampator; mk-8777; zonampanel; topiramate; pentobarbital; pf-04958242; selurampanel; nicotine polacrilex; varenicline; barbital; pozanicline; cytisine; rivanicline; epibatidine; chembl11876219; chembl3103988; atracurium; chembl490153; hexamethonium; chembl407217; TC-2216; ABT-560; ispronicline; sofinicline; TC-6499; AZD1446; cp-601927; dexmecamylamine; nicotine; varenicline tartrate; benztropine mesylate; pentolinium; AZD0328; bradanicline; pentobarbital; chembl1201135; dexefaroxan; mecamylamine (chemb1267936); dianicline; altinicline; trimethaphan; oleic acid; tebanicline tosylate; nicotine polacrilex; carboplatin; paclitaxel; L-glutamate; dalfampridine; guanidine hydrochloride; tedisamil; nerispirdine; EVT401; adenosine triphosphate; chembl335550; chelerythrine; acebutolol; moclobemide; ivermectin; chemb377219; chembl255787; methylclothiazide; chemb1550637; sodium orthovanadate; chembl2338352; benzonatate; GSK1482160; AZD9056, CE224535; reserpine; norepinephrine; chemb1126506; methamphetamine; ketanserin; tetrabenazine; L-glutamate; dihydrokainate; 2S,4R-4-methylglutamate; O-benzyl-L-serine; chembl1628669; mesalamine; tezampanel; domoic acid; dysiherbaine; kainic acid; mesalamine; topiramate; CEP-2563; staurosporine; Chembl369507; Ticlopidine; GSK-690693; sotrastaurin; (7S)-Hydroxyl-staurosporine; midostaurin; quercetin; bryostatin; sotrastaurin acetate; ingenol mebutate; adenosine phosphate; theophylline; dyphylline; pentoxifylline; enprofylline; iloprost; papaverine; theobromine; inamrinone; [r]-mesopram; roflumilast; piclamilast; rolipram; filaminast; chembl1230617; chembl519827; cilomilast; (-)-rolipram; crisaborole; ibudilast; apremilast; chembl521203; chembl74078; propoxyphene; cdp840; sodium phenylbutyrate; chembl1232082; dipyridamole; theophylline sodium glycinate; flavoxate hydrochloride; aminophylline; resveratrol; caffeine; oxtriphylline; amlexanox; etazolate; cilobradine; zatebradine; chembl2052019; chembl395336; cyclic adenosine monophosphate; aspartic acid; clozapine; alcohol; haloperidol; wortmannin; olanzapine; phorbol myristate acetate; risperidone; lidocaine; and combinations thereof.

In yet another aspect one or more modulators of a monovalent inorganic cation transport gene selected from the group consisting of ABCC9, ASIC4, CACNA1A, CHRNA4, CNGB1, CNTN1, DPP10, DPP6, FGF12, FGF14, HCN2, KCND2, KCNJ9, KCNQ1, KCNS3, NALCN, NEDD4L, NKAIN4, P2RX7, PTGER3, SERPINE2, SGK1, SLC10A4, SLC17A8, SLC18A1, SLC22A3, SLC2A13, SLC5A9, SLC8A3, and SLC9A7, or protein encoded therefrom, are administered to the selected subject under conditions effective to treat or inhibit onset of Huntington's disease in the subject.

Exemplary modulators for these genes include, without limitation: naminidil; adenosine triphosphate; glyburide; sarakalim; pinacidil hydrate; minoxidil; pregabalin; verapamil; bepridil; celecoxib; nisoldipine; gabapentin; gabapentin enacarbil; elpetrigine; atagabalin; bepridil hydrochloride; imagabalin; chembl549906; chembl550795; sodium chloride; GSK-650394; dalfampridine; guanidine hydrochloride; tedisamil; nerispirdine; evt401; adenosine triphosphate; chembl335550; chelerythrine; acebutolol; moclobemide; ivermectin; chembl377219; chembl255787; methylclothiazide; chembl550637; sodium orthovanadate; chembl12338352; benzonatate; GSK1482160; AZD9056, CE224535; hydrochlorothiazide; chembl1229875; nicotine polacrilex; talbutal; butabarbital; butalbital; secobarbital; metharbital; thiopental; primidone; mephobarbital; phenobarbital; varenicline; amobarbital; aprobarbital; butethal; heptabarbital; hexobarbital; barbital; pozanicline; cytisine; rivanicline; epibatidine; chembl1876219; chembl3103988; atracurium; chembl490153; hexamethonium; chembl1407217; tc-2216; abt-560; ispronicline; sofinicline; tc-6499; cilobradine; zatebradine; chembl2052019; chembl395336; cyclic adenosine monophosphate; chembl199951; flupirtine; indapamide; bepridil; azimilide; chembl12070953; mefenamic acid; chembl1907717; niflumic acid; chembl298475; chembl342375; chembl332826; dolasetron; celecoxib; nerispirdine; ezogabine; indomethacin; tacrolimus; guanidine hydrochloride; tedisamil; dalfampridine; pyrimethamine; cobalt (ii) ionl verapamil pyrimethaminel cobalt (ii) ion; dihydrokainate; bimatoprost; dinoprostone; misoprostol; beraprost; chembl1628262; carbacyclin; cicaprost; cloprostenol (chembl2220404); enprostil; fluprostenol; iloprost; dinoprost; sulprostone; treprostinil; chembl357834; chembl1317823; chembl1565591; chembl358653; sarcnu; and combinations thereof.

In a further aspect of the present disclosure one or more modulators of a neuron projection gene selected from the group consisting of ADGRL3, ALCAM, BCAN, BCL11B, CACNA1A, CACNA1G, CALB1, CAMK2A, CHRNA4, CTTNBP2, DSCAM, GRIA2, GRIA4, GRID2, GRIK4, HCN2, KCND2, LGI3, LRRTM1, MAG, MBP, MYC, NCAM2, NCDN, NEFM, NEURL1, NFASC, NTM, PDE4B, PIK3R1, PTGER3, PTPRO, RAPGEF4, RGS8, ROBO2, SGK1, SIRT2, SLC17A8, SLC1A2, SLC8A3, SNAP91, SNPH, SYNDIG1, and UNC5A, or protein encoded therefrom, are administered to the selected subject under conditions effective to treat or inhibit onset of Huntington's disease in the subject.

Exemplary modulators for these genes include, without limitation: adenosine phosphate; theophylline; dyphylline; pentoxifylline; enprofylline; iloprost; papaverine; theobromine; inamrinone; [r]-mesopram; roflumilast; piclamilast; rolipram; filaminast; chembl1230617; chembl519827; cilomilast; (-)-rolipram; crisaborole; ibudilast; apremilast; chembl521203; chembl74078; propoxyphene; cdp840; sodium phenylbutyrate; chembl1232082; dipyridamole; theophylline sodium glycinate; flavoxate hydrochloride; aminophylline; resveratrol; caffeine; oxtriphylline; amlexanox; etazolate; pregabalin; verapamil; bepridil; celecoxib; nisoldipine; gabapentin; gabapentin enacarbil; elpetrigine; atagabalin; bepridil hydrochloride; imagabalin; carboplatin; paclitaxel; chembl1549906; chembl550795; sodium chloride; GSK-650394; dalfampridine; guanidine hydrochloride; tedisamil; nerispirdine; L-glutamate; dihydrokainate; 2S,4R-4-methylglutamate; O-benzyl-L-serine; chembl1628669; mesalamine; fluorouracil; pregabalin; gabapentin enacarbil; mibefradil dihydrochloride; trimethadione; cinnarizine; ethosuximide; zonisamide; anandamide; mibefradil; chembl1684954; flunarizine; methsuximide; bepridil hydrochloride; gabapentin; phensuximide; paramethadione; atagabalin; celecoxib; and imagabalin; nicotine polacrilex; talbutal; butabarbital; butalbital; secobarbital; metharbital; thiopental; primidone; mephobarbital; phenobarbital; varenicline; amobarbital; aprobarbital; butethal; heptabarbital; hexobarbital; barbital; pozanicline; cytisine; rivanicline; epibatidine; chembl1876219; chembl3103988; atracurium; chembl490153; hexamethonium; chembl1407217; tc-2216; abt-560; ispronicline; sofinicline; tc-6499; mibampator; (r,s)-ampa; chembl123132; aniracetam; chembl136800; chembl1255648; cyclothiazide; chembl177862; chembl334920; chembl1097939; piracetam; chembl320642; chembl265301; gyki-52466; nbqx; chembl222418; tezampanel; (s)-ampa; chembl1594840; chembl121915; quisqualate; chembl337577; chembl27130; dnqx; chembl333964; (s)-willardiine; chembl128472; talampanel; perampanel; irampanel; cx1739; dasolampanel; becampanel; farampator; mk-8777; zonampanel; topiramate; pentobarbital; pf-04958242; selurampanel; cyclothiazide; chembl1334920; chembl1097939; joro spider toxin; domoic acid; dysherbaine; kainic acid; mesalamine; 2S,4R-4-methylglutamate; chembl2313646; cyclosporine; interferon beta-1A; prednisone; quercetin; rutin; GSK-249320; cilobradine; zatebradine; chembl2052019; chembl395336; cyclic adenosine monophosphate; sodium lauryl sulfate; bimatoprost; dinoprostone; misoprostol; beraprost; chembl1628262; carbacyclin; cicaprost; cloprostenol (chembl2220404); enprostil; fluprostenol; iloprost; dinoprost; sulprostone; treprostinil; chembl357834; chembl1317823; chembl1565591; chembl358653; Nadroparin calcium; 4'-hydroxytamoxifen; Azacitidine; Thioguanine; Acivin; Adozelesin; Amifostine; Aminopterin; antibiotic; Bizelesin; Bromocriptin; Bryostatin; Calcitriol; Diethyl stilbestrol; Elsamitrucin; Estrone; folic acid; glutamine; Hypoxanthine; Imatinib; Cilmostin; melatonin; methylprednisolone; N-methyl-n-nitrosurea; Novobiocin; Chembl35482; phorbol myristate acetate; prednisone; Quinapril; Vorinostat; Sulindac; thrombin; thyrotropin; sodium beta-nicotinamide adenine dinucleotide phosphate; troglitazone; verapamil; Chembl100014; Chembl1213492; chorionic gonadotropin; perillyl alcohol; AMG-900; Alisertib; Dinaciclib; Roniciclib; Temozolomide; Prexasertib; PF-04691502; Puquitinib; PA-799; isoprenaline; sf-1126; wortmannin; gsk-2636771; ds-7423; omipalisib; recilisib; pwt-33587; rg-7666; vs-5584; copanlisib; gedatolisib; sonolisib; apitolisib; taselisib; pilaralisib (chembl3360203); voxtalisib; zstk-474; alpelisib; pi-103; pilaralisib (chembl3218575); wx-037; dactolisib; bgt-226 (chembl3545096); pictilisib; buparlisib; panulisib; gsk-1059615; azd-6482; buparlisib hydrochloride; LY-3023414; and combinations thereof.

In another aspect one or more modulators of a TCF7L2 target gene selected from the group consisting of BMP4, CCND1, CCND2, DOCK10, DOCK9, DUSP15, ENPP4, EPAS1, EPHB1, ERBB3, EVI2A, EVI2B, FA2H, GJB1, HAPLN2, HSPA2, ID3, LGI3, MBP, MOG, MYC, MYRF, NFASC, NKAIN1, NKX6-2, OLIG2, PLEKHB1, PLP1, PPP1R16B, RAB33A, RASGEFIB, RTKN, SIRT2, SLC1A2, SOX10, ST18, TMEM125, TMEM2, TPPP, TSPAN15, UGT8, and AATK, or protein encoded therefrom, are administered to the selected subject under conditions effective to treat or inhibit onset of Huntington's disease in the subject.

Exemplary modulators for these genes include, without limitation: agonists of the Wnt Signaling pathway including, without limitation, 2-amino-4-(3,4-(methylenedioxy)benzylamino)-6-(3-methoxyphenyl)pyrimidine (2-AMBMP), curcumin, and Simvastatin, as described in Blagodatski et al., "Targeting the Wnt Pathways for Therapies," Mol. Cell Ther. 2:28 (2014), which is hereby incorporated by reference in its entirety; arsenic trioxide; acetaminophen; vitamin e; cytarabine; gossypol; roniciclib; ribociclib; palbociclib; methotrexate; mycophenolic acid; nifedipine; tamoxifen; troglitazone; uracil; abemaciclib; briciclib; abemaciclib; decitabine; palbociclib.; pyroxamide; cyclosporine; interferon beta-1a; prednisone; quercetin; rutin; vemurafenib; nadroparin calcium; 4'-hydroxytamoxifen; azacitidine; thioguanine; acivicin; adozelesin; amifostine; aminopterin; antibiotic; bizelesin; bromocriptine; bryostatin; calcitriol; diethylstilbestrol; elsamitrucin; estrone; folic acid; glutamine; hypoxanthine; imatinib; indomethacin; lithium; cilmostim; melatonin; methylprednisolone; n-methyl-n-nitrosurea; novobiocin; chembl35482; phorbol myristate acetate; prednisone; quinapril; vorinostat; sulindac; thrombin; thyrotropin; sodium beta-nicotinamide adenine dinucleotide phosphate; troglitazone; verapamil; chembl100014; chembl1213492; gonadotropin, chorionic; perillyl alcohol; amg-900; alisertib; dinaciclib; temozolomide; prexasertib; sodium lauryl sulfate; 1-glutamate; dihydrokainate; 2s,4r-4-methylglutamate; o-benzyl-1-serine; chembl1628669; mesalamine; pyroxamide; and combinations thereof.

In a final aspect of the present disclosure one or more modulators of a gene involved in the NKX2.2→OLIG2→SOX10→MYRF regulatory cascade or protein encoded therefrom, are administered to the selected subject under conditions effective to treat or inhibit onset of Huntington's disease in the subject.

Exemplary modulators of genes in this pathway include, without limitation, vemurafenib.

Exemplary modulators and their corresponding gene targets of the present invention are shown in Table 4 below.

TABLE 4

| Gene | Drug |
|---|---|
| ALCAM | FLUOROURACIL[1] |
| PRKCQ | CEP-2563 |
| | STAUROSPORINE[2] |
| | CHEMBL369507[2] |
| | DEXFOSFOSERINE[2] |
| | TICLOPIDINE |
| | GSK-690693 |
| | SOTRASTAURIN |
| | (7S)-HYDROXYL-STAUROSPORINE |
| | MIDOSTAURIN |
| | QUERCETIN |
| | BRYOSTATIN |
| | SOTRASTAURIN ACETATE |
| | INGENOL MEBUTATE |
| DSCAM | CARBOPLATIN |
| | PACLITAXEL |
| ADGRB1 | DEXFOSFOSERINE |
| CACNA1A | PREGABALIN[3] |
| | VERAPAMIL[4] |
| | BEPRIDIL[2] |
| | CELECOXIB |
| | NISOLDIPINE |
| | GABAPENTIN |
| | GABAPENTIN ENACARBIL |
| | ELPETRIGINE |
| | ATAGABALIN |
| | BEPRIDIL HYDROCHLORIDE |
| | IMAGABALIN |
| NEDD4L | HYDROCHLOROTHIAZIDE |
| SGK1 | CHEMBL549906[5] |
| | CHEMBL550795[5] |
| | SODIUM CHLORIDE[6] |
| | GSK-650394 |
| ABCC9 | NAMINIDIL[25] |
| | ADENOSINE TRIPHOSPHATE[26] |
| | GLYBURIDE |
| | SARAKALIM |
| | PINACIDIL HYDRATE |
| | MINOXIDIL |
| CNTN1 | CHEMBL1229875 |
| KCNJ9 | CHEMBL99951 |
| | FLUPIRTINE |
| KCNQ1 | INDAPAMIDE[7] |
| | BEPRIDIL[8] |
| | AZIMILIDE[9] |
| | CHEMBL2070953 |
| | MEFENAMIC ACID |
| | CHEMBL1907717 |
| | NIFLUMIC ACID |
| | CHEMBL298475 |
| | CHEMBL342375 |
| | CHEMBL332826 |
| | DOLASETRON[10] |
| | CELECOXIB |
| | NERISPIRDINE |
| | EZOGABINE |
| | INDOMETHACIN |
| | TACROLIMUS |
| | GUANIDINE HYDROCHLORIDE |
| | TEDISAMIL |
| | DALFAMPRIDINE |
| KCNS3 | GUANIDINE HYDROCHLORIDE |
| | NERISPIRDINE |
| | DALFAMPRIDINE |
| | TEDISAMIL |
| NALCN | PYRIMETHAMINE |
| | COBALT (II) ION |
| | VERAPAMIL |
| SLC22A3 | SarCNU[11] |
| PTGER3 | BIMATOPROST[12] |
| | DINOPROSTONE[13] |
| | MISOPROSTOL[14] |
| | BERAPROST |
| | CHEMBL1628262 |
| | CARBACYCLIN |
| | CICAPROST |
| | CLOPROSTENOL (CHEMBL2220404) |
| | ENPROSTIL |

TABLE 4-continued

| Gene | Drug |
|---|---|
| | FLUPROSTENOL |
| | ILOPROST |
| | DINOPROST |
| | SULPROSTONE |
| | TREPROSTINIL |
| | CHEMBL357834 |
| | CHEMBL1317823 |
| | CHEMBL565591 |
| | CHEMBL358653 |
| MBP | CYCLOSPORINE[15] |
| | INTERFERON BETA-1A[16] |
| | PREDNISONE[17] |
| | QUERCETIN[18] |
| | RUTIN[18] |
| PIK3R1 | PF-04691502 |
| | Puquitinib |
| | PA-799 |
| | ISOPRENALINE[19] |
| | SF-1126 |
| | WORTMANNIN[5] |
| | GSK-2636771 |
| | DS-7423 |
| | OMIPALISIB |
| | RECILISIB |
| | PWT-33587 |
| | RG-7666 |
| | VS-5584 |
| | COPANLISIB |
| | GEDATOLISIB |
| | SONOLISIB |
| | APITOLISIB |
| | TASELISIB |
| | PILARALISIB (CHEMBL3360203) |
| | VOXTALISIB |
| | ZSTK-474 |
| | ALPELISIB |
| | PI-103 |
| | QUERCETIN |
| | PILARALISIB (CHEMBL3218575) |
| | WX-037 |
| | DACTOLISIB |
| | BGT-226 (CHEMBL3545096) |
| | PICTILISIB |
| | BUPARLISIB |
| | Panulisib |
| | GSK-1059615 |
| | AZD-6482 |
| | BUPARLISIB HYDROCHLORIDE |
| | LY-3023414 |
| SOX10 | VEMURAFENIB[20] |
| TCF7L2 | REPAGLINIDE |
| SIRT2 | SODIUM LAURYL SULFATE |
| MAG | GSK-249320 |
| LINGO1 | OPICINUMAB |
| NTRK3 | ALTIRATINIB |
| | CHEMBL2007421 |
| | PLX-3397 |
| | RADICICOL |
| | THYROXINE[21] |
| | ENTRECTINIB[22] |
| | LOXO-101 |
| | CEP-2563 |
| | LESTAURTINIB |
| | PLX-7486 |
| | AZD-6918 |
| | AZD-7451 |
| | MIDOSTAURIN[23] |
| MYC | NADROPARIN CALCIUM[28] |
| | 4'-HYDROXYTAMOXIFEN[29] |
| | AZACITIDINE[30] |
| | THIOGUANINE[31] |
| | ACIVICIN[32] |
| | ADOZELESIN[33] |
| | AMIFOSTINE[34] |
| | AMINOPTERIN[35] |
| | ANTIBIOTIC[36] |
| | BIZELESIN[37] |
| | BROMOCRIPTINE[38] |
| | BRYOSTATIN[39] |
| | CALCITRIOL[40] |
| | DIETHYLSTILBESTROL[41] |
| | ELSAMITRUCIN[42] |
| | ESTRONE[43] |
| | FOLIC ACID[44] |
| | GLUTAMINE[45] |
| | HYPOXANTHINE[46] |
| | IMATINIB[47] |
| | INDOMETHACIN[48] |
| | LITHIUM[49] |
| | CILMOSTIM[50] |
| | MELATONIN[51] |
| | METHYLPREDNISOLONE[52] |
| | N-METHYL-N-NITROSUREA[53] |
| | NOVOBIOCIN[54] |
| | CHEMBL35482[55] |
| | PHORBOL MYRISTATE ACETATE[56] |
| | PREDNISONE[57] |
| | QUINAPRIL[58] |
| | VORINOSTAT[59] |
| | SULINDAC[60] |
| | THROMBIN[61] |
| | THYROTROPIN[62] |
| | SODIUM beta-NICOTINAMIDE ADENINE DINUCLEOTIDE PHOSPHATE[63] |
| | TROGLITAZONE[64] |
| | VERAPAMIL[65] |
| | CHEMBL100014[66] |
| | CHEMBL1213492[67] |
| | GONADOTROPIN, CHORIONIC[68] |
| | PERILLYL ALCOHOL[69] |
| | AMG-900 |
| | ALISERTIB |
| | DINACICLIB |
| | Roniciclib |
| | TEMOZOLOMIDE |
| | PREXASERTIB[70] |
| GRID1 | L-GLUTAMATE[2] |
| HCN2 | CILOBRADINE |
| | ZATEBRADINE |
| | CHEMBL2052019 |
| | CHEMBL395336[5] |
| | CYCLIC ADENOSINE MONOPHOSPHATE[5] |
| PDE4B | ADENOSINE PHOSPHATE[71] |
| | THEOPHYLLINE[72] |
| | DYPHYLLINE[73] |
| | PENTOXIFYLLINE[2] |
| | ENPROFYLLINE[2] |
| | ILOPROST[74] |
| | PAPAVERINE[75] |
| | THEOBROMINE[76] |
| | INAMRINONE[2] |
| | [R]-Mesopram[5] |
| | ROFLUMILAST[77] |
| | PICLAMILAST[5] |
| | ROLIPRAM[5] |
| | FILAMINAST[5] |
| | CHEMBL1230617[2] |
| | CHEMBL519827[5] |
| | CILOMILAST[78] |
| | (-)-ROLIPRAM[79] |
| | CRISABOROLE |
| | IBUDILAST |
| | APREMILAST |
| | CHEMBL521203[5] |
| | CHEMBL74078[5] |
| | PROPOXYPHENE |
| | CDP840 |
| | SODIUM PHENYLBUTYRATE |
| | CHEMBL1232082 |
| | DIPYRIDAMOLE |
| | THEOPHYLLINE SODIUM GLYCINATE |
| | FLAVOXATE HYDROCHLORIDE |
| | AMINOPHYLLINE |
| | RESVERATROL |
| | CAFFEINE |
| | OXTRIPHYLLINE |

TABLE 4-continued

| Gene | Drug |
|---|---|
| PDE7B | AMLEXANOX |
| | ETAZOLATE |
| | DYPHYLLINE[2] |
| | CHEMBL484928 |
| | DIPYRIDAMOLE |
| | FLAVOXATE HYDROCHLORIDE |
| | PENTOXIFYLLINE |
| PLCL1 | QUINACRINE[80] |
| SLC1A1 | ASPARTIC ACID[81] |
| | L-GLUTAMATE[82] |
| | CLOZAPINE[83] |
| | ALCOHOL[84] |
| | HALOPERIDOL[85] |
| | STAUROSPORINE[86] |
| | WORTMANNIN |
| | OLANZAPINE |
| | PHORBOL MYRISTATE ACETATE[87] |
| | RISPERIDONE |
| | LIDOCAINE |
| CACNA1G | PREGABALIN |
| | GABAPENTIN ENACARBIL |
| | MIBEFRADIL DIHYDROCHLORIDE |
| | TRIMETHADIONE[88] |
| | CINNARIZINE[89] |
| | ETHOSUXIMIDE[90] |
| | VERAPAMIL[91] |
| | ZONISAMIDE[92] |
| | ANANDAMIDE |
| | MIBEFRADIL[93] |
| | CHEMBL1684954 |
| | FLUNARIZINE[94] |
| | METHSUXIMIDE[95] |
| | BEPRIDIL HYDROCHLORIDE |
| | GABAPENTIN |
| | PHENSUXIMIDE |
| | PARAMETHADIONE |
| | ATAGABALIN |
| | CELECOXIB |
| | IMAGABALIN |
| P2RX7 | EVT401 |
| | ADENOSINE TRIPHOSPHATE |
| | CHEMBL335550 |
| | CHELERYTHRINE |
| | ACEBUTOLOL |
| | MOCLOBEMIDE |
| | IVERMECTIN |
| | CHEMBL377219 |
| | CHEMBL255787 |
| | METHYCLOTHIAZIDE |
| | CHEMBL550637 |
| | SODIUM ORTHOVANAD |
| | CHEMBL2338352 |
| | BENZONATATE |
| | GSK1482160 |
| | AZD9056 |
| | CE-224535 |
| SLC18A1 | RESERPINE[96] |
| | NOREPINEPHRINE[97] |
| | CHEMBL12650627 |
| | METHAMPHETAMINE[27] |
| | KETANSERIN |
| | TETRABENAZINE |
| CHRNA4 | NICOTINE POLACRILEX |
| | TALBUTAL[24] |
| | BUTABARBITAL[24] |
| | BUTALBITAL[24] |
| | SECOBARBITAL[24] |
| | METHARBITAL[24] |
| | THIOPENTAL[24] |
| | PRIMIDONE[24] |
| | MEPHOBARBITAL[24] |
| | PHENOBARBITAL[24] |
| | VARENICLINE[24] |
| | AMOBARBITAL[24] |
| | APROBARBITAL[24] |
| | BUTETHAL[24] |
| | HEPTABARBITAL[24] |
| | HEXOBARBITAL[24] |
| | BARBITAL[24] |
| | POZANICLINE |
| | CYTISINE[98] |
| | RIVANICLINE |
| | EPIBATIDINE |
| | CHEMBL1876219 |
| | CHEMBL3103988 |
| | ATRACURIUM |
| | CHEMBL490153 |
| | HEXAMETHONIUM |
| | CHEMBL407217 |
| | TC-2216 |
| | ABT-560 |
| | ISPRONICLINE |
| | SOFINICLINE |
| | TC-6499 |
| | AZD1446 |
| | CP-601927 |
| | DEXMECAMYLAMINE |
| | NICOTINE |
| | VARENICLINE TARTRATE |
| | BENZTROPINE MESYLATE |
| | PENTOLINIUM |
| | AZD0328 |
| | BRADANICLINE |
| | PENTOBARBITAL |
| | CHEMBL1201135 |
| | DEXEFAROXAN |
| | MECAMYLAMINE (CHEMBL267936) |
| | DIANICLINE |
| | ALTINICLINE |
| | TRIMETHAPHAN |
| | OLEIC ACID |
| | TEBANICLINE TOSYLATE |
| KCND2 | DALFAMPRIDINE[99] |
| | GUANIDINE HYDROCHLORIDE |
| | TEDISAMIL |
| | NERISPIRDINE |
| GRIA2 | MIBAMPATOR |
| | BUTETHAL[24] |
| | L-GLUTAMATE[100] |
| | BUTABARBITAL[24] |
| | BUTALBITAL[24] |
| | TALBUTAL[24] |
| | SECOBARBITAL[24] |
| | METHARBITAL[24] |
| | THIOPENTAL[24] |
| | PRIMIDONE[24] |
| | MEPHOBARBITAL[24] |
| | PHENOBARBITAL[24] |
| | (R,S)-AMPA |
| | CHEMBL123132[5] |
| | ANIRACETAM[5] |
| | CHEMBL136800 |
| | CHEMBL1255648 |
| | CYCLOTHIAZIDE |
| | CHEMBL77862 |
| | CHEMBL334920 |
| | CHEMBL1097939 |
| | PIRACETAM |
| | CHEMBL320642 |
| | CHEMBL265301 |
| | GYKI-52466 |
| | NBQX |
| | CHEMBL222418 |
| | TEZAMPANEL |
| | AMOBARBITAL[24] |
| | APROBARBITAL[24] |
| | HEPTABARBITAL[24] |
| | HEXOBARBITAL[24] |
| | BARBITAL[5] |
| | (S)-AMPA[5] |
| | CHEMBL594840[5] |
| | CHEMBL121915[5] |
| | QUISQUALATE[5] |
| | CHEMBL337577[5] |
| | CHEMBL27130[5] |
| | DNQX[5] |

TABLE 4-continued

| Gene | Drug |
|---|---|
| | CHEMBL333964[5] |
| | (S)-WILLARDIINE[5] |
| | CHEMBL28472[5] |
| | TALAMPANEL |
| | PERAMPANEL |
| | IRAMPANEL |
| | CX1739 |
| | DASOLAMPANEL |
| | BECAMPANEL |
| | FARAMPATOR |
| | MK-8777 |
| | ZONAMPANEL |
| | TOPIRAMATE |
| | PENTOBARBITAL |
| | PF-04958242 |
| | Selurampanel |
| GRIA4 | MIBAMPATOR |
| | L-GLUTAMATE[101] |
| | (R,S)-AMPA |
| | CHEMBL123132 |
| | ANIRACETAM |
| | CHEMBL136800 |
| | CHEMBL1255648 |
| | CYCLOTHIAZIDE |
| | CHEMBL77862 |
| | CHEMBL334920 |
| | CHEMBL1097939 |
| | PIRACETAM |
| | CHEMBL320642 |
| | CHEMBL265301 |
| | GYKI-52466 |
| | NBQX |
| | TEZAMPANEL |
| | JORO SPIDER TOXIN 3 |
| | CHEMBL222418 |
| | TALAMPANEL[102] |
| | IRAMPANEL |
| | CX1739 |
| | PF-04958242 |
| | Selurampanel |
| | DASOLAMPANEL |
| | BECAMPANEL |
| | FARAMPATOR |
| | MK-8777 |
| | ZONAMPANEL |
| | PERAMPANEL |
| | TOPIRAMATE |
| GRID2 | L-GLUTAMATE[2] |
| GRIK4 | TEZAMPANEL |
| | L-GLUTAMATE[2,103] |
| | DOMOIC ACID |
| | DYSIHERBAINE |
| | KAINIC ACID |
| | MESALAMINE |
| | 2S,4R-4-METHYLGLUTAMATE |
| | TOPIRAMATE |
| | Selurampanel |
| CNTN1 | L-glutamate[104] |
| RAPGEF4 | CHEMBL2313646 |
| SLC1A2 | L-GLUTAMATE |
| | DIHYDROKAINATE |
| | 2S,4R-4-METHYLGLUTAMATE |
| | O-BENZYL-1-SERINE |
| | CHEMBL1628669 |
| | MESALAMINE |
| ACAN | ILOMASTAT |
| BCL6 | FENRETINIDE |
| | ONALESPIB[105] |
| CA10 | ZONISAMIDE[106] |
| CCND1 | ARSENIC TRIOXIDE[107] |
| | ACETAMINOPHEN[108] |
| | VITAMIN E-[109] |
| | CYTARABINE[110] |
| | GOSSYPOL[111] |
| | Roniciclib |
| | Ribociclib |
| | PALBOCICLIB |
| | METHOTREXATE[112] |
| | MYCOPHENOLIC ACID[113] |
| | NIFEDIPINE[114] |
| | TAMOXIFEN[115] |
| | TROGLITAZONE[116] |
| | URACIL[117] |
| | ABEMACICLIB |
| | BRICICLIB |
| CCND2 | Roniciclib |
| | ABEMACICLIB |
| | DECITABINE[118] |
| | Ribociclib |
| | PALBOCICLIB |
| CDS1 | XL-844 |
| | PREXASERTIB |
| CKMT1A | CREATINE[119] |
| DEPTOR | AZD-8055 |
| | OSI-027 |
| | INK-128 |
| DGKG | DEXFOSFOSERINE[120] |
| DOCK10 | PYROXAMIDE[121] |
| ETNK2 | MURAGLITAZAR |
| ETS2 | CARBOPLATIN |
| | PACLITAXEL |
| FAM19A5 | MEDRONIC ACID |
| GHR | SOMATREM |
| | SOMATROPIN[122] |
| | PEGVISOMANT[123] |
| | CHEMBL18872 |
| | IBUTAMOREN |
| | CHEMBL324218 |
| GJC2 | CARBENOXOLONE |
| | cA2 |
| | FLUFENAMIC ACID |
| | OCTANOL |
| GPR17 | ZALEPLON |
| | CHEMBL1466483 |
| | CHEMBL397209 |
| | ADENOSINE TRIPHOSPHATE |
| | UDP-GALACTOSE |
| | URIDINE DIPHOSPHATE GLUCOSE |
| | URIDINE_DIPHOSPHATE |
| LGR5 | CIMETIDINE |
| MATK | PYROXAMIDE[124] |
| MMP17 | MARIMASTAT[125] |
| | ILOMASTAT |
| NR3C2 | NIMODIPINE[126] |
| | PROGESTERONE[127] |
| | SPIRONOLACTONE[128] |
| | EPLERENONE[129] |
| | FELODIPINE[130] |
| | DESOXYCORTICOSTERONE PIVALATE[131] |
| | DROSPIRENONE[132] |
| | ALDOSTERONE[133] |
| | CORTICOSTERONE[5] |
| | HYDROCORTISONE |
| | DESOXYCORTICOSTERONE |
| | DEXAMETHASONE |
| | FLUDROCORTISONE |
| | PREDNISOLONE |
| | FINERENONE |
| | ONAPRISTONE |
| | PF-03882845 |
| | OXPRENOATE POTASSIUM |
| | XL550 |
| | MT-3995 |
| | LY2623091 |
| | DESOXYCORTICOSTERONE ACETATE |
| | FLUDROCORTISONE ACETATE |
| OXCT2 | SUCCINIC ACID |
| PADI2 | L-CITRULLINE[134] |
| PCSK6 | RACEPHEDRINE HYDROCHLORIDE |
| | CHEMBL566340 |
| PDE4A | PENTOXIFYLLINE[135] |
| | THEOPHYLLINE[136] |
| | DYPHYLLINE[137] |
| | ENPROFYLLINE[138] |
| | DIPYRIDAMOLE[139] |
| | ILOPROST[140] |

TABLE 4-continued

| Gene | Drug |
|---|---|
| | OXTRIPHYLLINE[141] |
| | ROFLUMILAST[142] |
| | PICLAMILAST[143] |
| | CRISABOROLE |
| | IBUDILAST[144] |
| | APREMILAST[145] |
| | DROTAVERINE[146] |
| | CHEMBL1229585[5] |
| | CHEMBL74078[5] |
| | TOFISOPAM[147] |
| | CDP840 |
| | SODIUM PHENYLBUTYRATE |
| | ROLIPRAM |
| | CHEMBL1232082 |
| | CHEMBL1358525 |
| | TADALAFIL |
| | MILRINONE |
| | THEOPHYLLINE SODIUM GLYCINATE |
| | AMINOPHYLLINE |
| | CILOMILAST |
| | FLAVOXATE HYDROCHLORIDE |
| | CHEMBL570015 |
| | PERAMIVIR |
| | AMLEXANOX |
| | SAFRAMYCIN A |
| | AROFYLLINE |
| | ETAZOLATE |
| PLD1 | CHOLINE[148] |
| | ICOSAPENT |
| | PHORBOL MYRISTATE ACETATE[149] |
| | TAMOXIFEN[150] |
| RND3 | GUANOSINE TRIPHOSPHATE[5] |
| S1PR2 | CHEMBL570352 |
| | OZANIMOD |
| | CHEMBL225155 |
| | CHEMBL1368758 |
| | FINGOLIMOD HYDROCHLORIDE |
| | AMISELIMOD HYDROCHLORIDE |

All of the references listed in Table 4 are hereby incorporated by reference in their entirety.

[1] Sim et al., "P21 and CD166 as predictive markers of poor response and outcome after fluorouracil-based chemoradiotherapy for the patients with rectal cancer," BMC Cancer 14:241 (2014); [2] Overington et al., "How Many Drug Targets Are There?" Nat. Rev. Drug. Discov. 5(12):993-6 (2006); [3] Gazulla et al., "The P/Q-type voltage-dependent calcium channel as pharmacological target in spinocerebellar ataxia type 6: gabapentin and pregabalin may be of therapeutic benefit," Med. Hypotheses 68(1):131-6 (2007); [4] Tfelt-Hansen et al., "Verapamil for cluster headache. Clinical pharmacology and possible mode of action," Headache 49(1):117-25 (2009); [5] Berman et al., "The Protein Data Bank," Nucleic Acids Res. 28(1):235-42 (2000); [6] Artunc et al., "Blunted DOCA/high salt induced albuminuria and renal tubulointerstitial damage in gene-targeted mice lacking SGK1," J. Mol. Med. (Berl) 84(9):737-46 (2006); [7] Ohya et al., "Molecular and functional characterization of ERG, KCNQ, and KCNE subtypes in rat stomach smooth muscle," Am. J. Physiol. Gastrointest. Liver Physiol. 282(2):G277-87 (2002); [8] Chouabe et al., "Effects of calcium channel blockers on cloned cardiac K+ channels IKr and IKs," Therapie 55(1):195-202 (2000); [9] Schmitt et al., "Effects of azimilide, a new class III antiarrhythmic drug, on reentrant circuits causing ventricular tachycardia and fibrillation in a canine model of myocardial infarction," J. Cardiovasc. Electrophysiol. 12(9):1025-33 (2001); [10] Kuryshev et al., "Interactions of the 5-hydroxytryptamine 3 antagonist class of antiemetic drugs with human cardiac ion channels," J. Pharmacol. Exp. Ther. 295(2):614-20 (2000); [11] Chen et al., "Expression of extraneuronal monoamine transporter gene and DNA repair gene vis-á-vis with antitumor efficacy of SarCNU in human tumor xenografts," Zhonghua Zhong Liu Za Zhi 23(2):122-4 (2001); [12] Sharif et al., "Ocular hypotensive FP prostaglandin (PG) analogs: PG receptor subtype binding affinities and selectivities, and agonist potencies at FP and other PG receptors in cultured cells," J. Ocul. Pharmacol. Ther. 19(6):501-15 (2003); [13] Sugimoto et al., "Prostaglandin E Receptors," J. Biol. Chem. 282(16):11613-7 (2007); [14] Li et al., "Misoprostol, an anti-ulcer agent and PGE2 receptor agonist, protects against cerebral ischemia," Neurosci. Lett. 438(2):210-5 (2008); [15] Pette et al., "In vitro modulation of human, autoreactive MBP-specific CD4+ T-cell clones by cyclosporin A," J. Neuroimmunol. 76(1-2):91-9 (1997); [16] Zang et al., "Immunoregulation and blocking antibodies induced by interferon beta treatment in MS," Neurology 55(3):397-404 (2000); [17] Wender et al., "Myelin basic protein stimulation index of CD 2 cells in the course of steroid treatment," Neurol. Neurochir. Pol. 33(4):765-70 (1999); [18] Aquino et al., "The constitutive heat shock protein-70 is required for optimal expression of myelin basic protein during differentiation of oligodendrocytes," Neurochem. Res. 23(3):413-20 (1998); [19] Slomiany et al., "Salivary phospholipid secretion in response to beta-adrenergic stimulation is mediated by Src kinase-dependent epidermal growth factor receptor transactivation," Biochem. Biophys. Res. Comm. 318(1):247-52 (2004); [20] Sun et al., "Reversible and adaptive resistance to BRAF(V600E) inhibition in melanoma," Nature 508(7494):118-22 (2014); [21] Roskoden et al., "Modulation of mRNA expression of the neurotrophins of the nerve-growth-factor family and their receptors in the septum and hippocampus of rats after transient postnatal thyroxine treatment. II. Effects on p75 and trk receptor expression," Exp. Brain Res. 127(3):307-13 (1999); [22] Drillon et al., "What hides behind the MASC: clinical response and acquired resistance to entrectinib after ETV6-NTRK3 identification in a mammary analogue secretory carcinoma (MASC)," Ann. Oncol. 27(5):920-6 (2016); [23] Chi et al., "ETV6-NTRK3 as a therapeutic target of small molecule inhibitor PKC412," Biochem. Biophys. Res. Comm. 429(1-2):87-92 (2012); [24] Yamakura et al., "Anesthetics and ion channels: molecular models and sites of action," Ann. Rev. Pharmacol. Toxicol. 41:23-51 (2001); [26] Rainbow et al., "Proximal C-terminal domain of sulphonylurea receptor 2A interacts with pore-forming Kir6 subunits in KATP channels," Biochem. J. 379(Pt 1):173-81 (2004); [27] Fleckenstein et al., "New insights into the mechanism of action of amphetamines," Annu. Rev. Pharmacol. Toxicol. 47:681-98 (2007); [28] Sustar et al., "Suppression of membrane microvesiculation—a possible anticoagulant and anti-tumor progression effect of heparin," Blood Cells Mol. Dis. 42(3):223-7 (2009); [29] Arnold et al., "c-Myc activation in transgenic mouse epidermis results in mobilization of stem cells and differentiation of their progeny," Curr. Biol. 11(8):558-68 (2001); [30] Hsiao et al., "Comparison of transformation by manganese sulfate and 5-azacytidine in Rat 6 cells overexpressing the c-myc oncogene," Carcinogenesis 17(12):2771-7 (1996); [31] French et al., "Queuine, a tRNA anticodon wobble base, maintains the proliferative and pluripotent potential of HL-60 cells in the presence of the differentiating agent 6-thioguanine," Proc Natl Acad Sci USA 88(2):370-4 (1991); [32] Weinberg et al., "Inhibition of tumor necrosis factor-alpha (TNF-alpha) and interleukin-1 beta (IL-1 beta) messenger RNA (mRNA) expression in HL-60 leukemia cells by pentoxifylline and dexamethasone: dissociation of acivicin-induced TNF-alpha and IL-1 beta mRNA expression from acivicin-induced monocytoid differentiation," Blood 79(12):3337-43 (1992); [33] Woynarowski et al., "Region-specific DNA damage by AT-specific DNA-reactive drugs is predicted by drug binding specificity," Biochemistry 39(32):9917-27 (2000); [34] Lu et al., "Repression of c-myc gene expression by the thiol and disulfide forms of the cytoprotector amifostine," Carcinogenesis 18(12):2457-9 (1997); [35] Chung et al., "Requirement of de novo protein synthesis for aminopterin-induced apoptosis in a mouse myeloma cell line," Immunol Lett. 77(3):127-31 (2001); [36] Toffoli et al., "In K562 leukemia cells treated with doxorubicin and hemin, a decrease in c-myc mRNA expression correlates with loss of self-renewal capability but not with erythroid differentiation," Leuk Res. 13(4):279-87 (1989); [37] Woynarowski et al., "Region-specific DNA damage by AT-specific DNA-reactive drugs is predicted by drug binding specificity," Biochemistry 39(32):9917-27 (2000); 38Burdman et al., "Bromocriptine and the expression of c-myc and c-fos in human prolactinomas," Neurol Res. 23(7):721-3 (2001); [39] Chen et al., "Activation of protein kinase C induces nuclear translocation of RFX1 and down-regulates c-myc via an intron 1× box in undifferentiated leukemia HL-60 cells," J Biol Chem. 275(41):32227-33 (2000); [40] Saunders et al., "Inhibition of c-myc in breast and ovarian carcinoma cells by 1,25-dihydroxyvitamin D3, retinoic acid and dexamethasone," Anticancer Drugs 4(2):201-8 (1993); [41] Salleh et al., "Gene expression profiling of p53(+/−) knockout and wild-type mice following diethylstilbestrol administration," IUBMB Life 56(7):409-16 (2004); [42] Portugal, J., "Chartreusin, elsamicin A and related anti-cancer antibiotics," Curr Med Chem Anticancer Agents 3(6):411-20 (2003); [43] Li et al., "[Effect of estrogen on the expression of c-myc protein of bone in mice]," Wei Sheng Yan Jiu. 29(6):402-4 (2000); [44] Cowley et al., "Elevated c-myc protooncogene expression in autosomal recessive polycystic kidney disease," Proc Natl Acad Sci USA 84(23):8394-8 (1987); [45] Todorova et al., "Modulation of p53 and c-myc in DMBA-induced mammary tumors by oral glutamine," Nutr Cancer 54(2):263-73 (2006); [46] Prochownik and Kukowska, "Deregulated expression of c-myc by murine erythroleukaemia cells prevents differentiation," Nature 322(6082):848-50 (1986); [47] Kawano et al., "Depsipeptide enhances imatinib mesylate-induced apoptosis of Bcr-Abl-positive cells and ectopic expression of cyclin D1, c-Myc or active MEK abrogates this effect," Anticancer Res. 24(5A):2705-12 (2004); [48] Zhu et al., "Differential apoptosis by indomethacin in gastric epithelial cells through the constitutive expression of wild-type p53 and/or up-regulation of c-myc," Biochem Pharmacol. 58(1):193-200 (1999); [49] Dominguez-Cáceres, et al., "Prolactin induces c-Myc expression and cell survival through activation of Src/Akt pathway in lymphoid cells," Oncogene 23(44):7378-90 (2004); [50] Sklar et al., "Transformation of mouse bone marrow cells by transfection with a human oncogene related to c-myc is associated with the endogenous production of macrophage colony stimulating factor 1," J Cell Physiol. 125(3):403-12 (1985); [51] Molis et al., "Melatonin modulation of estrogen-regulated proteins, growth factors, and proto-oncogenes in human breast cancer," J Pineal Res. 18(2):93-103 (1995); [52] Morris et al., "Decreased C-MYC and BCL2 expression correlates with methylprednisolone-mediated inhibition of Raji lymphoma growth," Biochem Mol Med. 60(2):108-15 (1997); [53] Kang et al., "DNA copy number alterations and expression of relevant genes in mouse thymic lymphomas induced by gamma-irradiation and N-methyl-N-nitrosourea," Cancer Genet Cytogenet. 166(1):27-35 (2006); [54] Aller and Baserga, "Selective increase of c-myc mRNA levels by methylglyoxal-bis (guanylhydrazone) and novobiocin in serum-stimulated fibroblasts," J Cell Physiol. 128(3):362-6 (1986); [55] Lepique et al., "Signal transduction in GO/G1-arrested mouse Y1 adrenocortical cells stimulated by ACTH and FGF2," Endocr Res. 26(4):825-32 (2000); [56] Chen et al., "Activation of protein kinase C induces nuclear translocation of RFX1 and down-regulates c-myc via an intron 1× box in undifferentiated leukemia HL-60 cells," J Biol Chem. 275(41):32227-33 (2000); [57] Thiesen et al., "Locally and systemically active glucocorticosteroids modify intestinal absorption of lipids in rats," Lipids 37(2):159-66 (2002); [58] Diez et al., "Quinapril inhibits c-Myc expression and normalizes smooth muscle cell proliferation in spontaneously hypertensive rats," Am J Hypertens. 10(10 Pt 1):1147-52 (1997); [59] Xu et al., "The histone deacetylase inhibitor suberoylanilide hydroxamic acid down-regulates expression levels of Bcr-abl, c-Myc and HDAC3 in chronic myeloid leukemia cell lines," *Int J Mol Med.* 15(1):169-72 (2005); [60]Wilson et al., "Novel detection and differential utilization of a c-myc transcriptional block in colon cancer chemoprevention," *Cancer Res.* 62(21):6006-10 (2002); [61]Magnaldo et al., "The mitogenic signaling pathway of fibroblast growth factor is not mediated through polyphosphoinositide hydrolysis and protein kinase C activation in hamster fibroblasts," *J Biol Chem.* 261(36):16916-22 (1986); [62]Heldin and Westermark, "Epidermal growth factor, but not thyrotropin, stimulates the expression of c-fos and c-myc messenger ribonucleic acid in porcine thyroid follicle cells in primary culture," *Endocrinology* 122(3):1042-6 (1988); [63]Drozdowski et al., "Short-chain fatty acids and total parenteral nutrition affect intestinal gene expression," *JPEN J Parenter Enteral Nutr.* 26(3):145-50 (2002); [64]Ohta et al., "Ligands for peroxisome proliferator-activated receptor gamma inhibit growth and induce apoptosis of human papillary thyroid carcinoma cells," *J Clin Endocrinol Metab.* 86(5):2170-7 (2001); [65]Takemura et al., "Effect of verapamil on the class I major histocompatibility complex antigen expression in K562 chronic myelogenous leukemia cells treated with recombinant human interferon-gamma," *Cancer Lett.* 65(2):99-106 (1992); [66]Rabizadeh et al., "Rapid alteration of c-myc and c-jun expression in leukemic cells induced to differentiate by a butyric acid prodrug," *FEBS Lett.* 328(3):225-9 (1993); [67]Li and Wu, "Histone deacetylase inhibitor, Trichostatin A, activates p21WAF1/CIP1 expression through downregulation of c-myc and release of the repression of c-myc from the promoter in human cervical cancer cells," *Biochem Biophys Res Commun.* 324(2):860-7 (2004); [68]Piontkewitz et al., "The expression of c-myc during follicular growth and luteal formation in the rat ovary in vivo," *J Endocrinol.* 152(3):395-406 (1997); [69]Clark, S. S., "Perillyl alcohol induces c-Myc-dependent apoptosis in Bcr/Abl-transformed leukemia cells," *Oncology* 70(1):13-8 (2006); [70]Sen et al., "CHK1 Inhibition in Small-Cell Lung Cancer Produces Single-Agent Activity in Biomarker-Defined Disease Subsets and Combination Activity with Cisplatin or Olaparib," *Cancer Res.* 77(14):3870-3884 (2017); [71]Porteous et al., "The genetics and biology of DISC1—an emerging role in psychosis and cognition," *Biol Psychiatry* 60(2):123-31 (2006); [72]Lipworth, B. J., "Phosphodiesterase-4 inhibitors for asthma and chronic obstructive pulmonary disease," *Lancet.* 365(9454):167-75 (2005); [73]Hariton, C., "Ocular hypotension induced by topical dopaminergic drugs and phosphodiesterase inhibitors," *Eur J Pharmacol.* 258(1-2):85-94 (1994); [74]Schermuly et al., "Zardaverine and aerosolised iloprost in a model of acute respiratory failure," *Eur Respir J.* 22(2):342-7 (2003); [75]Zhu et al., "The measurement of cyclic nucleotide phosphodiesterase 4 activities via the quantification of inorganic phosphate with malachite green," *Anal Chim Acta.* 636(1):105-10 (2009); [76]Deree et al., "Insights into the regulation of TNF-alpha production in human mononuclear cells: the effects of non-specific phosphodiesterase inhibition," *Clinics (Sao Paulo)* 63(3):321-8 (2008); [77]Barone et al., "Inhibition of phosphodiesterase type 4 decreases stress-induced defecation in rats and mice," *Pharmacology* 81(1):11-7 (2008); [78]Kroegel and Foerster, "Phosphodiesterase-4 inhibitors as a novel approach for the treatment of respiratory disease: cilomilast," *Expert Opin Investig Drugs* 16(1):109-24 (2007); [79]Chen et al., "TTD: Therapeutic Target Database," *Nucleic Acids Res.* 30(1):412-5 (2002); [80]Bjro et al., "Inhibitors of the arachidonic acid metabolism attenuate the thyroliberin (TRH) stimulated prolactin production without modifying the production of inositolphosphates in GH4C1 pituitary cells," *Scand J Clin Lab Invest.* 53(2):111-6 (1993); [81]Tao and Grewer, "Cooperation of the conserved aspartate 439 and bound amino acid substrate is important for high-affinity Na+ binding to the glutamate transporter EAAC1," *J Gen Physiol.* 2007 April; 129(4):331-44; [82]Yun et al., "Propofol reverses oxidative stress-attenuated glutamate transporter EAAT3 activity: evidence of protein kinase C involvement," *Eur J Pharmacol.* 565(1-3):83-8 (2007); [83]Schmitt et al., "Decreased gene expression of glial and neuronal glutamate transporters after chronic antipsychotic treatment in rat brain," *Neurosci Lett.* 347(2):81-4 (2003); [84]Kim et al., "Effects of ethanol on the rat glutamate excitatory amino acid transporter type 3 expressed in Xenopus oocytes: role of protein kinase C and phosphatidylinositol 3-kinase," *Alcohol Clin Exp Res.* 27(10):1548-53 (2003); [85]Peisajovich and Shai, "Viral fusion proteins: multiple regions contribute to membrane fusion," *Biochim Biophys Acta.* 1614(1):122-9 (2003); [86]Do et al., "The effects of lidocaine on the activity of glutamate transporter EAAT3: the role of protein kinase C and phosphatidylinositol 3-kinase," *Anesth Analg.* 95(5):1263-8 (2002); [87]Guillet et al., "Differential regulation by protein kinases of activity and cell surface expression of glutamate transporters in neuron-enriched cultures," *Neurochem Int.* 46(4): 337-46 (2005); [88]Shen et al., "Prophylactic and therapeutic functions of T-type calcium blockers against noise-induced hearing loss," *Hear Res.* 226(1-2):52-60 (2007); [89]Cohen et al., "Block of T-type Ca channels in guinea pig atrial cells by antiarrhythmic agents and Ca channel antagonists," *J Gen Physiol.* 100(4):703-28 (1992); [90]Chen et al., "TTD: Therapeutic Target Database," *Nucleic Acids Res.* 30(1):412-5 (2002); [91]Freeze et al., "State-dependent verapamil block of the cloned human Ca(v)3.1 T-type Ca(2+) channel," *Mol Pharmacol.* 70(2):718-26 (2006); [92]Zaccara and Specchio, "Long-term safety and effectiveness of zonisamide in the treatment of epilepsy: a review of the literature," *Neuropsychiatr Dis Treat.* 5:249-59 (2009); [93]Clozel et al., "Discovery and main pharmacological properties of mibefradil (Ro 40-5967), the first selective T-type calcium channel blocker," J Hypertens Suppl. 15(5):S17-25 (1997); [94]Uebele et al., "Positive allosteric interaction of structurally diverse T-type calcium channel antagonists," *Cell Biochem Biophys.* 55(2):81-93 (2009); [95]Coulter et al., "Characterization of ethosuximide reduction of low-threshold calcium current in thalamic neurons," *Ann Neurol.* 25(6):582-93 (1989); [96]Ashe et al., "Vesicular monoamine transporter-1 (VMAT-1) mRNA and immunoreactive proteins in mouse brain," *Neuro Endocrinol Lett.* 32(3):253-8 (2011); [97]Erickson et al., "Distinct pharmacological properties and distribution in neurons and endocrine cells of two isoforms of the human vesicular monoamine transporter," *Proc Natl Acad Sci USA* 93(10):5166-71 (1996); [98]Walker et al., "Cytisine versus nicotine for smoking cessation," *N Engl J Med.* 371(25):2353-62 (2014); [99]Goodman and Stone, "Enhancing neural transmission in multiple sclerosis (4-aminopyridine therapy)," *Neurotherapeutics* 10(1):106-10 (2013); [100]Stein et al., "Complex pharmacological properties of recombinant alpha-amino-3-hydroxy-5-methyl-4-isoxazole propionate receptor subtypes," *Mol Pharmacol.* 42(5):864-71 (1992); [101]Cristovão et al., "Expression of AMPA/kainate receptors during development of chick embryo retina cells: in vitro versus in vivo studies," *Int J Dev Neurosci.* 20(1):1-9 (2002); [102]Langan et al., "Talampanel, a new antiepileptic drug: single- and multiple-dose pharmacokinetics and initial 1-week experience in patients with chronic intractable epilepsy," *Epilepsia* 44(1):46-53 (2003); [103]Korczak et al., "cDNA cloning and functional properties of human glutamate receptor EAA3 (GluR5) in homomeric and heteromeric configuration," *Receptors Channels* 3(1):41-9 (1995); [104]King et al., "Expression and activity of the glutamate transporter EAAT2 in cardiac hypertrophy: implications for ischaemia reperfusion injury," *Pflugers Arch* 452(6):674-682 (2006); [105]Hsieh et al., "Apoptosis and restriction of G(1)/S cell cycle by fenretinide in Burkitt's lymphoma mutu I cell line accessed with bcl-6 down-regulation," *Biochem Biophys Res Commun.* 276(3):1295-1301 (2000); [106]Biton V. "Clinical pharmacology and mechanism of action of zonisamide," *Clin Neuropharmacol.* 30(4):230-240 (2007); [107]Hyun et al., "Arsenic trioxide inhibits the growth of A498 renal cell carcinoma cells via cell cycle arrest or apoptosis," *Biochem Biophys Res Commun.* 300(1):230-235 (2003); [108]Gadd et al., "Acetaminophen-induced proliferation of estrogen-responsive breast cancer cells is associated with increases in c-myc RNA expression and NF-kappaB activity," *Toxicol Sci.* 66(2):233-243 (2002); [109]Galli et al., "The effect of alpha- and gamma-tocopherol and their carboxyethyl hydroxychroman metabolites on prostate cancer cell proliferation," *Arch Biochem Biophys.* 423(1):97-102 (2004); [110]Siitonen et al., "The effect of alpha- and gamma-tocopherol and their carboxyethyl hydroxychroman metabolites on prostate cancer cell proliferation," *Leuk Res.* 29(11):1335-1342 (2005); [111]Van Poznak et al., "Oral gossypol in the treatment of patients with refractory metastatic breast cancer: a phase I/II clinical trial," *Breast Cancer Res Treat.* 66(3):239-48 (2001); [112]Costea et al., "The influence of cyclin D1 (CCND1) 870A>G polymorphism and CCND1-thymidylate synthase (TS) gene-gene interaction on the outcome of childhood acute lymphoblastic leukaemia," *Pharmacogenetics.* 13(9):577-580 (2003); [113]Saitoh et al., "Medroxyprogesterone acetate induces cell proliferation through up-regulation of cyclin D1 expression via phosphatidylinositol 3-kinase/Akt/nuclear factor-kappaB cascade in human breast cancer cells," Endocrinology. 146(11):4917-4925 (2005); [114]Boutillier et al., "Depolarization regulates cyclin D1 degradation and neuronal apoptosis: a hypothesis about the role of the ubiquitin/proteasome signalling pathway," *Eur J Neurosci.* 11(2):441-448 (1999); 5 Han et al., "Cyclin D1 expression and patient outcome after tamoxifen therapy in estrogen receptor positive metastatic breast cancer," *Oncol Rep.* 10(1):141-144 (2003); [116]Sharma et al., "Peroxisome proliferator-activated receptor gamma activation modulates cyclin D1 transcription via beta-catenin-independent and cAMP-response element-binding protein-dependent pathways in mouse hepatocytes," *J Biol Chem.* 279(17):16927-16938 (2004); [117]Ogawa et al., "Aberrant expression of p27(Kip1) is associated with malignant transformation of the rat urinary bladder epithelium," *Carcinogenesis.* 21(1):117-121 (2000); [118]Yu et al., "Absence of cyclin D2 expression is associated with promoter hypermethylation in gastric cancer," *Br J Cancer.* 88(10):1560-1565 (2003); [119]Wyss et al., "Mitochondrial creatine kinase from chicken brain. Purification, biophysical characterization, and generation of heterodimeric and heterooctameric molecules with subunits of other creatine kinase isoenzymes," J Biol Chem. 265(26):15900-15908 (1990); Yamaguchi et al., "Phosphorylation and up-regulation of diacylglycerol kinase gamma via its interaction with protein kinase C gamma," *J Biol Chem.* 281(42):31627-31637 (2006); [121]Yelo et al., "Dock10, a novel CZH protein selectively induced by interleukin-4 in human B lymphocytes," *Mol Immunol.* 45(12):3411-3418 (2008); [122]Bernstein et al., "Hormones and body size evolution in papionin primates," *Am J Phys Anthropol.* 132(2):247-260 (2007); [123]Moller et al., "Impact of growth hormone receptor blockade on substrate metabolism during fasting in healthy subjects," *J Clin Endocrinol Metab.* 94(11):4524-4532 (2009); [124]Hiremath et al., "Complex regulation of the Csk homologous kinase (Chk) by IL-4 family cytokines and IFN-gamma in human peripheral blood monocytes," *Mol Immunol.* 41(9):901-910 (2004); [125]Heath et al., "Clinical potential of matrix metalloprotease inhibitors in cancer therapy," *Drugs.* 59(5): 1043-1055 (2000); [126]Dietz et al., "A number of marketed dihydropyridine calcium channel blockers have mineralocorticoid receptor antagonist activity," *Hypertension.* 51(3):742-748 (2008); [127]Rupprecht et al., "Pharmacological and functional characterization of human mineralocorticoid and glucocorticoid receptor ligands," *Eur J Pharmacol.* 15; 247(2):145-154 (1993); [128]Sica D A., "Pharmacokinetics and pharmacodynamics of mineralocorticoid blocking agents and their effects on potassium homeostasis," Heart Fail Rev. 10(1):23-29 (2005); [129]Rogerson et al., "Differences in the determinants of eplerenone, spironolactone and aldosterone binding to the mineralocorticoid receptor," *Clin Exp Pharmacol Physiol.* 31(10):704-709 (2004); [130]Dietz et al., "A number of marketed dihydropyridine calcium channel blockers have mineralocorticoid receptor antagonist activity," *Hypertension.* 51(3):742-748 (2008); [131]Beaumont et al., "Characterization of rat brain aldosterone receptors reveals high affinity for corticosterone," *Endocrinology.* 113(6):2043-2051 (1983); [132]Oelkers W K., "Effects of estrogens and progestogens on the renin-aldosterone system and blood pressure," *Steroids.* 61(4):166-171 (1996); [133]Bunda et al., "Aldosterone induces elastin production in cardiac fibroblasts through activation of insulin-like growth factor-I receptors in a mineralocorticoid receptor-independent manner," *Am J Pathol.* 171(3):809-819 (2007); [134]Dong et al., "Regulation of the expression of peptidylarginine deiminase type II gene (*PADI2*) in human keratinocytes involves Sp1 and Sp3 transcription factors," J Invest Dermatol. 124(5):1026-1033 (2005); [135]Chen et al., "TTD: Therapeutic Target Database," *Nucleic Acids Res.* 30(1):412-415 (2002); [136]Haider S., "Cyclic AMP level and phosphodiesterase activity during 17alpha,20beta-dihydroxy-4-pregnen-3-one induction and theophylline inhibition of oocyte maturation in the catfish, Clarias batrachus," *Comp Biochem Physiol A Mol Integr Physiol.* 134(2): 267-274 (2003); [137]Hariton C., "Ocular hypotension induced by topical dopaminergic drugs and phosphodiesterase inhibitors," *Eur J Pharmacol.* 258(1-2):85-94 (1994); [138]Berg et al., "Effects of different phosphodiesterase-inhibiting drugs on human pregnant myometrium: an in vitro study," *Arch Int Pharmacodyn Ther.* 290(2):288-292 (1987); [139]Chen et al., "TTD: Therapeutic Target Database," *Nucleic Acids Res.* 30(1):412-415 (2002); [140]Schemmuly et al., "Zardaverine and aerosolised iloprost in a model of acute respiratory failure," *Eur Respir J* 22(2):342-347 (2003); [141]Haider S., "Cyclic AMP level and phosphodiesterase activity during 17alpha,20beta-dihydroxy-4-pregnen-3-one induction and theophylline inhibition of oocyte maturation in the catfish, Clarias batrachus," *Comp Biochem Physiol A Mol Integr Physiol.* 134(2):267-274 (2003); [142]Barone et al., "Inhibition of phosphodiesterase type 4 decreases stress-induced defecation in rats and mice," *Pharmacology.* 81(1):11-17 (2008); [143]Beeh et al., "Effects of piclamilast, a selective phosphodiesterase-4 inhibitor, on oxidative burst of sputum cells from mild asthmatics and stable COPD patients," *Lung.* 182(6):369-377 (2004); [144]Yamazaki et al., "Ibudilast, a mixed PDE3/4 inhibitor, causes a selective and nitric oxide/cGMP-independent relaxation of the intracranial vertebrobasilar artery," *Eur J Pharmacol.* 650(2-3):605-611 (2011); [145]Abdulrahim et al., "Apremilast: a PDE4 inhibitor for the treatment of psoriatic arthritis," *Expert Opin Pharmacother.* 16(7):1099-1108 (2015); [146]Muravyov et al., "Hemorheological efficiency of drugs, targeting on intracellular phosphodiesterase activity: in vitro study," *Clin Hemorheol Microcirc.* 36(4):327-334 (2007); [147]Rundfeldt et al., "The atypical anxiolytic drug, tofisopam, selectively blocks phosphodiesterase isoenzymes and is active in the mouse model of negative symptoms of psychosis," *J Neural Transm* (Vienna). 117(11):1319-1325 (2010); [148]Lee et al., "Phosphatidylinositol (3,4,5)-trisphosphate specifically interacts with the phox homology domain of phospholipase D1 and stimulates its activity," *J Cell Sci.* 118(Pt 19):4405-4413 (2005); [149]Kim et al., "Phospholipase D1 is located and activated by protein kinase C alpha in the plasma membrane in 3Y1 fibroblast cell," *Biochim Biophys Acta.* 1436(3):319-330 (1999); [150]Eisen et al., "Selective estrogen receptor (ER) modulators differentially regulate phospholipase D catalytic activity in ER-negative breast cancer cells," *Mol Pharmacol.* 62(4): 911-20 (2002)

In one embodiment, the methods described herein further include administering to the selected subject a preparation of human glial progenitor cells.

The human glial progenitor cells may be derived from any suitable source of glial cells, such as, for example and without limitation, human induced pluripotent stem cells (iPSCs), embryonic stem cells, fetal tissue, and/or astrocytes as described in more detail below.

iPSCs are pluripotent cells that are derived from non-pluripotent cells, such as somatic cells. For example, and without limitation, iPSCs can be derived from tissue, peripheral blood, umbilical cord blood, and bone marrow (see e.g., Cai et al., "Generation of Human Induced Pluripotent Stem Cells from Umbilical Cord Matrix and Amniotic Membrane Mesenchymal Cells," *J. Biol. Chem.* 285(15):112227-11234 (2110); Giorgetti et al., "Generation of Induced Pluripotent Stem Cells from Human Cord Blood Cells with only Two Factors: Oct4 and Sox2," *Nat. Protocol.* 5(4):811-820 (2010); Streckfuss-Bomeke et al., "Comparative Study of Human-Induced Pluripotent Stem Cells Derived from Bone Marrow Cells, Hair Keratinocytes, and Skin Fibroblasts," *Eur. Heart J.* doi:10.1093/eurheartj/ehs203 (Jul. 12, 2012); Hu et al., "Efficient Generation of Transgene-Free Induced Pluripotent Stem Cells from Normal and Neoplastic Bone Marrow and Cord Blood Mononuclear Cells," *Blood* doi: 10.1182/blood-2010-07-298331 (Feb. 4, 2011); Sommer et al., "Generation of Human Induced Pluripotent Stem Cells from Peripheral Blood using the STEMCCA Lentiviral Vector," *J. Vis. Exp.* 68:e4327 doi:10.3791/4327 (2012), which are hereby incorporated by reference in their entirety). The somatic cells are reprogrammed to an embryonic stem cell-like state using genetic manipulation. Exemplary somatic cells suitable for the formation of iPSCs include fibroblasts (see e.g., Streckfuss-Bomeke et al., "Comparative Study of Human-Induced Pluripotent Stem Cells Derived from Bone Marrow Cells, Hair Keratinocytes, and Skin Fibroblasts," *Eur. Heart J.* doi:10.1093/eurheartj/ehs203 (2012), which is hereby incorporated by reference in its entirety), such as dermal fibroblasts obtained by a skin sample or biopsy, synoviocytes from synovial tissue, keratinocytes, mature B cells, mature T cells, pancreatic R cells, melanocytes, hepatocytes, foreskin cells, cheek cells, or lung fibroblasts.

Methods of producing induced pluripotent stem cells are known in the art and typically involve expressing a combination of reprogramming factors in a somatic cell. Suitable reprogramming factors that promote and induce iPSC generation include one or more of Oct4, Klf4, Sox2, c-Myc, Nanog, C/EBPα, Esrrb, Lin28, and Nr5a2. In certain embodiments, at least two reprogramming factors are expressed in a somatic cell to successfully reprogram the somatic cell. In other embodiments, at least three reprogramming factors are expressed in a somatic cell to successfully reprogram the somatic cell.

iPSCs may be derived by methods known in the art, including the use integrating viral vectors (e.g., lentiviral vectors, inducible lentiviral vectors, and retroviral vectors), excisable vectors (e.g., transposon and floxed lentiviral vectors), and non-integrating vectors (e.g., adenoviral and plasmid vectors) to deliver the genes that promote cell reprogramming (see e.g., Takahashi and Yamanaka, *Cell* 126:663-676 (2006); Okita. et al., *Nature* 448:313-317 (2007); Nakagawa et al., *Nat. Biotechnol.* 26:101-106 (2007); Takahashi et al., *Cell* 131:1-12 (2007); Meissner et al. *Nat. Biotech.* 25:1177-1181 (2007); Yu et al. *Science* 318:1917-1920 (2007); Park et al. *Nature* 451:141-146 (2008); and U.S. Patent Application Publication No. 2008/0233610, which are hereby incorporated by reference in their entirety). Other methods for generating IPS cells include those disclosed in WO2007/069666, WO2009/006930, WO2009/006997, WO2009/007852, WO2008/118820, U.S. Patent Application Publication No. 2011/0200568 to Ikeda et al., U.S. Patent Application Publication No 2010/0156778 to Egusa et al., U.S. Patent Application Publication No 2012/0276070 to Musick, and U.S. Patent Application Publication No 2012/0276636 to Nakagawa, Shi et al., *Cell Stem Cell* 3(5):568-574 (2008), Kim et al., *Nature* 454:646-650 (2008), Kim et al., *Cell* 136(3):411-419 (2009), Huangfu et al., *Nat. Biotechnol.* 26:1269-1275 (2008), Zhao et al., *Cell Stem Cell* 3:475-479 (2008), Feng et al., *Nat. Cell Biol.* 11:197-203 (2009), and Hanna et al., *Cell* 133(2):250-264 (2008) which are hereby incorporated by reference in their entirety.

The methods of iPSC generation described above can be modified to include small molecules that enhance reprogramming efficiency or even substitute for a reprogramming factor. These small molecules include, without limitation, epigenetic modulators such as, the DNA methyltransferase inhibitor 5'-azacytidine, the histone deacetylase inhibitor VPA, and the G9a histone methyltransferase inhibitor BIX-01294 together with BayK8644, an L-type calcium channel agonist. Other small molecule reprogramming factors include those that target signal transduction pathways, such as TGF-β inhibitors and kinase inhibitors (e.g., kenpaullone) (see review by Sommer and Mostoslavsky, "Experimental Approaches for the Generation of Induced Pluripotent Stem Cells," *Stem Cell Res. Ther.* 1:26 doi:10.1186/scrt26 (Aug. 10, 2010), which is hereby incorporated by reference in its entirety).

Methods of obtaining highly enriched preparations of glial progenitor cells from the iPSCs that are suitable for the methods described herein are disclosed in WO2014/124087 to Goldman and Wang, and Wang et al., "Human iPSC-Derived Oligodendrocyte Progenitors Can Myelinate and Rescue a Mouse Model of Congenital Hypomyelination," *Cell Stem Cell* 12(2):252-264 (2013), which are hereby incorporated by reference in their entirety.

In another embodiment the human glial progenitor cells are derived from embryonic stem cells. Human embryonic stem cells provide a virtually unlimited source of clonal/ genetically modified cells potentially useful for tissue replacement therapies. Methods of obtaining highly enriched preparations of glial progenitor cells from embryonic cells that are suitable for use in the methods of the present disclosure are described in Wang et al., "Human iPSC-derived oligodendrocyte progenitor cells can myelinate and rescue a mouse model of congenital hypomyelination," *Cell Stem Cell* 12:252-264 (2013), which is hereby incorporated by reference in its entirety.

In another embodiment, the human glial progenitor cells are derived from human fetal tissue. Glial progenitor cells can be extracted from fetal brain tissue containing a mixed population of cells directly by using the promoter specific separation technique as described in U.S. Patent Application Publication Nos. 20040029269 and 20030223972 to Goldman, which are hereby incorporated by reference in their entirety. This method involves selecting a promoter which functions specifically in glial progenitor cells, and introducing a nucleic acid encoding a marker protein under the control of said promoter into the mixed population cells. The mixed population of cells is allowed to express the marker protein and the cells expressing the marker protein are separated from the population of cells, with the separated cells being the glial progenitor cells. Human glial progenitor cells can be isolated from ventricular or subventricular zones of the brain or from the subcortical white matter.

Glial specific promoters that can be used for isolating glial progenitor cells from a mixed population of cells include the CNP promoter (Scherer et al., *Neuron* 12:1363-75 (1994), which is hereby incorporated by reference in its entirety), an NCAM promoter (Holst et al., *J. Biol. Chem.* 269:22245-52 (1994), which is hereby incorporated by reference in its entirety), a myelin basic protein promoter (Wrabetz et al., *J. Neurosci. Res.* 36:455-71 (1993), which is hereby incorporated by reference in its entirety), a JC virus minimal core promoter (Krebs et al., *J. Virol.* 69:2434-42 (1995), which is hereby incorporated by reference in its entirety), a myelin-associated glycoprotein promoter (Laszkiewicz et al., "Structural Characterization of Myelin-associated Glycoprotein Gene Core Promoter," *J. Neurosci. Res.* 50(6): 928-36 (1997), which is hereby incorporated by reference in its entirety), or a proteolipid protein promoter (Cook et al., "Regulation of Rodent Myelin Proteolipid Protein Gene Expression," *Neurosci. Lett.* 137(1): 56-60 (1992); Wight et al., "Regulation of Murine Myelin Proteolipid Protein Gene Expression," *J. Neurosci. Res.* 50(6): 917-27 (1997); and Cambi et al., *Neurochem. Res.* 19:1055-60 (1994), which are hereby incorporated by reference in their entirety). See also U.S. Pat. No. 6,245,564 to Goldman et. al., which is hereby incorporated by reference in its entirety.

The glial progenitor cell population derived from fetal tissue can be enriched for by first removing neurons or neural progenitor cells from the mixed cell population. Where neuronal progenitor cells are to be separated from the mixed population of cells, they can be removed based on their surface expression of NCAM, PSA-NCAM, or any other surface moiety specific to neurons or neural progenitor cells. Neurons or neural progenitor cells may also be separated from a mixed population of cells using the promoter based separation technique. Neuron or neural progenitor specific promoters that can be used for separating neural cells from a mixed population of cells include the Tal tubulin promoter (Gloster et al., *J. Neurosci.* 14:7319-30 (1994), which is hereby incorporated by reference in its entirety), a Hu promoter (Park et al., "Analysis of Upstream Elements in the HuC Promoter Leads to the Establishment of Transgenic Zebrafish with Fluorescent Neurons," *Dev. Biol.* 227 (2): 279-93 (2000), which is hereby incorporated by reference in its entirety), an ELAV promoter (Yao et al., "Neural Specificity of ELAV Expression: Defining a *Drosophila* Promoter for Directing Expression to the Nervous System," *J. Neurochem.* 63(1): 41-51 (1994), which is hereby incorporated by reference in its entirety), a MAP-1B promoter (Liu et al., *Gene* 171:307-08 (1996), which is hereby incorporated by reference in its entirety), or a GAP-43 promoter. Techniques for introducing the nucleic acid molecules of the construct into the plurality of cells and then sorting the cells are described in U.S. Pat. No. 6,245,564 to Goldman et al., and U.S. Patent Application Publication No. 20040029269 to Goldman et al., which are hereby incorporated by reference in their entirety.

As an alternative to using promoter-based cell sorting to recover glial progenitor cells from a mixed population of cells, an immunoseparation procedure can be utilized. In a positive immunoseparation technique, the desired cells (i.e. glial progenitor cells) are isolated based on proteinaceous surface markers naturally present on the progenitor cells. For example, the surface marker A2B5 is an initially expressed early marker of glial progenitor cells (Nunes et al., "Identification and Isolation of Multipotential Neural Progenitor Cells from the Adult Human White Matter," *Soc. Neurosci. Abstr.* (2001), which is hereby incorporated by reference in its entirety). Using an antibody specific to A2B5, glial progenitor cells can be separated from a mixed population of cell types. Similarly, the surface marker CD44 identifies astrocyte-biased glial progenitor cells (Liu et al., "CD44 Expression Identifies Astrocyte-Restricted Precursor Cells," *Dev. Biol.* 276:31-46 (2004), which is hereby incorporated by reference in its entirety). Using CD44-conjugated microbead technology, astroctye-biased glial progenitor cells can be separated from a mixed population of cell types. Oligodendrocyte-biased glial progenitor cells can be separated from a mixed population of cell types based on expression of PDGFαR, the PDGFαR ectodomain CD140a, or CD9. Cells expressing markers of non-glial cell types (e.g., neurons, inflammatory cells, etc.) can be removed from the preparation of glial cells to further enrich the preparation for the desired glial cell type using immunoseparation techniques. For example, the glial progenitor cell population is preferably negative for a PSA-NCAM marker and/or other markers for cells of neuronal lineage, negative for one or more inflammatory cell markers, e.g., negative for a CD11 marker, negative for a CD32 marker, and/or negative for a CD36 marker, which are markers for microglia. Exemplary microbead technologies include MACS Microbeads, MACS® Columns, and MACS® Separators. Additional examples of immunoseparation are described in Wang et al., "Prospective Identification, Direct Isolation, and Expression Profiling of a Telomerase Expressing Subpopulation of Human Neural Stem Cells, Using Sox2 Enhancer-Directed FACS," *J. Neurosci.* 30:14635-14648 (2010); Keyoung et al., "High-Yield Selection and Extraction of Two Promoter-Defined Phenotypes of Neural Stem Cells from the Fetal Human Brain," *Nat. Biotechnol.* 19:843-850 (2001); and Windrem et al., "Neonatal Chimerization with Human Glial Progenitor Cells can both Remyelinate and Rescue the Otherwise Lethally Hypomyelinated Shiverer Mouse," *Cell Stem Cell* 2:553-565 (2008), which are hereby incorporated by reference in their entirety.

In accordance with the methods described herein, the selected preparation of administered human glial progenitor cells comprise at least about 80% glial progenitor cells, including, for example, about 80%, 85%, 90%, 95%, 96%, 97%, 98%, 99%, 100% glial progenitor cells. The selected preparation of glial progenitor cells can be relatively devoid (e.g., containing less than 20, 15, 10, 9, 8, 7, 6, 5, 4, 3, 2, or 1%) of other cells types such as neurons or cells of neuronal lineage, fibrous astrocytes and cells of fibrous astrocyte lineage, and pluripotential stem cells (like ES cells). Optionally, example cell populations are substantially pure populations of glial progenitor cells.

The glial progenitor cells of the administered preparation can optionally be genetically modified to express other proteins of interest. For example, the glial progenitor cells may be modified to express a therapeutic biological molecule, an exogenous targeting moiety, an exogenous marker (for example, for imaging purposes), or the like. The glial progenitor cells of the preparations can be optionally modified to overexpress an endogenous biological molecule, targeting moiety, and/or marker.

The glial progenitor cells of the administered preparation may be astrocyte-biased glial progenitor cells, oligodendrocyte-biased glial progenitor cells, unbiased glial progenitor cells, or a combination thereof. The glial progenitor cells of the administered preparation express one or more markers of the glial cell lineage. For example, in one embodiment, the glial progenitor cells of the administered preparation may express A2B5$^+$. In another embodiment, glial progenitor cells of the administered preparation are positive for a PDGFαR marker. The PDGFαR marker is optionally a PDGFαR ectodomain, such as CD140a. PDGFαR and CD140a are markers of an oligodendrocyte-biased glial progenitor cells. In another embodiment, glial progenitor cells of the administered preparation are CD44$^+$. CD44 is a marker of an astrocyte-biased glial progenitor cell. In another embodiment, glial progenitor cells of the administered preparation are positive for a CD9 marker. The CD9 marker is optionally a CD9 ectodomain. In one embodiment, the glial progenitor cells of the preparation are A2B5$^+$, CD140a$^+$, and/or CD44$^+$. The aforementioned glial progenitor cell surface markers can be used to identify, separate, and/or enrich the preparation for glial progenitor cells prior to administration.

The administered glial progenitor cell preparation is optionally negative for a PSA-NCAM marker and/or other neuronal lineage markers, and/or negative for one or more inflammatory cell markers, e.g., negative for a CD11 marker, negative for a CD32 marker, and/or negative for a CD36 marker (which are markers for microglia). Optionally, the preparation of glial progenitor cells are negative for any combination or subset of these additional markers. Thus, for example, the preparation of glial progenitor cells is negative for any one, two, three, or four of these additional markers.

Suitable methods of introducing cells into the striatum, forebrain, brain stem, and/or cerebellum of a subject are well known to those of skill in the art and include, but are not limited to, injection, deposition, and grafting as described herein.

In one embodiment, the glial progenitor cells are transplanted bilaterally into multiple sites of the subject as described U.S. Pat. No. 7,524,491 to Goldman, Windrem et al., "Neonatal Chimerization With Human Glial Progenitor Cells Can Both Remyelinate and Rescue the Otherwise Lethally Hypomyelinated Shiverer Mouse," *Cell Stem Cell* 2:553-565 (2008), Han et al., "Forebrain Engraftment by Human Glial Progenitor Cells Enhances Synaptic Plasticity and Learning Adult Mice," *Cell Stem Cell* 12:342-353 (2013), and Wang et al., "Human iPSCs-Derived Oligodendrocyte Progenitor Cells Can Myelinate and Rescue a Mouse Model of Congenital Hypomyelination," *Cell Stem Cell* 12:252-264 (2013), which are hereby incorporated by reference in their entirety). Methods for transplanting nerve tissues and cells into host brains are described by Bjorklund and Stenevi (eds), Neural Grafting in the Mammalian CNS, Ch. 3-8, Elsevier, Amsterdam (1985); U.S. Pat. No. 5,082,670 to Gage et al.; and U.S. Pat. No. 6,497,872 to Weiss et al., which are hereby incorporated by reference in their entirety. Typical procedures include intraparenchymal, intracallosal, intraventricular, intrathecal, and intravenous transplantation.

Intraparenchymal transplantation is achieved by injection or deposition of tissue within the host brain so as to be apposed to the brain parenchyma at the time of transplantation. The two main procedures for intraparenchymal transplantation are: 1) injecting the donor cells within the host brain parenchyma or 2) preparing a cavity by surgical means to expose the host brain parenchyma and then depositing the graft into the cavity (Bjorklund and Stenevi (eds), *Neural Grafting in the Mammalian CNS*, Ch. 3, Elsevier, Amsterdam (1985), which is hereby incorporated by reference in its entirety). Both methods provide parenchymal apposition between the donor cells and host brain tissue at the time of grafting, and both facilitate anatomical integration between the graft and host brain tissue. This is of importance if it is required that the donor cells become an integral part of the host brain and survive for the life of the host.

Glial progenitor cells can also be delivered intracallosally as described in U.S. Patent Application Publication No. 20030223972 to Goldman, which is hereby incorporated by reference in its entirety. The glial progenitor cells can also be delivered directly to the forebrain subcortex, specifically into the anterior and posterior anlagen of the corpus callosum. Glial progenitor cells can also be delivered to the cerebellar peduncle white matter to gain access to the major cerebellar and brainstem tracts. Glial progenitor cells can also be delivered to the spinal cord.

Alternatively, the cells may be placed in a ventricle, e.g., a cerebral ventricle. Grafting cells in the ventricle may be accomplished by injection of the donor cells or by growing the cells in a substrate such as 30% collagen to form a plug of solid tissue which may then be implanted into the ventricle to prevent dislocation of the graft cells. For subdural grafting, the cells may be injected around the surface of the brain after making a slit in the dura.

Suitable techniques for glial cell delivery are described supra. In one embodiment, said preparation of glial progenitor cells is administered to the striatum, forebrain, brain stem, and/or cerebellum of the subject.

Delivery of the cells to the subject can include either a single step or a multiple step injection directly into the nervous system. Although adult and fetal oligodendrocyte precursor cells disperse widely within a transplant recipient's brain, for widespread disorders, multiple injections sites can be performed to optimize treatment. Injection is optionally directed into areas of the central nervous system such as white matter tracts like the corpus callosum (e.g., into the anterior and posterior anlagen), dorsal columns, cerebellar peduncles, cerebral peduncles. Such injections can be made unilaterally or bilaterally using precise localization methods such as stereotaxic surgery, optionally with accompanying imaging methods (e.g., high resolution MRI imaging). One of skill in the art recognizes that brain regions vary across species; however, one of skill in the art also recognizes comparable brain regions across mammalian species.

The cellular transplants are optionally injected as dissociated cells but can also be provided by local placement of non-dissociated cells. In either case, the cellular transplants optionally comprise an acceptable solution. Such acceptable solutions include solutions that avoid undesirable biological activities and contamination. Suitable solutions include an appropriate amount of a pharmaceutically-acceptable salt to render the formulation isotonic. Examples of the pharmaceutically-acceptable solutions include, but are not limited to, saline, Ringer's solution, dextrose solution, and culture media. The pH of the solution is preferably from about 5 to about 8, and more preferably from about 7 to about 7.5.

The injection of the dissociated cellular transplant can be a streaming injection made across the entry path, the exit path, or both the entry and exit paths of the injection device (e.g., a cannula, a needle, or a tube). Automation can be used to provide a uniform entry and exit speed and an injection speed and volume.

The number of glial progenitor cells administered to the subject can range from about $10^2$-$10^8$ at each administration (e.g., injection site), depending on the size and species of the recipient, and the volume of tissue requiring cell replacement. Single administration (e.g., injection) doses can span ranges of $10^3$-$10^5$, $10^4$-$10^7$, and $10^5$-$10^8$ cells, or any amount in total for a transplant recipient patient.

Since the CNS is an immunologically privileged site, administered cells, including xenogeneic, can survive and, optionally, no immunosuppressant drugs or a typical regimen of immunosuppressant agents are used in the treatment methods. However, optionally, an immunosuppressant agent may also be administered to the subject. Immunosuppressant agents and their dosing regimens are known to one of skill in the art and include such agents as Azathioprine, Azathioprine Sodium, Cyclosporine, Daltroban, Gusperimus Trihydrochloride, Sirolimus, and Tacrolimus. Dosages ranges and duration of the regimen can be varied with the disorder being treated; the extent of rejection; the activity of the specific immunosuppressant employed; the age, body weight, general health, sex and diet of the subject; the time of administration; the route of administration; the rate of excretion of the specific immunosuppressant employed; the duration and frequency of the treatment; and drugs used in combination. One of skill in the art can determine acceptable dosages for and duration of immunosuppression. The dosage regimen can be adjusted by the individual physician in the event of any contraindications or change in the subject's status.

EXAMPLES

The examples below are intended to exemplify the practice of embodiments of the disclosure but are by no means intended to limit the scope thereof.

Materials and Methods for Examples

Production of GPCs from human embryonic stem cells (hESCs). GPCs were generated from human embryonic stem cells (ESCs) using a previously described protocol (Wang et al., "Human iPSC-derived Oligodendrocyte Progenitor Cells can Myelinate and Rescue a Mouse Model of Congenital Hypomyelination," *Cell Stem Cell* 12:252-264 (2013); Windrem et al., "Human iPSC Glial Mouse Chimeras Reveal Glial Contributions to Schizophrenia," *Cell Stem Cell* 21:195-208 (2017), which are hereby incorporated by reference in their entirety), which is outlined in great methodological detail in the supplemental experimental procedures of Wang et al., "Human iPSC-derived Oligodendrocyte Progenitor Cells can Myelinate and Rescue a Mouse Model of Congenital Hypomyelination," *Cell Stem Cell* 12:252-264 (2013), which is hereby incorporated by reference in its entirety. Cells were harvested between 160-240, by which time the majority typically expressed the bipotential GPC marker CD140a, while the remainder were composed predominantly of A2B5$^+$/CD140a$^-$ immature astrocytes. No SSEA4 expressing cells were detectable. Human ES cells were obtained from GENEA, Inc. (Sydney, Australia), as lines GENEA02 and 19 (normal HTT: 15/18 CAG) and GENEA 17, 18 and 20 (mHTT: 40/12, 46/17 and 48/17 CAG, respectively) (Bradley et al., "Derivation of Huntington's Disease-Affected Human Embryonic Stem Cell Lines," *Stem Cells Dev* 20:495-502 (2011), which is hereby incorporated by reference in its entirety). GENEA02 and 17 are male, and GENEA18, 19, and 20 are female. Of note, GENEA 19 and 20 were donated and derived as a pair of female siblings, one normal and one with HD. The C27 control line is male.

Hosts. Homozygous shiverer mice (The Jackson Laboratory, Bar Harbor, ME) were crossed with homozygous rag2 null immunodeficient mice (Shinkai et al., "RAG-2-deficient Mice Lack Mature Lymphocytes Owing to Inability to Initiate V(D)J Rearrangement," *Cell* 68:855-867 (1992), which is hereby incorporated by reference in its entirety) on the C3h background (Taconic, Germantown, NY, USA) to generate shi/shi×rag2$^{-/-}$ myelin-deficient, immunodeficient mice (Windrem et al., "Neonatal Chimerization with Human Glial Progenitor Cells Can Both Remyelinate and Rescue the Otherwise Lethally Hypomyelinated Shiverer Mouse," *Cell Stem Cell* 2:553-565 (2008), which is hereby incorporated by reference in its entirety). Mice were maintained in a temperature and humidity-controlled housing (64-79° F.; 30%-70% humidity), in a pathogen-free colony room on a 12:12 hr light cycle. They were fed ad lib Mod LabDiet 5P00 with 0.025% trimethoprim/0.124% sulfamethoxyzole and autoclaved acid water (pH 2.5-3.0).

Suspensions of single-cells or small clusters of hESC-derived GPCs were spun down to 100,000 cells/ml. Neonates were anesthetized by cooling, and transplanted bilaterally in the corpus callosum with a total of 200,000 cells, as described (Windrem et al., "Fetal and Adult Human Oligodendrocyte Progenitor Cell Isolates Myelinate the Congenitally Dysmyelinated Brain," *Nat. Med.* 10:93-97 (2004), which is hereby incorporated by reference in its entirety). At 8, 12-13 or 18 weeks of age, the transplanted mice were anesthetized with pentobarbital, then perfusion fixed with cold HBSS followed by 4% paraformaldehyde. Brains were removed and post-fixed for 2 hr in cold paraformaldehyde.

All procedures were approved by the University of Rochester's Committee on Animal Resources (UCAR), under protocol 2004-129.

Cell preparation for transplantation. Prior to injection, flow cytometry was performed to confirm CD140a predominance in each culture. The suspended cell clusters were then collected from the well, spun down, and resuspended in a small volume of Ca$^{2+}$/Mg$^{2+}$ free HBSS. The resuspended clusters were transferred to a 100 mm cell culture dish, then cut with a no. 11 surgical scalpel to obtain pieces 100-200 mm in diameter. These fragments were then collected, spun down, washed with Ca$^{2+}$/Mg$^{2+}$-free HBSS, and resuspended to an approximate concentration of $10^5$ cells/ml in Ca$^{2+}$/Mg$^{2+}$-free HBSS.

Transplantation. Shiverer×Rag2 null neonatal mice were transplanted on postnatal day 1 or 2. Half of the litter was removed from the dam and placed in a humidified warming chamber. For this, a sterilized plastic box, lined with sterile gauze dampened with Hanks balanced salt solution, and warmed on a heating block, was used. The pups to be injected were then wiped with Povidone-Iodine and wrapped in sterile gauze to prevent direct contact with ice, then cryo-anesthetized for 2 to 6 minutes, depending on size. The pups were then removed from ice and cleaned with an alcohol prep pad, then laid in a customized neonatal mouse holder made of baked molded clay. The pups were injected directly through the skin and skull osteoid into both the rostral (AP+1.0 mm; ML±1.0 mm, ventral 1.0 mm) and caudal (AP−1.0, ML±1.0 mm, ventral 0.9 mm) corpus callosum. Following injections, pups were cleaned with alcohol prep pads and returned to the warming chamber for recovery. Upon recovery, the first half of the litter was returned to the dam, and the second half put in the humidified chamber. Pups were weaned between 21 and 28 days, then group housed.

Immunolabeling of tissue sections. Brains were cryopreserved, embedded in OCT (Tissue-Tek OCT, Sakura Finetek, Torrance, CA) and sectioned at 20 mm, either sagittally or coronally, on a cryostat. Human cells were identified with mouse anti-human nuclei, clone 235-1 at 1:800 (MAB1281; EMD Millipore, Billerica, MA). Oligodendrocytes were labeled with MBP with rat anti-MBP at 1:25 (Ab7349; Abcam, Cambridge, MA), astrocytes with anti-human-specific GFAP (SMI 21 at 1:1000, Covance, Princeton, NJ), and axons with mouse anti-neurofilament at 1:5000 (SMI-311) or 1:1000 (SMI-312; Covance, Princeton, NJ). Alexa Fluor secondary antibodies, goat anti-mouse and anti-rat 488, 568, 594, and 647 were used at 1:400 (Life Technologies, Carlsbad, CA).

Antibodies and Dilutions Used.

TABLE 5

Key Resources

| Reagent or Resource | Source | Identifier |
|---|---|---|
| Antibodies | | |
| Mouse monoclonal anti-human nuclei, 1:800 | Millipore | Cat #MAB1281; RRID: AB_94090 |
| Mouse monoclonal anti-human nuclei, conjugated with Alexa 488. 1:200 | Millipore | Cat #MAB1281A4 |
| Rat monoclonal anti-MBP, 1:25 | Abcam | Cat #ab7349; RRID: AB_305869 |
| Rabbit polyclonal anti-transferrin, 1:800 | Abcam | Cat #ab9538; RRID: AB_307325 |
| Mouse monoclonal anti-human GFAP, SMI 21R, 1:600 | Covance Research Products Inc. | Cat #SMI-21R-500; RRID: AB_509979 |
| Rabbit polyclonal anti-olig2, 1:500 | Neuromics | Cat #RA25017, 25081 |
| Mouse anti-neurofilament, smi-311, 1:5000 | Covance | Cat #SMI-311R-100, RRID: AB_509991 |
| Mouse anti-neurofilament, smi-312, 1:1000 | Covance | Cat #SMI-312R-100, RRID: AB_509993) |
| Goat anti-mouse IgG (H + L) Alexa Fluor 647, 1:400 | ThermoFisher Scientific | Cat #A-21235; RRID: AB_2535804 |
| Goat anti-mouse IgG1 Alexa Fluor 568, 1:400 | ThermoFisher Scientific | Cat #A-21124; RRID: AB 2535766 |
| Goat anti-mouse IgG1 Alexa Fluor 488, 1:400 | ThermoFisher Scientific | Cat #A-21121; RRID: AB_2535764 |
| Goat anti-Rabbit IgG (H + L) Alexa Fluor 568, 1:400 | ThermoFisher Scientific | Cat #A-11036; RRID: AB_2534094 |
| Goat anti-Rabbit IgG (H + L) Alexa Fluor 488, 1:400 | ThermoFisher Scientific | Cat #A-11034; RRID: AB_2576217 |
| Goat anti-Rat IgG (H + L) Alexa Fluor 568 | ThermoFisher Scientific | Cat #A-11077; RRID: AB_2534121 |
| Goat anti-Rat IgG (H + L) Alexa Fluor 488 | ThermoFisher Scientific | Cat #A-11006; RRID: AB_2534074 |
| Alexa Fluor 488-SSEA4 | Invitrogen | Cat #A14810; RRID: AB_2534323 |
| APC-conjugated mouse IgG1, Isotype Control | Miltenyi Biotec | Cat #130-092-214; RRID: AB_871704 |
| APC-mouse IgM, Isotype Control | Miltenyi Biotec | Cat #130-093-176; RRID: AB_871720 |
| APC-conjugated mAb A2B5 | Miltenyi Biotec | Cat #130-093-582; RRID: AB_10827602 |
| APC-conjugated anti-CD44 | Miltenyi Biotec | Cat #130-095-177; RRID: AB_10839563 |
| APC-conjugated anti-CD133/1 | Miltenyi Biotec | Cat #130-090-826; RRID: AB_244340 |
| PE-conjugated anti-CD140a | BD PharMingen | Cat #556002; RRID: AB_2650203 |
| Anti-olig2 | R&D Systems | Cat #AF2418; RRID: AB_2157554 |
| PE-conjugated mouse IgG2a, Isotype Control | BD PharMingen | Cat #555574; RRID: AB_395953 |
| Anti-PDGFRa | Cell Signaling Tech. | Cat #5241S; RRID: AB_10692773 |

TABLE 5-continued

| Key Resources | | |
|---|---|---|
| Reagent or Resource | Source | Identifier |
| Chemicals, Peptides, and Recombinant Proteins | | |
| bFGF | Sigma | Cat #F0291 |
| Biotin | Sigma | Cat #B4639 |
| Dibutyryl cAMP | Sigma | Cat #D0260 |
| Heparin | Fisher | Cat #NC9484621 |
| IGF-1 | R&D Systems | Cat #291-G1-050 |
| Laminin | Corning | Cat #354232 |
| NT3 | R&D Systems | Cat #267-N3-025 |
| PDGFaa | R&D Systems | Cat #221-AA-50 |
| Purmorphamine | Calbiochem | Cat #80603-730 |
| Retinoic acid | Sigma | Cat #R2625 |
| T3 | Sigma | Cat #T5516-1MG |
| Critical Commercial Assays | | |
| Custom TaqMan Array Card | Applied Biosystems | N/A |
| Ovation PicoSL WTA System V2 | NuGEN | Cat #3312 |
| RNeasy mini kit | QIAGEN | Cat #74104 |
| Taqman Universal master mix | Applied Biosystems | Cat #4304437 |
| TruSeq RNA Library Prep Kit V2 | Illumina | Cat #RS-122-2001 |
| Deposited Data | | |
| Raw RNA-seq data | GEO datasets | GEO accession number: GEO: GSE105041 |
| Processed RNA-seq data (count matrix) and R scripts for data analysis | This paper | |
| Lab-based interactive differential expression database | This paper | |
| Human reference genome NCBI build 38, GRCh38 | Genome Reference Consortium | |
| Mendeley dataset | This paper | |
| Experimental Models: Cell Lines | | |
| C27 iPSCs | Dr. Lorenz Studer, SKI | N/A |
| GENEA17 hESCs | Genea Biocells | |
| GENEA18 hESCs | Genea Biocells | |
| GENEA19 hESCs | Genea Biocells | |
| GENEA20 hESCs | Genea Biocells | |
| GENEA02 hESCs | Genea Biocells | |
| Experimental Models: Organisms/Strains | | |
| Mouse: C3Fe.SWV-Mbpshi/J | Jackson Laboratory | Cat #001428 |
| Mouse: C3H.129S6(B6)-Rag2tm1FwaN12 | Taconic | Cat #000602-M |
| Experimental Models: Housing | | |
| Temperature | 64° F.-79° F. | N/A |
| Relative Humidity Range | 30%-70% | N/A |
| Light-cycle | 12/12 | N/A |
| Water | Autoclaved acid water (pH 2.5-3.0) in sterile bottles | N/A |
| Cages and bedding | irradiated | N/A |
| Diet | Mod LabDiet 5P00 w/0.025% Trimethoprim/0.124% Sulfameth-5TK5 | N/A |
| Colony Room | Pathogen fee | N/A |
| Software and Algorithms | | |
| Photoshop CS6 | Adobe | N/A |
| Illustrator CS6 | Adobe | N/A |
| StereoInvestigator v11 | MBF Bioscience | N/A |
| Neurolucida 360 v2 | MBF Bioscience | N/A |
| Neurolucida Explorer v11 | MBF Bioscience | N/A |
| Leica Metamorph AP v2 | Leica Biosystems | N/A |
| Leica Application Suite X | Leica Biosystems | N/A |
| FlowJo | TreeStar | N/A |
| Trimmomatic (version 0.32) | Bolger et al., "Trimmomatic: a Flexible Trimmer for Illumina Sequence Data," Bioinformatics 30:2114-2120 (2014), which is | |

TABLE 5-continued

Key Resources

| Reagent or Resource | Source | Identifier |
|---|---|---|
| | hereby incorporated by reference in its entirety | |
| Subread (version 1.5.1) | Liao et al., "The Subread Aligner: Fast, Accurate and Scalable Read Mapping by Seed-and-Vote," Nucleic Acids Res. 41:e108 (2013), which is hereby incorporated by reference in its entirety | |
| featureCounts (version 1.5.1) | Liao et al., "The Subread Aligner: Fast, Accurate and Scalable Read Mapping by Seed-and-Vote," Nucleic Acids Res. 41:e108 (2013), which is hereby incorporated by reference in its entirety | |
| R | R Core Team, "R: a Language and Environment for Statistical Computing," R Foundation for Statistical Computing (2014), which is hereby incorporated by reference in its entirety | |
| RUVSeq (version 1.6.2) | Risso et al., "Normalization of RNA-seq Data Using Factor Analysis of Control Genes or Samples," Nat. Biotechnol. 32:896-902 (2014), which is hereby incorporated by reference in its entirety | |
| edgeR (version 3.14.0) | Robinson et al., "edgeR: a Bioconductor Package for Differential Expression Analysis of Digital Gene Expression Data," Bioinformatics 26:139-140 (2010), which is hereby incorporated by reference in its entirety | |
| DESeq2 (version 1.12.4) | Love et al., "Moderated Estimation of Fold Change and Dispersion for RNA-seq Data with DESeq2," Genome Biol. 15:550 (2014), which is hereby incorporated by reference in its entirety | |
| ToppCluster | Kaimal et al., "ToppCluster: a Multiple Gene List Feature Analyzer for Comparative Enrichment Clustering and Network-based Dissection of Biological Systems," Nucleic Acids Res. 38: W96-W102 (2010), which is hereby incorporated by reference in its entirety | |
| Gephi (version 0.9.1) | Bastian et al., "Gephi: an Open Source Software for Exploring and Manipulating Networks," Proc. Third Intl. ICWSM Conf. 3:361-362 (2009), which is hereby incorporated by reference in its entirety | |
| Ingenuity Pathway Analysis | QIAGEN | |
| ExpressionSuite Software (version 1.1) | Applied Biosystems | |

Other

| | | |
|---|---|---|
| Agilent Bioanalyzer | Agilent | N/A |
| BD FACS Aria IIIU | BD Biosciences | N/A |
| HiSeq 2500 | Illumina | N/A |
| Nanodrop 1000 spectrophotometer | Nanodrop | N/A |
| Olympus IX71 Inverted Microscope | Olympus | N/A |
| QuantStudio 12K Flex Real-Time PCR | Applied Biosystems | N/A |
| Cryostat | Hacker Instruments | Model OTF |

TABLE 5-continued

Key Resources

| Reagent or Resource | Source | Identifier |
| --- | --- | --- |
| Cryostat | Leica Biosystems | Cat #CM3050S |
| Vibratome | Vibratome | 1000 Plus |
| Disposable microtome blades | C.L. Sturkey | Cat #DT315G50 |
| PTFE coated stainless steel blades | Ted Pella Inc | Cat #121-6 |
| Surgipath X-tra precleaned micro slides | Leica Biosystems | Cat #38002002 |
| DMi8 | Leica Biosystems | N/A |
| DM6000B | Leica Biosystems | N/A |
| DFC 360 FX camera | Leica Biosystems | N/A |
| BX51 | Olympus | N/A |
| DP30BW camera | Olympus | N/A |
| Orca-R2 Digital CCD Camera | Hamamatsu | Cat #C10600-10B |
| MAC 5000 | Ludl Electronic Prods. | Cat #73005001 |
| Focus DR Linear encoder | Ludl Electronic Prods. | Cat #99A420 |
| STG 4" × 3" Stepper | Ludl Electronic Prods. | Cat #99S100LE2MBF |

RNA-seq. hGPCs assessed for gene expression were first sorted by fluorescence-activated cell sorting on the basis of the cell surface marker CD140a (BD PharMingen), as described (Sim et al., "CD140a Identifies a Population of Highly Myelinogenic, Migration-competent and Efficiently Engrafting Human Oligodendrocyte progenitor Cells," Nat. Biotechnol. 29:934-941 (2011), which is hereby incorporated by reference in its entirety), using a FACS Aria IIIu (Becton Dickinson) (FIG. 3). The mRNA was isolated by polyA-selection protocol from FACS-sorted PDGFRa-positive GPC lines produced from human embryonic stem (ES) cells derived from 3 HID patients (designated to HID lines 17 [N=5 independent cell set preparations], 18 [N=5], and 20 [N=6]) and 2 healthy controls (designated to CTR lines 02 [N=6], and 19 [N=6], sibling of HD20). Sequencing libraries were prepared with the Illumina TruSeq RNA v2 kit and sequenced on an Illumina HiSeq 2500 sequencer, yielding approximately 45 million 100-bp single-end reads per sample for all cell lines except for control line CTR02, which was sequenced to similar depth but in 125-bp paired-end read mode. The sequencing reads were then pre-processed by trimming off adaptor and low-quality sequences using Trimmomatic (Bolger et al., "Trimmomatic: a Flexible Trimmer for Illumina Sequence Data," Bioinformatics 30:2114-2120 (2014), which is hereby incorporated by reference in its entirety). The quality of reads before and after pre-processing was assessed with FastQC. The pre-processed reads were then aligned to the RefSeq NCBI reference human genome version GRCh38 (Pruitt et al., "NCBI Reference Sequences (RefSeq): a Curated Non-Redundant Sequence Database of Genomes, Transcripts and Proteins," Nucleic Acids Res. 35:D61-D65 (2007), which is hereby incorporated by reference in its entirety), with Subread read aligner (Liao et al., "The Subread Aligner: Fast, Accurate and Scalable Read Mapping by Seed-and-Vote," Nucleic Acids Res. 41:e108 (2013), which is hereby incorporated by reference in its entirety). Raw gene counts were obtained from BAM alignment files with featureCounts (Liao et al., "featureCounts: an Efficient General Purpose Program for Assigning Sequence Reads to Genomic Features," Bioinformatics 30:923-930 (2014), which is hereby incorporated by reference in its entirety).

SOX10/MYRF rescue of myelination. For this set of experiments, SOX10 and MYRF transcripts were cloned in two separate lentiviral vectors: pTANK-TRE-MYRF-CAG-rtTA3G-WPRE and pTANK-TRE-Sox10-P2A-DC4-WPRE. In this Tet-On system, the cell surface expression of the selectable marker CD4 requires the expression from both viruses, thus ensuring co-expression of the MYRF and SOX10 transgenes. Virus particles pseudotyped with vesicular stomatitis virus G glycoprotein were produced, concentrated by ultracentrifugation, and titrated on 293HEK cells. G20 hGPC cultures were infected at 1.0 MOI in glial media. Cells were washed with HBSS and maintained in glial media supplemented with 1 mg/ml DOX (Millipore-Sigma St. Louis, MO) for 4 days. hGPCs were then selected for membrane expression of CD4 using MACS (Miltenyi, Germany) as described (Windrem et al., "Neonatal Chimerization with Human Glial Progenitor Cells Can Both Remyelinate and Rescue the Otherwise Lethally Hypomyelinated Shiverer Mouse," Cell Stem Cell 2:553-565 (2008), which is hereby incorporated by reference in its entirety).

Rescue of oligodendrocytic differentiation in vitro. MACS isolated CD4$^+$ cells were allowed to attach overnight in glial media (Wang et al., "Human iPSC-derived Oligodendrocyte Progenitor Cells can Myelinate and Rescue a Mouse Model of Congenital Hypomyelination," Cell Stem Cell 12:252-264 (2013), which is hereby incorporated by reference in its entirety). DOX was maintained in overexpression conditions throughout the differentiation induction. The next day, cells were washed once in HBSS and transitioned to differentiation media (Neurobasal medium (GIBCO), 1×N2 (Thermo Fisher), 1×B27 (Thermo Fisher), 1× GlutaMAX (Thermo Fisher), 20 ng/ml BDNF (R&D Systems), 0.2 mM L-Ascorbic Acid (Sigma), 60 ng/ml T3 (Sigma), 0.2 mM dibutyrl cyclicAMP (Sigma), 100 ng/ml biotin (Sigma), 1× insulin-transferrin-selenium (ThermoFisher), 10 ng/ml NT3 (R&D), and 100 ng/ml IGF1 (R&D). Media were changed every other day for 2 weeks before fixation. Oligodendrocyte differentiation was quantified via O4 immunostaining.

Rescue of oligodendrocytic differentiation in vitro. Cells were prepared for transplantation and then injected into the corpus callosa of neonatal shiverer mice, at 2 sites unilaterally. Starting at 9 weeks of age, half of the transplanted mice were administered either DOX (2 mg/ml with 5% sucrose in water (Chow et al., "A Doxycycline-Inducible, Tissue-Specific Aromatase-Expressing Transgenic Mouse," Transgenic Res. 21:415-428 (2012), which is hereby incorporated by reference in its entirety) or normal drinking water in their water bottles, for 5 weeks. Both control and experimental mice were then sacrificed at 13 weeks of age and prepared for immunolabeling for MBP and human nuclear antigens, then imaged by confocal to assess axonal ensheathment by MBP-expressing oligodendrocytes as described.

Imaging and quantitative histology. To map the distribution of human nuclei, sections were imaged on a Nikon Instruments Ni-E equipped with Nikon Digital Sight Camera DS-Fi1, and counts scored in Nikon NIS Elements v4.5. For photographing the distribution of myelin at low power, whole brain sections were imaged on a Leica LMD 6500. Higher power confocal images of myelin ensheathment were obtained using a Nikon C2+ confocal, and images were acquired with a 100× objective using 0.2 mm steps. Imaging for cell type-specific markers was performed on an Olympus BX51 using a Hammamatsu camera driven by Stereo Investigator software (MBF, Williston, VT). Higher magnification confocal stacks of astrocytes subjected to Sholl analysis were obtained using a Leica SP8 confocal.

Cell counting. Quantification of donor cell density in the corpus callosum was based on counts of 1 mm lateral from midline. Randomly initiated, uniformly sampled coronal sections of the brains were labeled for human nuclei, DAPI and other phenotype-specific markers (Olig2, hGFAP, TF and MBP). For Olig2 and hGFAP quantification, the regions of interest of each section were imaged using an Olympus BX51 equipped with a Hamamatsu camera, at 40×. Z stacks were obtained with a step size of 1 mm. For TF and MBP quantification, the regions of interest were imaged using a Nikon Ni-E Eclipse microscope equipped with a DS-Fi1 camera, at 20×. Z stacks were obtained with a step size of 0.7-1 mm. Immunolabeled cells were counted using high intensity projection of the z stacked images on three evenly-spaced coronal sections from each mouse, in Nikon NIS Elements v.4.5.

Astrocyte morphometrics. Shiverer×rag2 null mice were sacrificed at 18 weeks of age and their white matter astrocyte morphologies assessed. 150 mm thick coronal slices were taken by Vibratome at Bregma −1.0 mm from control (GENEA19) or HD (GENEA20) hGPC-engrafted mice, incubated in mouse anti-hGFAP for 1 week at 4° C., then 4 hr in Alexa 568 goat anti-mouse antisera. The slices were mounted on slides and imaged at 100× by confocal (Leica SP8). The images were traced using Neurolucida 360 (MicroBrightfield, Inc.); all tracings were done by experimenters blinded as to the treatment condition.

Individual astrocytes were selected from the middle of the corpus callosum at mid-depth so as to capture cells and their processes in their entirety. Cells were analyzed by Neurolucida with Sholl analysis, as 3 cells/slice and 3 slices/brain, taken at 500, 1000, and 1500 mm lateral of the midline. A total of 14 neonatally-engrafted brains (GENEA18, n=21 cells/3 brains; GENEA19, 32 cells/4 brains; GENEA20, 42 cells/7 brains) were assessed, yielding 63 traced mHTT astrocytes (GENEA18- and 20-derived), and 32 control (GENEA19) astrocytes. For Sholl analysis, concentric shells placed at successively increasing diameters of 5 mm were centered on the cell body, and the number of intersections between cell processes and shells counted (Sholl, "Dendritic Organization in the Neurons of the Visual and Motor Cortices of the Cat," *J. Anat.* 87:387-406 (1953), which is hereby incorporated by reference in its entirety). For the assessment and quantitative description of astrocytic fiber 3D architecture, Fan-in analysis (MBF Biosciences) was used as previously described for studies of dendritic topology (Dang et al., "Formoterol, a Long-Acting β2 Adrenergic Agonist, Improves Cognitive Function and Promotes Dendritic Complexity in a Mouse Model of Down Syndrome," *Biol. Psychiatry* 75:179-188 (2014), which is hereby incorporated by reference in its entirety).

Myelin luminance analysis. To measure forebrain myelination, luminance analysis based on measurement of MBP immunofluorescence was used. Evenly-spaced and uniformly sampled coronal sections were stained for MBP as described, and images taken at 10× using a Nikon Ni-E and Nikon DS-Fi1 camera. The corpus callosum was selected as region of interest, and mean intensity values were obtained using NIS Elements v.4.5.

Statistical analysis of histological data. All analyses were done with Prism® v.7 (GraphPad Software) using two-way ANOVA and post hoc Bonferroni t tests. Statistical significance was considered as P-values less than 0.05. Significances were represented as $*p<0.05$, $p<0.01$ and $*p<0.001$. Graphs and figures were made and assembled with Prism 7, and all data are shown as mean±standard error of the mean (SEM).

Bioinformatics. After examining principal component and hierarchical clustering plots generated with native R functions (R Core Team, "R: a Language and Environment for Statistical Computing," R Foundation for Statistical Computing (2014), which is hereby incorporated by reference in its entirety), one mis-clustered outlier sample was removed from analysis in line HD17 (GENEA17), as were 2 outliers in lines HD20 (GENEA20) and CTR19 (GENEA19). After eliminating lowly expressed transcripts leaving those with a count of at least 5 reads in more than 3 samples, the count data were normalized using RUVSeq (Risso et al., "Normalization of RNA-seq Data Using Factor Analysis of Control Genes or Samples," *Nat. Biotechnol.* 32:896-902 (2014), which is hereby incorporated by reference in its entirety). The R Bioconductor package (Gentleman et al., "Bioconductor: Open Software Development for Computational Biology and Bioinformatics," *Genome Biol.* 5:R80 (2004), which is hereby incorporated by reference in its entirety)) was used to account for variance. As described in the RUVSeq documentation, normalization was accomplished in the following three-step procedure: 1) negative in silico control genes were determined by first-pass differential expression analysis by edgeR (Robinson et al., "edgeR: a Bioconductor Package for Differential Expression Analysis of Digital Gene Expression Data," *Bioinformatics* 26:139-140 (2010), which is hereby incorporated by reference in its entirety) and DESeq2 (Love et al., "Moderated Estimation of Fold Change and Dispersion for RNA-seq Data with DESeq2," *Genome Biol.* 15:550 (2014), which is hereby incorporated by reference in its entirety) R Bioconductor packages, including those genes with FDR-adjusted p values>0.75, as calculated by both methods; 2) the negative in silico control genes were then used in the RUVg function of RUVSeq to calculate variance factors; and 3) the second-pass differential expression analysis (1% FDR and log 2 fold-change>1) was performed to determine disease-dysregulated genes, using the original raw counts, and adjusting for RUVg-calculated variance factors by multifactor GLM models implemented in both the edgeR and DESeq2 packages.

This three-step analysis, with filtering out low- and non-expressed transcripts, was used to compare each HD-derived hGPC cell line to the pooled CTR-derived hGPCs, as well as for the sibling pair comparison of HD20 versus HD19. In all comparisons, one RUVg-calculated variance factor was used. The intersection of the resulting four lists of differentially expressed genes was taken as the conserved representative list of HD-dysregulated genes. To obtain average FCs and p values for dysregulated genes in all three HD-derived GPC lines, a differential expression comparison of pooled HD to pooled CTR lines was performed by the same workflow with the same number of variance factors.

For all comparisons of differential expression, only the significant results that agreed between edgeR and DESeq2 were used in downstream analysis. Fold-changes and FDR-adjusted p values reported in the Results were calculated by edgeR. Functional annotation of the conserved set of HD-dysregulated genes was performed using ToppCluster (Kaimal et al., "ToppCluster: a Multiple Gene List Feature Analyzer for Comparative Enrichment Clustering and Network-based Dissection of Biological Systems," *Nucleic Acids Res.* 38:W96-W102 (2010), which is hereby incorporated by reference in its entirety) and Ingenuity Pathway Analysis (IPA) (QIAGEN) (Kramer et al., "Causal Analysis Approaches in Ingenuity Pathway Analysis," *Bioinformatics* 30:523-530 (2014), which is hereby incorporated by reference in its entirety).

TaqMan RT-qPCR arrays for gene expression validation. Extracted total RNA was amplified using ribo-SPIA based whole transcriptome based amplification (NuGen). The expression of cell type markers and pathway-specific genes was assessed by real-time polymerase chain reaction (RT-PCR) using a 48-gene Taqman low-density array (TLDA) (Applied Biosystems). The relative abundance of transcript expression was calculated by DDCt analysis, and the expression data normalized to the mean of 18S and GAPDH as endogenous controls. The difference of expression in HD and control GPCs was assessed by paired t test followed by multiple testing correction by Benjamini-Hochberg (BH) procedure (Benjamini and Hochberg, "Controlling the False Discovery Rate: a Practical and Powerful Approach to Multiple Testing," *J. R. Stat. Soc. Series B Stat. Methodol.* 57:289-300 (1995), which is hereby incorporated by reference in its entirety). Analysis of TLDA data was performed in ExpressionSuite Software version 1.1 supplied by Applied Biosciences.

SOX10/MYRF rescue of myelinogenic gene expression. Both mHTT and normal sibling hESC-derived hGPCs were transfected with plasmids expressing either SOX10 and MYRF in tandem, under the regulatory control of the constitutive promoter EF1α (pTANK-EF1α-Sox10-P2A-Myrf-T2A-EGFP-WPRE), or a control plasmid expressing only EGFP (pTANK-EF11α-EGFP-WPRE). Transfection was performed using Nucleofector (Lonza, Germany), using the CA205 transfection program in P3 buffer following the manufacturer's protocol. Cells were collected 72 hours after transfection for RT-qPCR of potential SOX10 and MYRF target genes. RNA was extracted using the Qiagen RNeasy Micro Kit (Qiagen, Germany). The first-strand cDNA was synthetized using TaqMan Reverse Transcription Reagents (Applied Biosystems). 5 ng of RNA input was used for each reaction; these were performed using FastStart Universal SybrGreen Mastermix (Roche Diagnostics, Germany), on a real-time PCR instrument (CFX Connect Real-Time System thermocycler; Bio-Rad, USA). Samples from G19- and G20-derived hGPCs were each assayed in triplicate for each target gene assayed (primers available in Table 6 below).

TABLE 6

Primers used for real time PCR

| Target | Forward primer | Reverse primer |
|---|---|---|
| LINGO1 | ACCTTCGCTTTCATCTCCAAC (SEQ ID NO: 1) | CGATGATGAGGGTCTTGATGTC (SEQ ID NO: 2) |
| MAG | GGACCCTATTCTCACCATCTTC (SEQ ID NO: 3) | CACACCAGTACTCTCCATCATC (SEQ ID NO: 4) |
| MBP | CGGAGTTGTGCACGTAGTAG (SEQ ID NO: 5) | ATCTTCACACAGAAAGGGACAG (SEQ ID NO: 6) |
| MOG | CGAATCACGAGGTCAGGAGT (SEQ ID NO: 7) | GCCCACCACTATGCTCAGTT (SEQ ID NO: 8) |
| MYRF (3'UTR) | ACACTGGATGCAATGGTGTTA (SEQ ID NO: 9) | CAGCAACTCCAGTGTGAAGA (SEQ ID NO: 10) |
| MYRF (cDNA) | CATCCTGTCCTTCCGTGAAT (SEQ ID NO: 11) | GAAGTGGAAGTGGTAGTCTGTG (SEQ ID NO: 12) |
| NKX2.2 | TTTATGGCCATGTAAACGTTCTG (SEQ ID NO: 13) | GCAACAATCACCACCGATATT (SEQ ID NO: 14) |
| OLIG2 | GTGGGAGACTCCGGGTA (SEQ ID NO: 15) | TGAGATTGGATATGACCATCAGC (SEQ ID NO: 16) |
| OMG | GAGGGAAGAGACAACCACAAATG (SEQ ID NO: 17) | GACCACAACATTGAGCAATAAGAG (SEQ ID NO: 18) |
| PDGFRA | GAGGAGGACTTGGTTGATGTT (SEQ ID NO: 19) | TGAGATGCTACTGAGGCATTG (SEQ ID NO: 20) |
| PLP1 | GTGGCTCCAACCTTCTGTCC (SEQ ID NO: 21) | GCAGGGAAACCAGTGTAGC (SEQ ID NO: 22) |
| SOX10 (3'UTR) | CCAGTTTGACTACTCTGACCA (SEQ ID NO: 23) | TATAGGAGAAGGCCGAGTAGAG (SEQ ID NO: 24) |
| SOX10 (cDNA) | AGGAATGACCCTCTATCCCA (SEQ ID NO: 25) | GCATGTCAGACCCTCACTATC (SEQ ID NO: 26) |

TABLE 6-continued

Primers used for real time PCR

| Target | Forward primer | Reverse primer |
|---|---|---|
| TF | TGTGGTCACACGGAAAGATAAG (SEQ ID NO: 27) | GTCAGTTACGTTGCTTCCAAATAG (SEQ ID NO: 28) |

Melting-curve analysis was performed after each PCR to confirm the specificity of the reaction, and to identify the peaks of interest in all samples. Results were normalized to the expression level of 18S from the same sample.

Data and software availability. All raw RNA-seq data have been deposited to GEO, accession number GEO: GSE105041. The complete reproducible workflow, including R scripts and count matrix, was deposited also. All differential expression data have been uploaded to a publicly accessible, interactive lab-based website, within which further evaluation and interrogation of differentially expressed gene sets may be performed by interested users. All data have also been uploaded to Mendeley Data.

Network Visualization and Analysis. The ToppCluster annotation tool was used for its ability to represent term to gene associations as a network (Kaimal et al., "ToppCluster: a Multiple Gene List Feature Analyzer for Comparative Enrichment Clustering and Network-Based Dissection of Biological Systems," *Nucleic Acids Res.* 38:W96-W102 (2010), which is hereby incorporated by reference in its entirety). The annotation results were exported with ToppCluster's Network Generator as a list of term to gene associations representing network edges. For all subsequent network visualizations and analyses, the term to gene association networks were imported into Gephi graph visualization software (Jacomy et al., "ForceAtlas2, a Continuous Graph Layout Algorithm for Handy Network Visualization Designed for the Gephi Software," *PLoS ONE* 9:e98679 (2014), which is hereby incorporated by reference in its entirety). Basic node centrality measures and node degrees were calculated and the networks were arranged with Force Atlas layout using default parameters. Closely interconnected node modules were determined with the built-in community detection algorithm (Blondel et al., "Fast Unfolding of Communities in Large Networks," arXiv arXiv:0803.0476 (2008), which is hereby incorporated by reference in its entirety), using a randomization and resolution parameter of 1.3 for CD140a-derived, and 2.0 for CD44-derived annotation networks, so as to optimize both the grouping and number of communities.

Figure 1A:
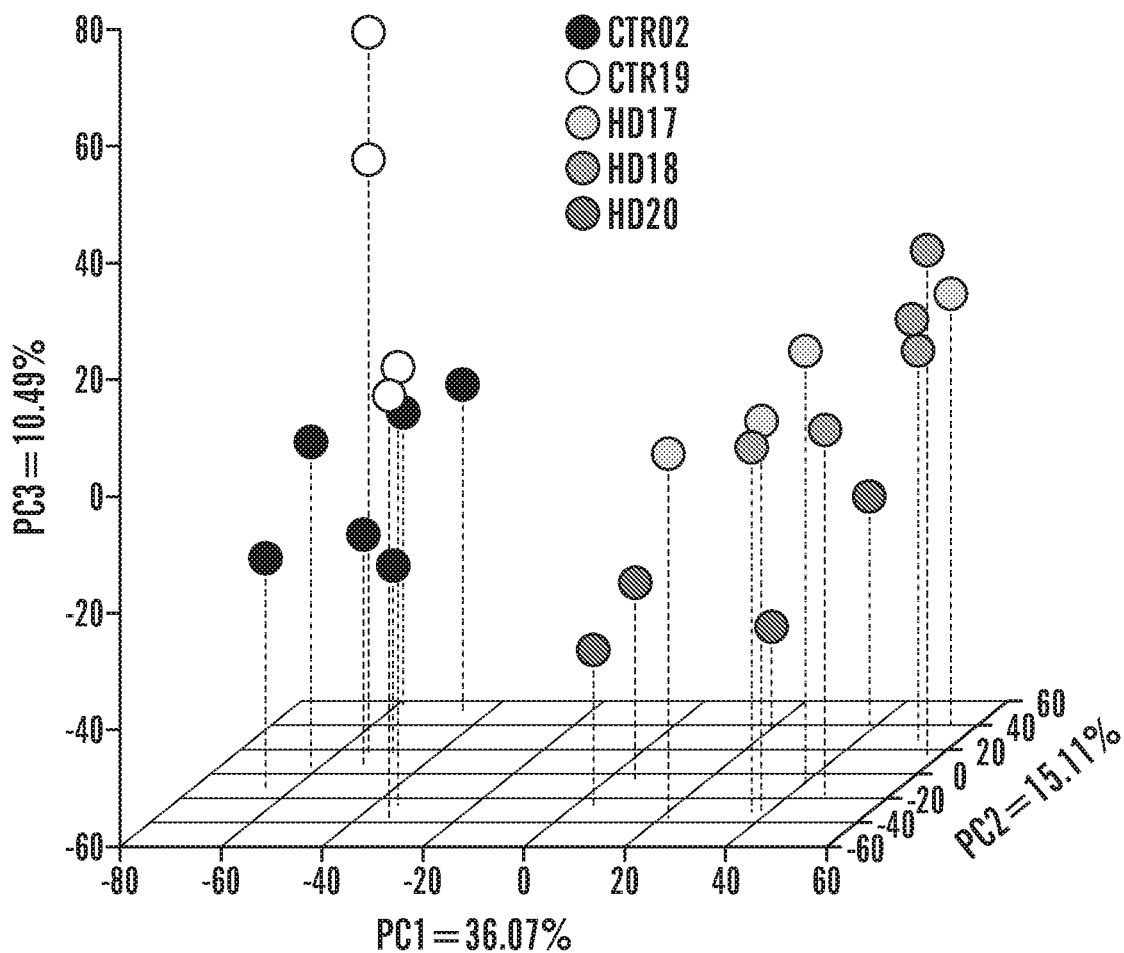
FIGS. 1A-1G show HD hESC-derived hGPCs display profound mHTT-dependent changes in gene expression.
Figure 1B:
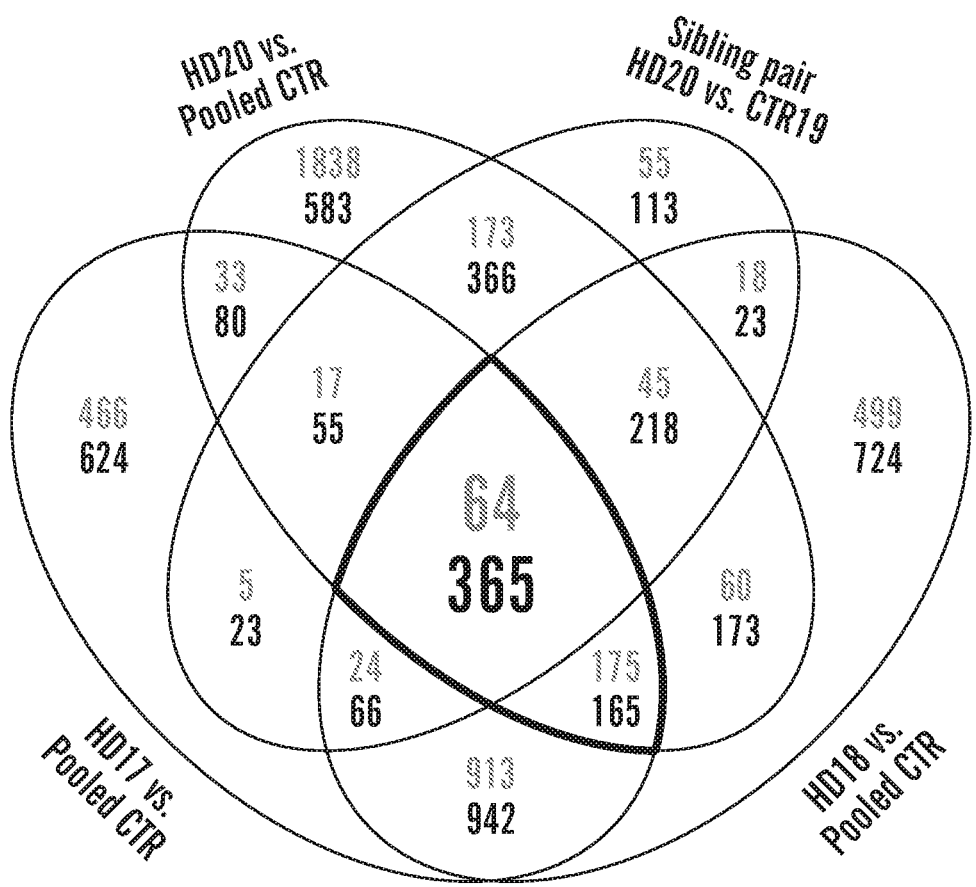
Figure 1C:
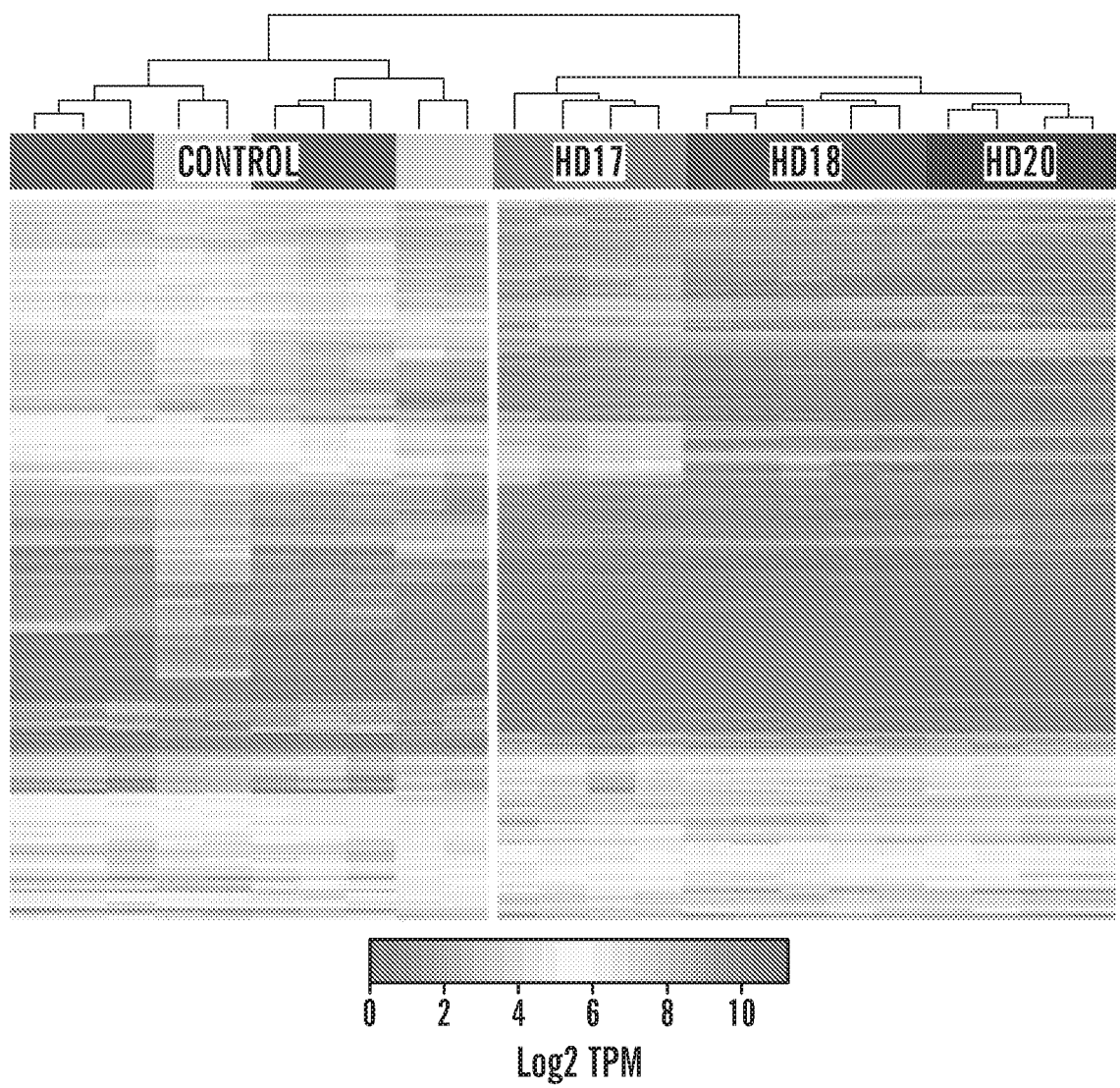

Example 1—mHTT OPCs Down-Regulate Transcriptional Determinants of Glial Lineage Progression To address the role of glial transcriptional abnormalities in the pathogenesis of HD, the differential gene expression by bipotential hGPCs derived from huntingtin mutant hESCs was first assessed. To that end, GPCs from three distinct lines of hESCs derived from mHTT-expressing blastocysts (GENEA17, GENEA18, and GENEA20; GENEA Biocells) and from two control lines (GENEA02 and GENEA19) (Bradley et al., "Derivation of Huntington's Disease-Affected Human Embryonic Stem Cell Lines," *Stem Cells Dev* 20:495-502 (2011), which is hereby incorporated by reference in its entirety) were generated and purified. GPCs were produced from hESCs using previously described methods (Wang et al., "CD133/CD140a-Based Isolation of Distinct Human Multipotent Neural Progenitor Cells and Oligodendrocyte Progenitor Cells," *Stem Cells and Development* 22:2121-2131 (2013), which is hereby incorporated by reference in its entirety), followed by CD140a-based FACS to isolate the resulting GPC fraction (>99% CD140a*) (Sim et al., "CD140a Identifies a Population of Highly Myelinogenic, Migration-Competent and Efficiently Engrafting Human Oligodendrocyte Progenitor Cells," *Nature Biotechnology* 29:934-941 (2011), which is hereby incorporated by reference in its entirety). Importantly, one of the controls (GENEA19; 18 CAG) was a sibling to one of the mHTT-expressing lines (GENEA20; 48 CAG); these lines, donated by the same parents, were fraternal female twins.

mHTT and control hGPCs were harvested as stably expanding hGPCs after average propagation times of 190±16 and 174±14 days, respectively. Flow cytometry revealed that 54%±3.4% of normal cells (GENEA02 and GENEA19; n=12 culture runs) and 44%±3.3% of Huntingtin mutant cells (GENEA17, 18 and 20; n=16) expressed CD140a at these time points (means±SEM). The CD140a fraction of each culture was then isolated to near purity by FACS, and RNA-seq was performed using an Illumina HiSeq 2500 sequencer, which showed profound transcriptional dysregulation in the hGPCs derived from the three HD lines relative to the pooled control hESC GPCs. Principal-component analysis (PCA) showed clear segregation of the mHTT-expressing and control hGPCs (FIG. 1A). As a group, using a 2-fold change (FC) cutoff and 1% false discovery rate (FDR), 239 genes were upregulated and 530 genes were downregulated in the mHTT hGPCs relative to their controls (FIG. 1). To further refine the resultant list of differentially expressed genes, the differential expression of GENEA20 (mHTT)-derived hGPCs was then compared to their sibling GENEA19-derived controls and added that sibling comparison to the overall comparison; this acted as an additional filter and yielded a tighter differentially expressed gene list composed of 64 upregulated and 365 downregulated genes in hGPCs derived from all HD-derived hGPC cell lines relative to their pooled control hGPCs (FIGS. 1B and 1C).

Figure 1D:
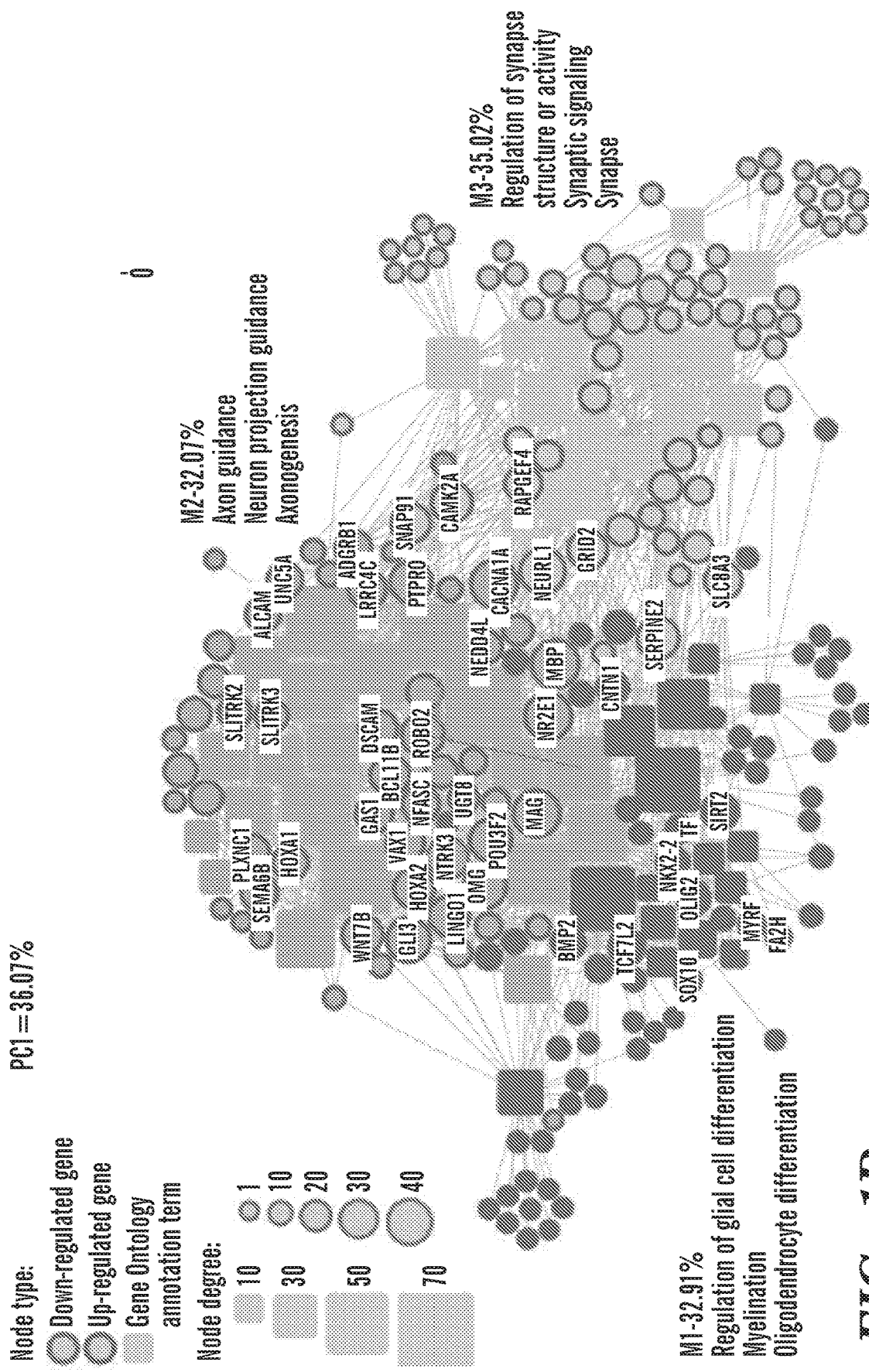
Figure 1E:
Figure 1F:
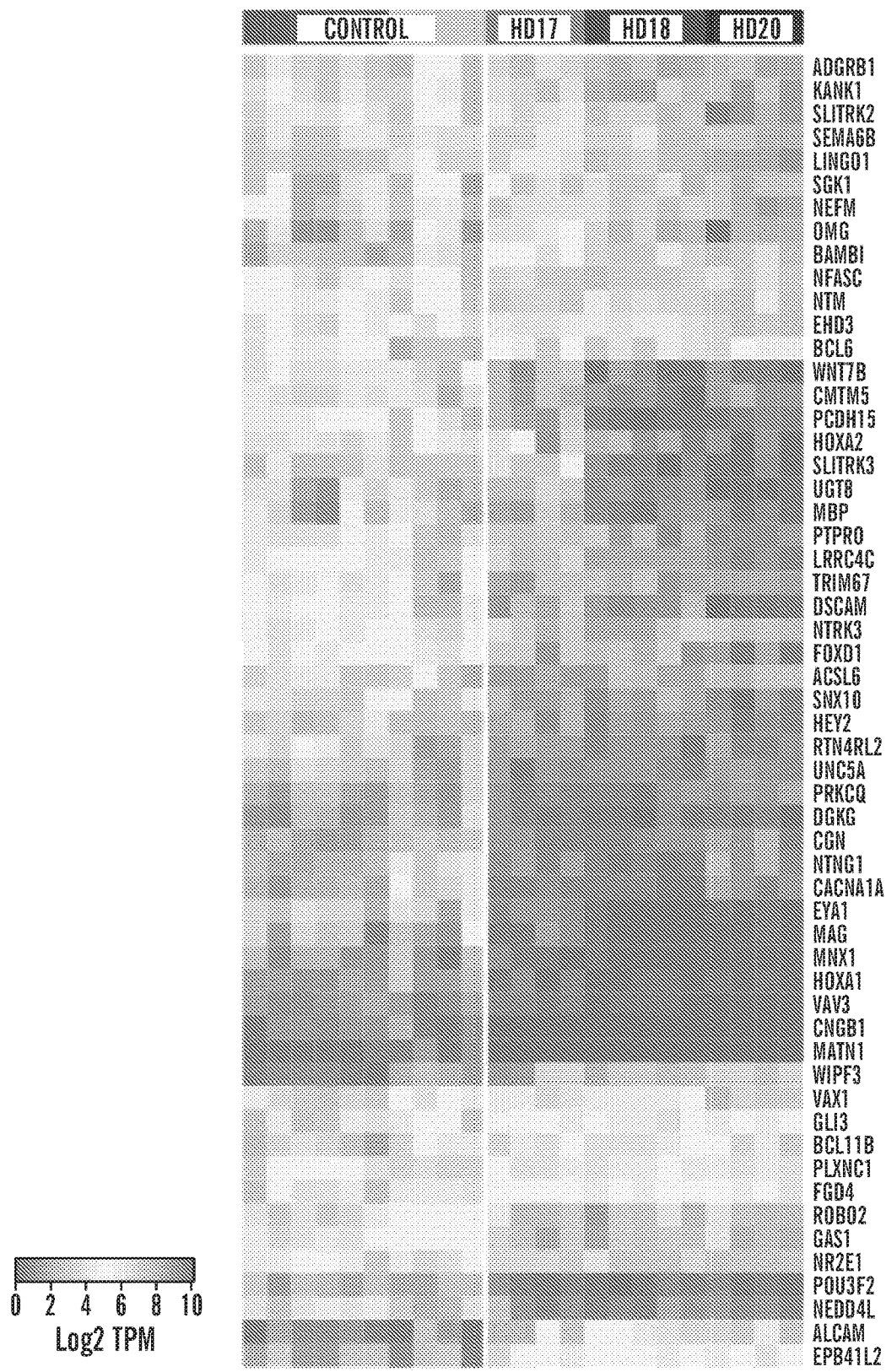
Figure 1G:
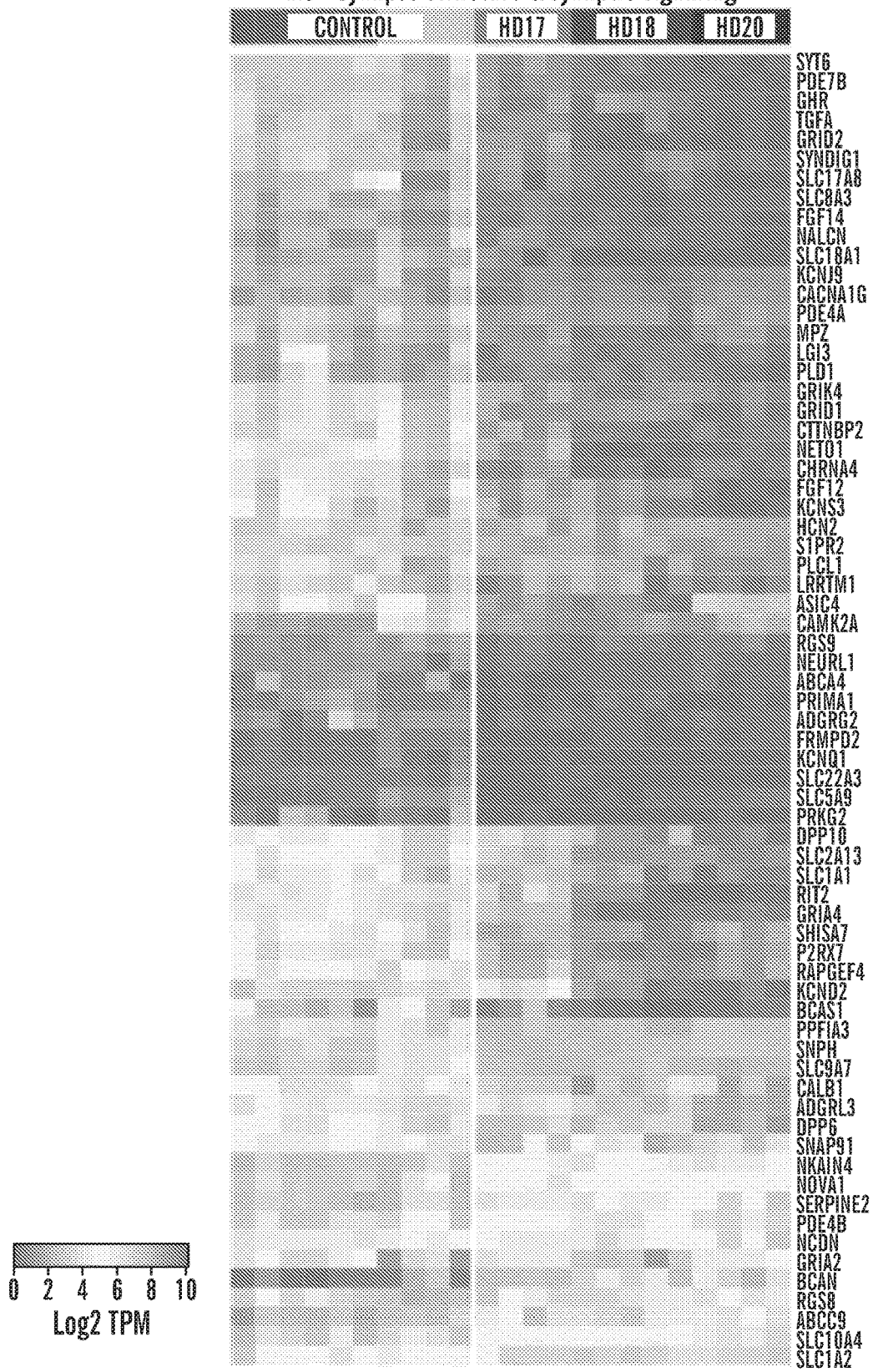
Figure 2A:
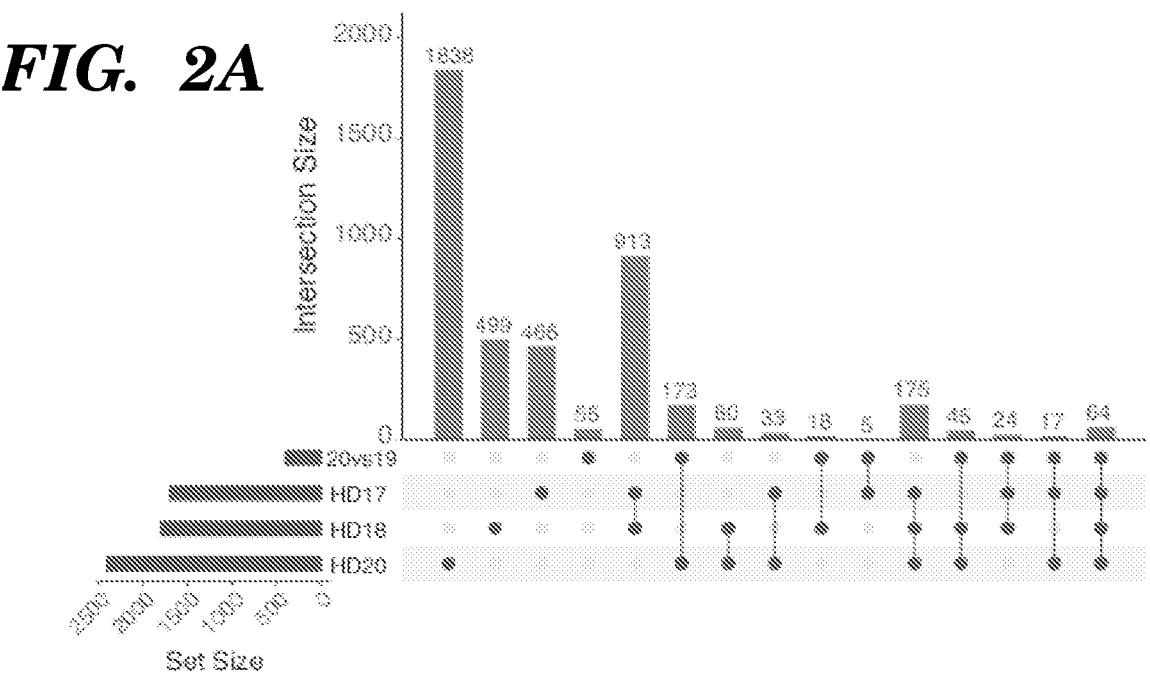
FIGS. 2A-2D show genes differentially-expressed between hGPCs derived from different HD hESCs vs. pooled controls.
Figure 2B:
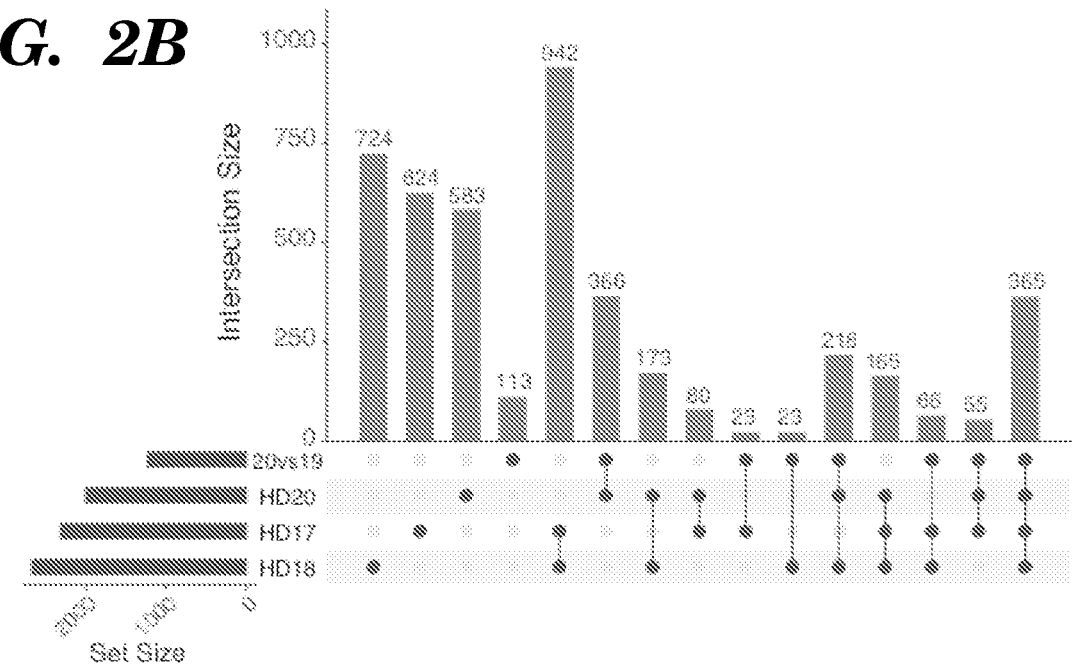
Figure 2C:
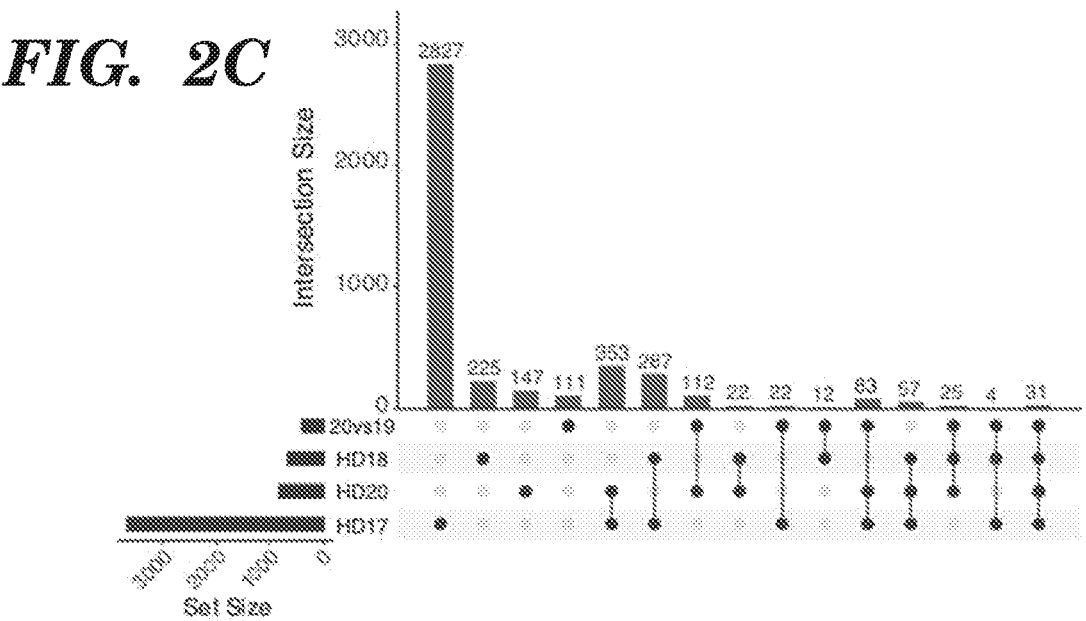
Figure 2D:
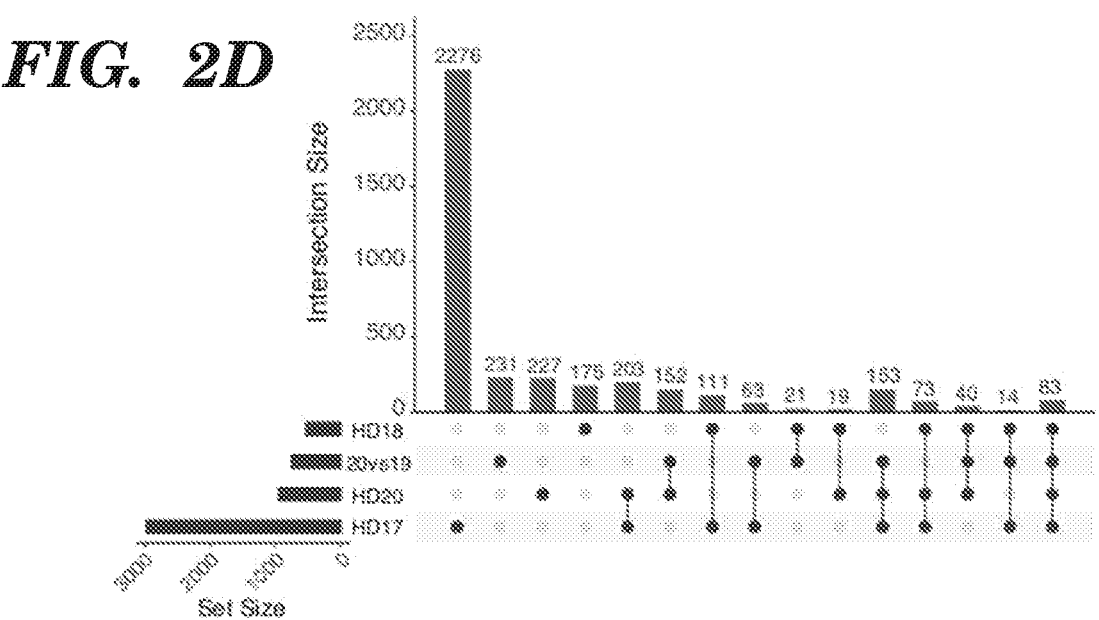
Figure 3A:
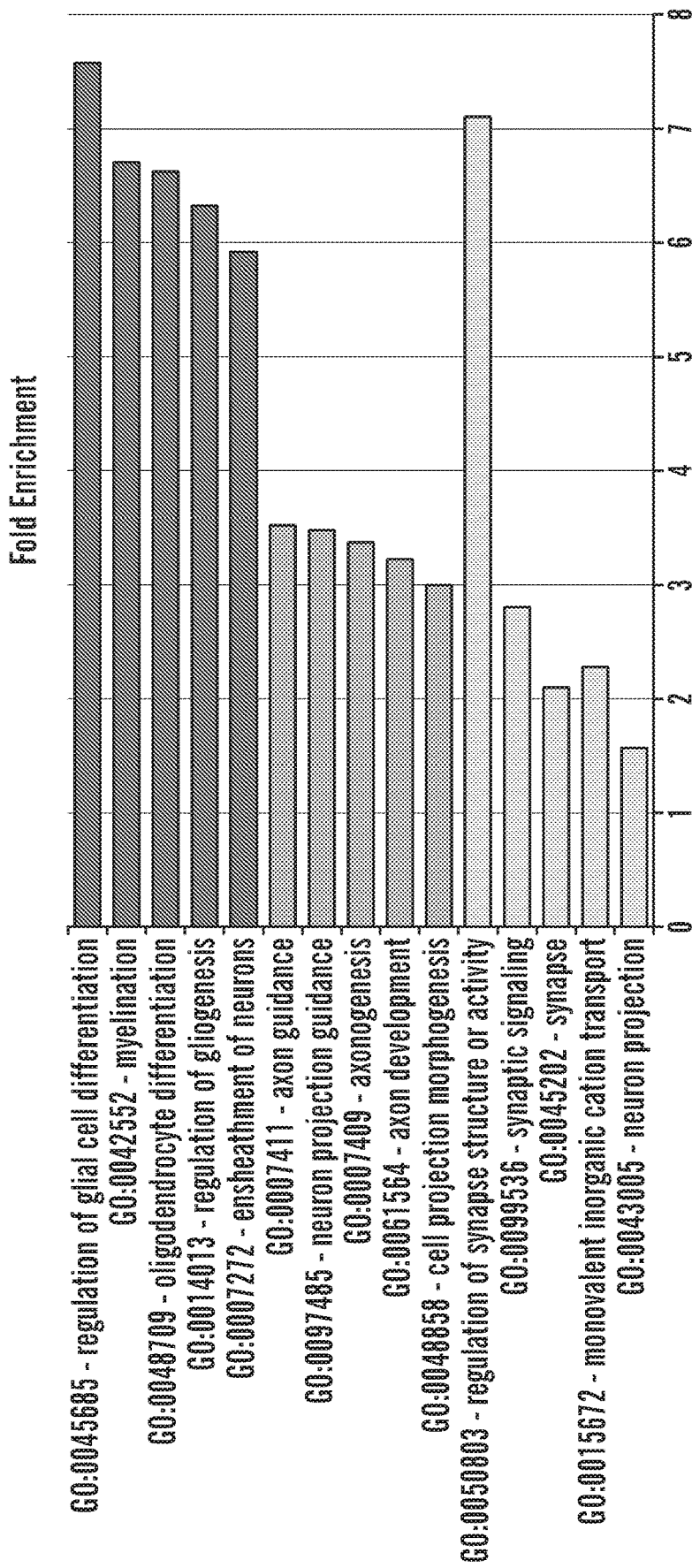

Using this gene set, functional analysis was performed with annotation from the Gene Ontology (GO), by which we identified 50 significantly associated GO annotation terms (Bonferroni-corrected p<0.01, among terms in the Biological Process and Cellular Component GO domains), that represented 187 of the 429 differentially regulated genes (FIG. 2 and FIGS. 3A-3B). By network analysis, these annotation terms, together with their associated genes, were further grouped into three functionally related modules, each of which was characterized by its most significant annotation terms (FIG. 1D). The three modules represented genes and functions related to (1) glial cell differentiation and myelination, (2) axon guidance and axonogenesis, and regulation of synapse structure and synaptic signaling (FIG. 1D). The first and second modules were closely interconnected and contained an array of critical oligodendrocyte lineage transcription factors, including SOX10, SIRT2, MYRF, NKX2.2, TCF7L2, OLIG1, and OLIG2, as well as stage-regulated and myelin-associated proteins, which included TF, MBP, MAG, OMG, UGT8, and FA2H; all of these were significantly downregulated in HD hGPCs. The third module contained genes concerned with the regulation of components of synaptic transmission, most notably SYNDIG1, BCAN, NETO1, and SNPH, as well as genes encoding the glutamate receptor signaling proteins GRIA2, GRIA4, GRID1, GRID2, and GRIK4 and the potassium channels encoded by KCND2, KCNJ9, KCNQ1, and KCNS3; all of these were significantly downregulated (FIGS. 1E-1G). Together, these HD-dysregulated genes and their associated functions suggest an HD-dependent suppression in the differentiation of hGPCs into mature oligodendroglia.

Figure 4A:
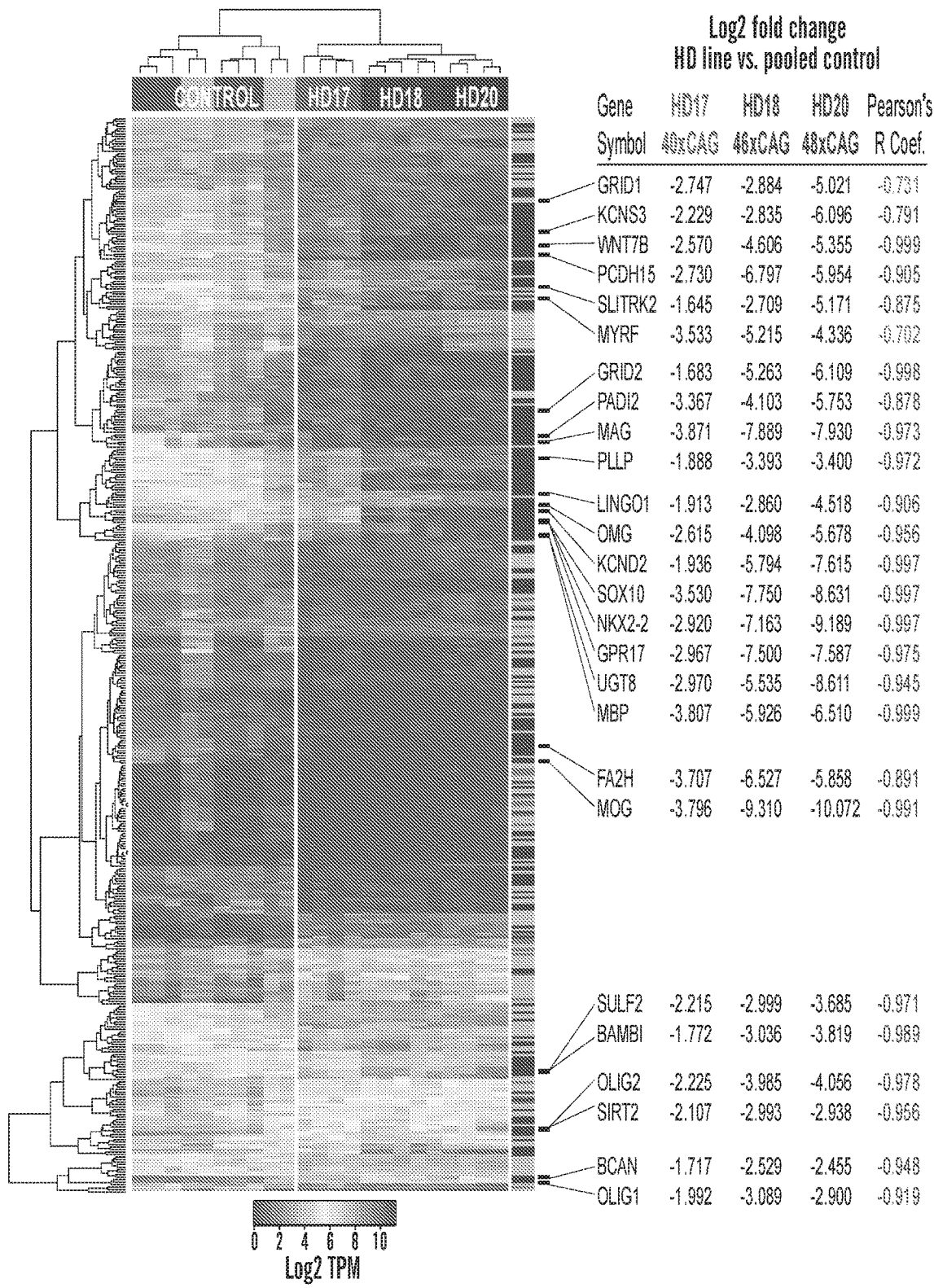
FIGS. 4A-4C show increasing CAG lengths correlate with diminished oligodendroglial gene expression.
Figure 4B:
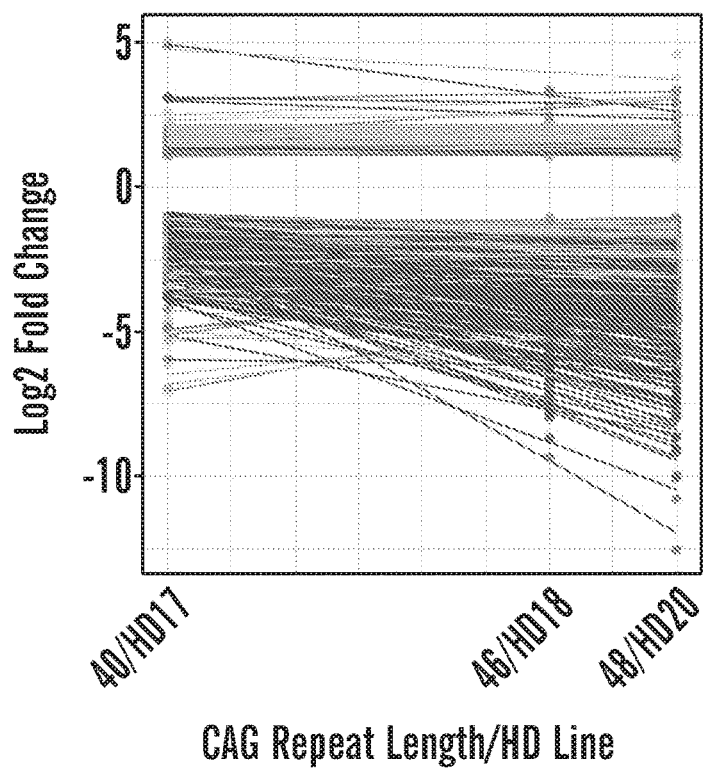
Figure 4C:
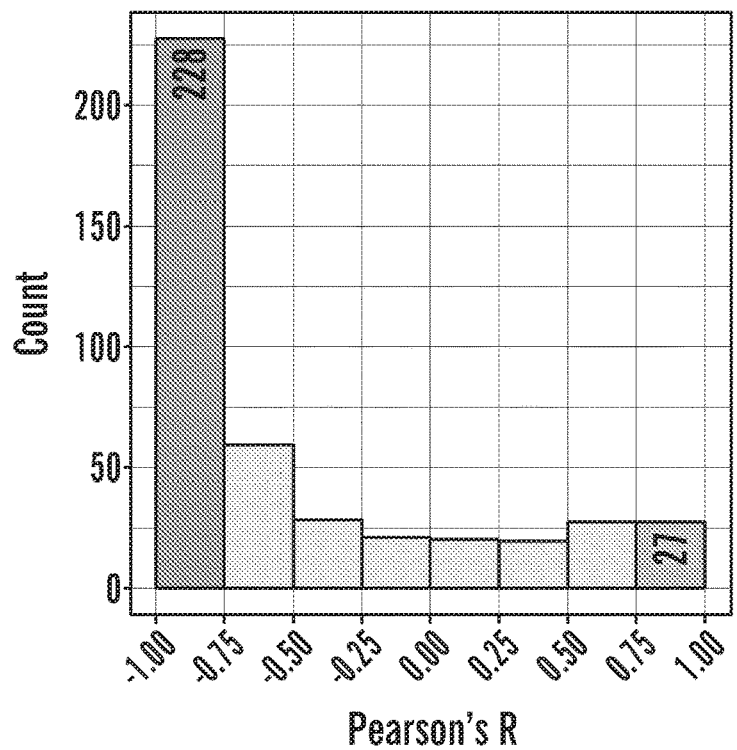
Figure 5A:
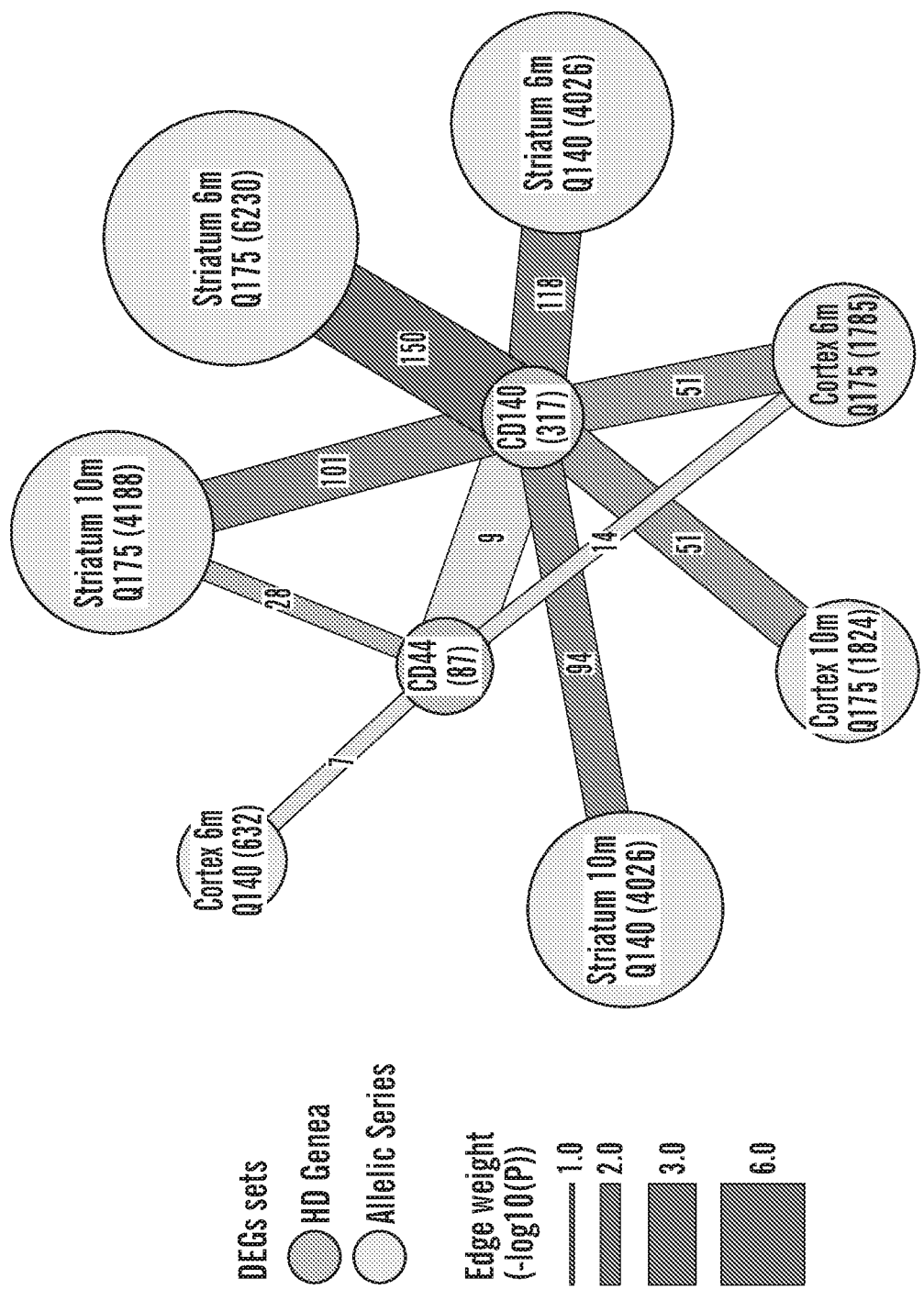
FIGS. 5A-5D show human and mouse glia exhibited overlap in genes dysregulated as a function of CAG repeat length. There was a high degree of overlap between those hGPC genes and ontologies found to be increasingly dysregulated with longer CAG repeat length in hGPCs, with those noted to be dysregulated with CAG repeat length in mouse brain tissue (Langfelder et al., "Integrated Genomics and Proteomics Define Huntingtin CAG Length-Dependent Networks in Mice," *Nat. Neurosci.* 19:623-633 (2016), which is hereby incorporated by reference in its entirety).
Figure 5B:
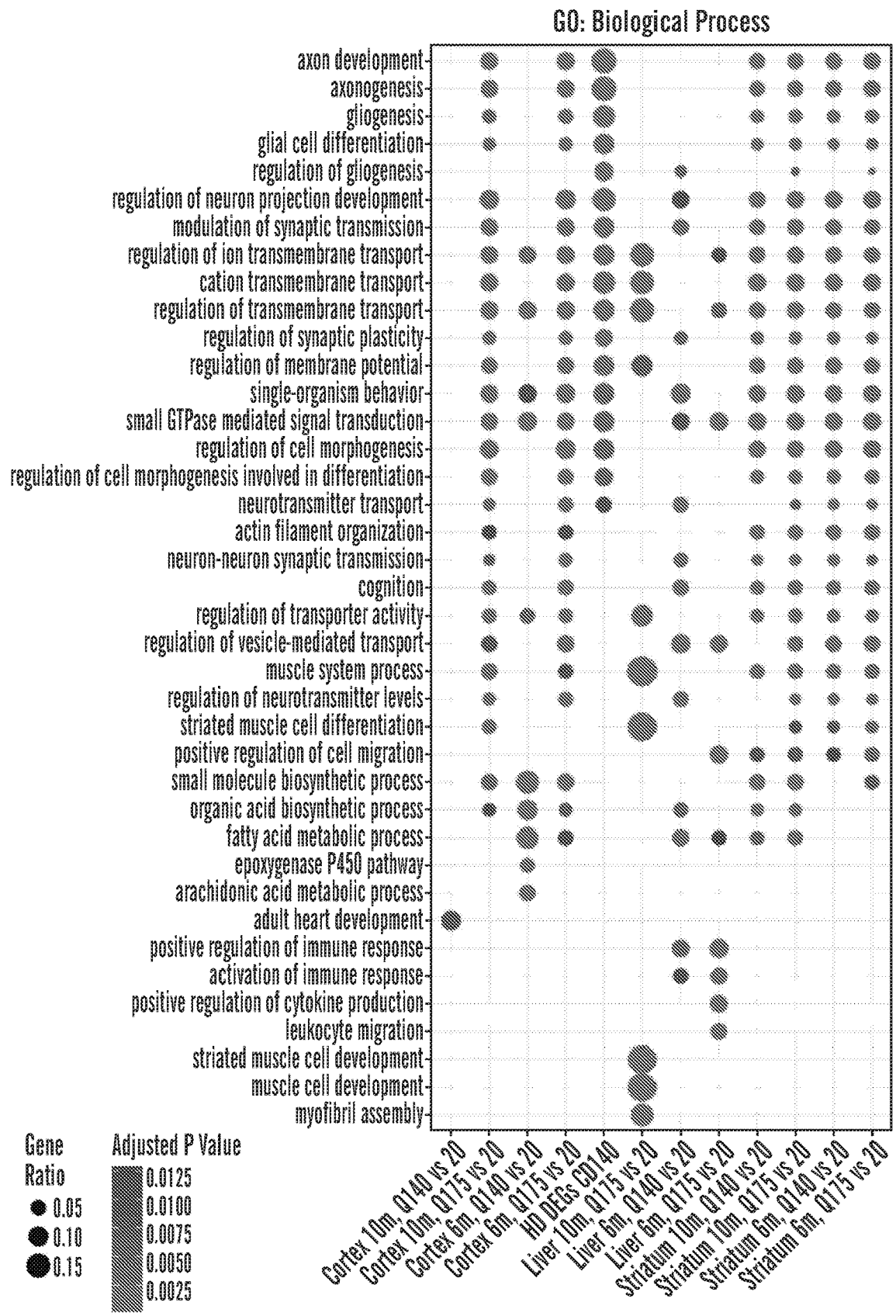
Figure 5C:
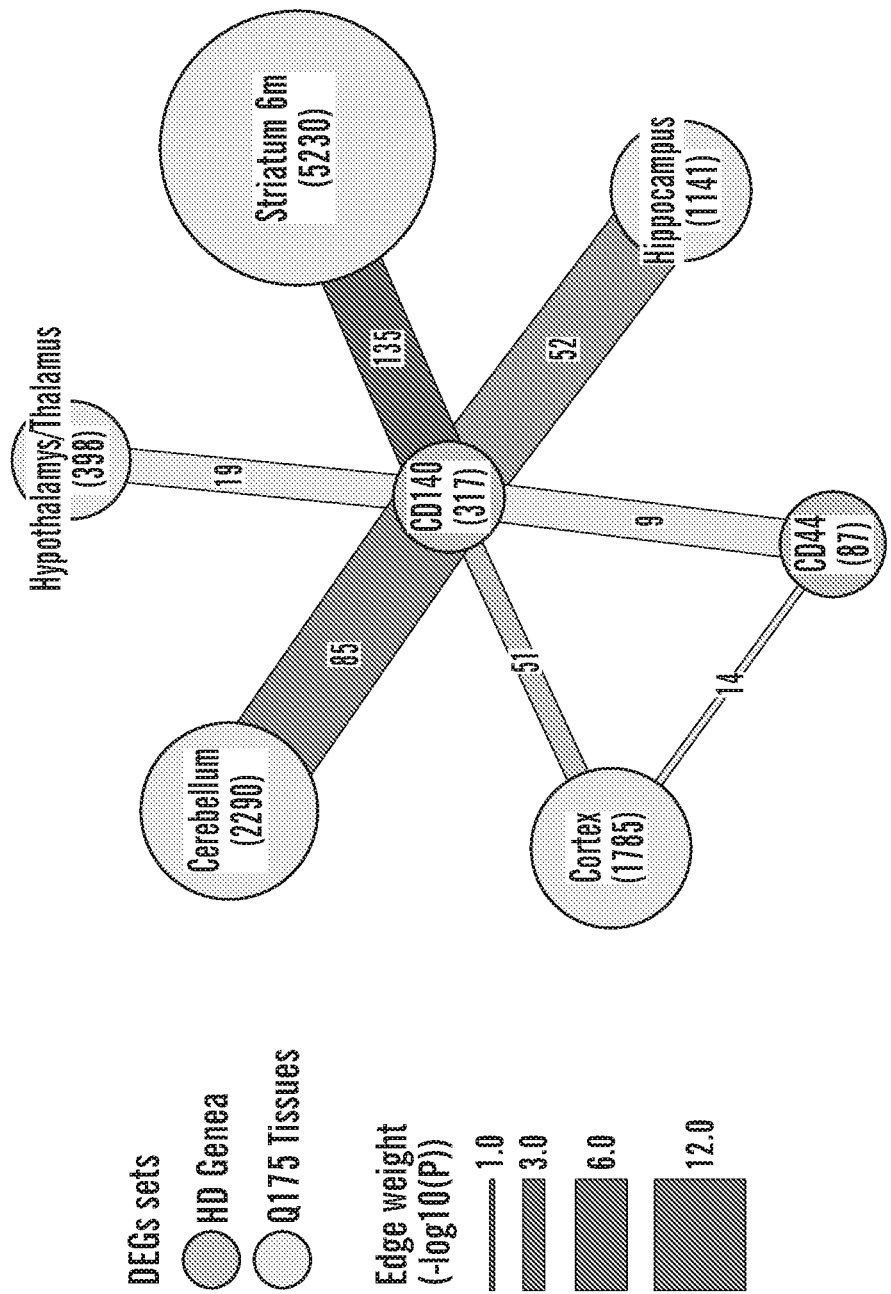
Figure 5D:
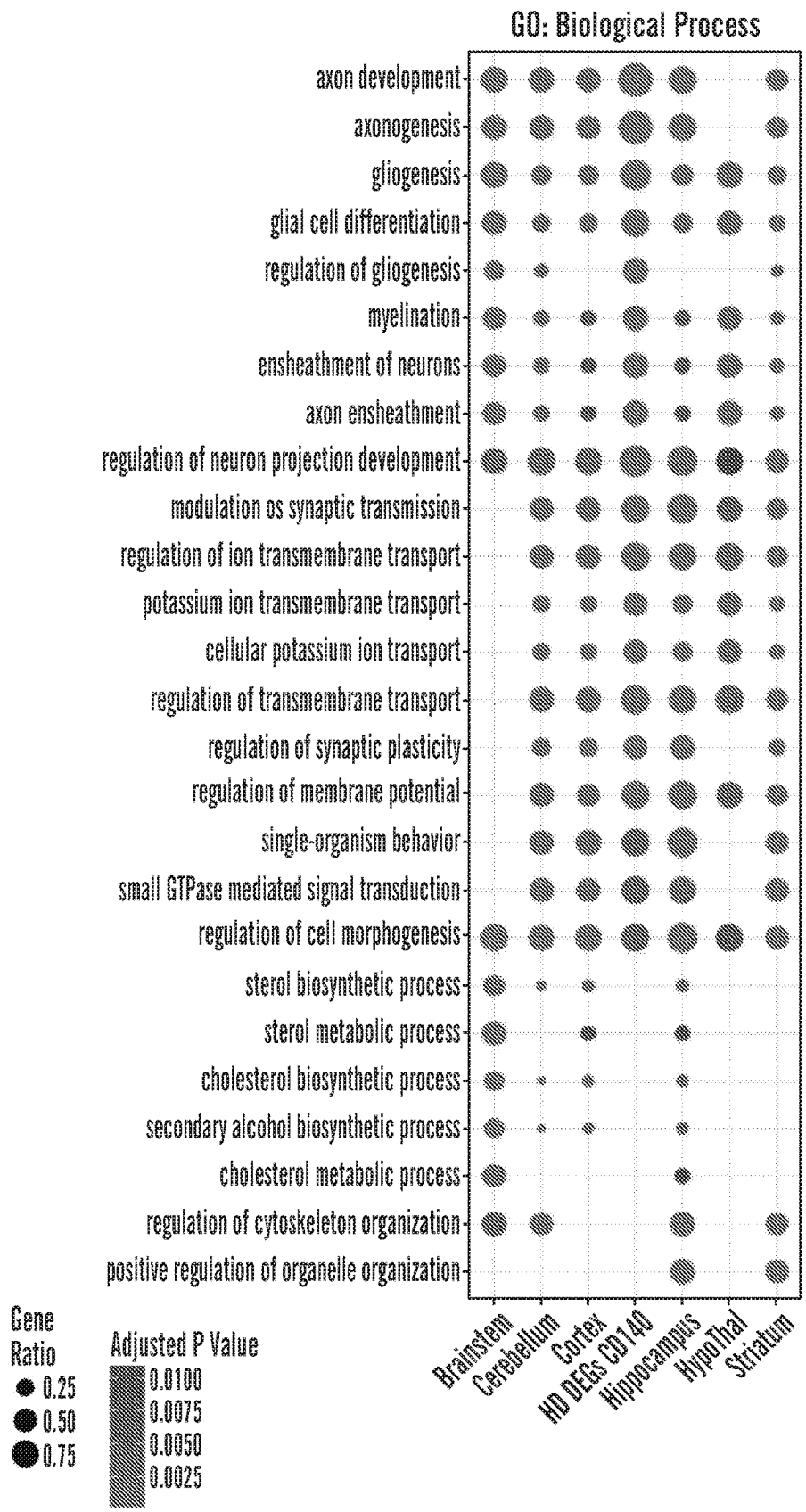

Example 2—mHTT hGPCs Down-Regulate Transcriptional Determinants of Myelinogenesis As revealed by the differential expression analysis, a key set of transcription factors associated with both oligodendroglial differentiation and myelin biosynthesis were significantly and substantially downregulated as a function of mHTT expression. These included the early oligodendroglial regulators NKX2.2, OLIG2, and SOX10, each of which was sharply downregulated in mHTT-expressing hGPCs (FIG. 1E). Moreover, downstream of the mHTT-suppressed oligodendroglial lineage transcription factors, the mHTT hGPCs expressed sharply reduced levels of MYRF, the myelin-regulatory factor. MYRF coordinately activates a number of genes necessary for myelin formation (Bujalka et al., "MYRF is a Membrane-Associated Transcription Factor that Autoproteolytically Cleaves to Directly Activate Myelin Genes," *PLoS Biology* 11:e1001625 (2013), which is hereby incorporated by reference in its entirety), and its production has been noted to be deficient in mouse mHTT-transgenic oligodendrocytes (Huang et al., "Mutant Huntingtin Downregulates Myelin Regulatory Factor-Mediated Myelin Gene Expression and Affects Mature Oligodendrocytes," *Neuron* 85:1212-1226 (2015), which is hereby incorporated by reference in its entirety). Among the human-ESC-derived hGPCs, the MYRF-regulated myelinogenic transcripts MBP, MAG, OMG, PLP1, and MOG were all significantly downregulated (FIG. 1E). Moreover, when directly compared the expression pattern of hGPCs derived from the sibling pair (GENEA20 for mHTT and GENEA19 for normal HTT), which have minimal background genetic variation between them, the differential downregulation in mHTT hGPCs of those genes associated with myelinogenesis was again noted. These included MYRF (−4.04-fold lower in mHTT hGPCs; log 2 scale), MAG (−6.78), MBP (5.14), MOG (−10.35), OMG (−5.15), and PLP1 (−2.22), indicating a broad downregulation of myelinogenesis-associated transcripts in HD hGPCs. Importantly, when the RNA expression patterns of hGPCs derived from three different mHTT hESC lines, GENEA17, GENEA18, and GENEA20, whose HTT genes have 40, 46, and 48 CAG repeats, respectively, were compared, it was noted that longer CAG repeat lengths correlated strongly with the progressive downregulation of these same differentiation- and myelinogenesis-associated genes (FIGS. 4A-4C). Importantly, there was a high degree of overlap between those genes and ontologies found to be increasingly dysregulated with longer CAG repeat length in hGPCs, with those genes and ontologies increasingly dysregulated with CAG repeat length in HD transgenic mice (Langfelder et al., "Integrated Genomics and Proteomics Define Huntingtin CAG Length-Dependent Networks in Mice," *Nat. Neurosci.* 19:623-633 (2016), which is hereby incorporated by reference in its entirety) (FIGS. 5A-5D).

Figure 6A:
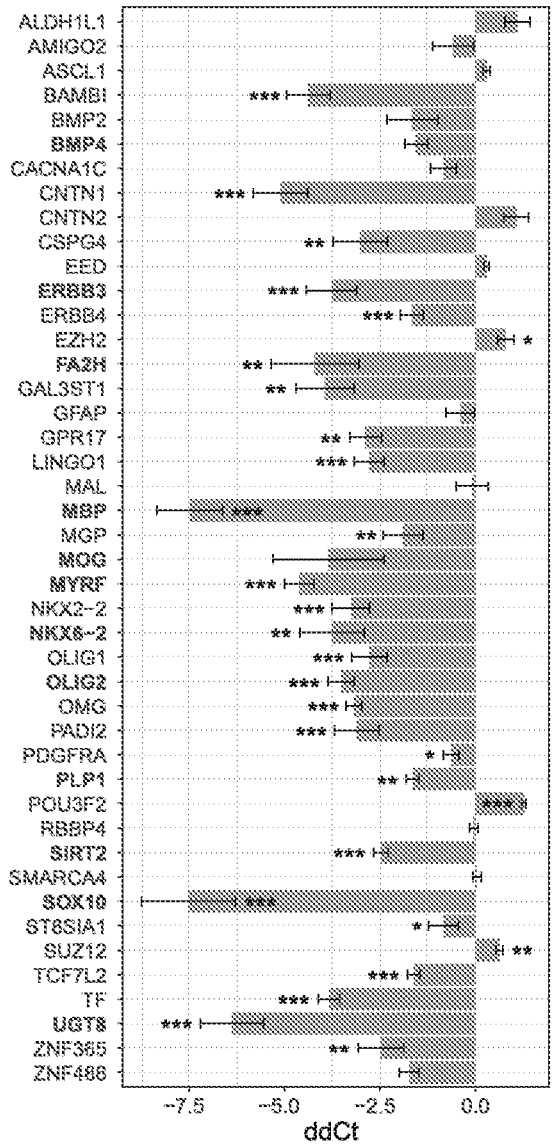
FIGS. 6A-6B show glial differentiation-associated genes are dysregulated in mHTT-expressing GPCs. Expression of selected genes dysregulated in HD-derived GPCs, as identified by RNA-seq analysis, was assessed by TaqMan Low Density Array (TLDA) RT-qPCR and compared to that of control GPCs. Expression data were normalized to 18S and GAPDH endogenous controls. Mean ddCt values and standard error ranges calculated from 3 pooled HD GPC lines (n=3 for lines GENEA17 and GENEA20, n=5 for GENEA18, total n=11) vs. 2 pooled control GPC lines (n=6 for GENEA02 and n=3 for GENEA19, total n=9) are shown. The difference of expression in HD and control GPCs was assessed by paired t-tests, followed by Benjamini-Hochberg (BH) multiple testing correction (*p<0.01, p<0.05, *p<0.1). Genes assayed on both arrays are highlighted in bold. Analysis of TLDA data was performed in Expression-Suite software v.1.1 (Applied Biosciences). The majority of genes identified by RNA-seq as dysregulated in HD-derived GPCs were confirmed as such by TLDA.
Figure 6B:
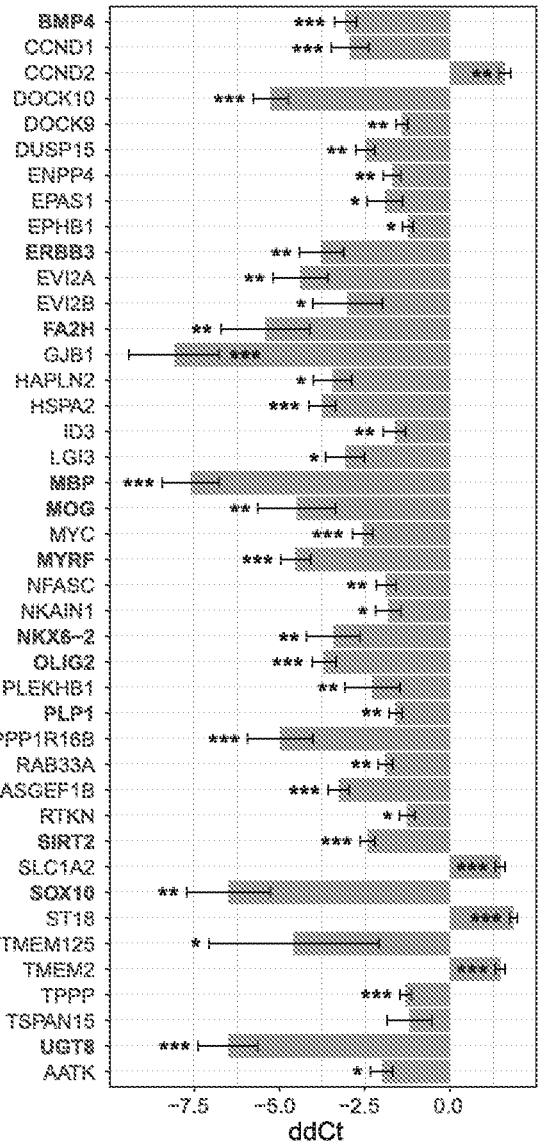

To validate these RNA-seq-based expression data, qRT-PCR with TaqMan low-density arrays (TLDAs) was then used to compare the expression levels of these differentiation-associated genes between mHTT and control hGPCs. The majority of those genes identified in RNA-seq analysis as differentially dysregulated in the mHTT hGPCs were confirmed as such (FIGS. 6A-6B). These genes included the key oligodendroglial lineage transcription factors MYRF, SOX10, and OLIG2, as well as their downstream myelinogenesis-associated targets, including PLP1, MOG, and MBP. Based on the downregulation of this broad set of myelination-associated genes, a significant disruption in both myelin biogenesis and maintenance by mHTT hGPCs was predicted.

Figure 7:
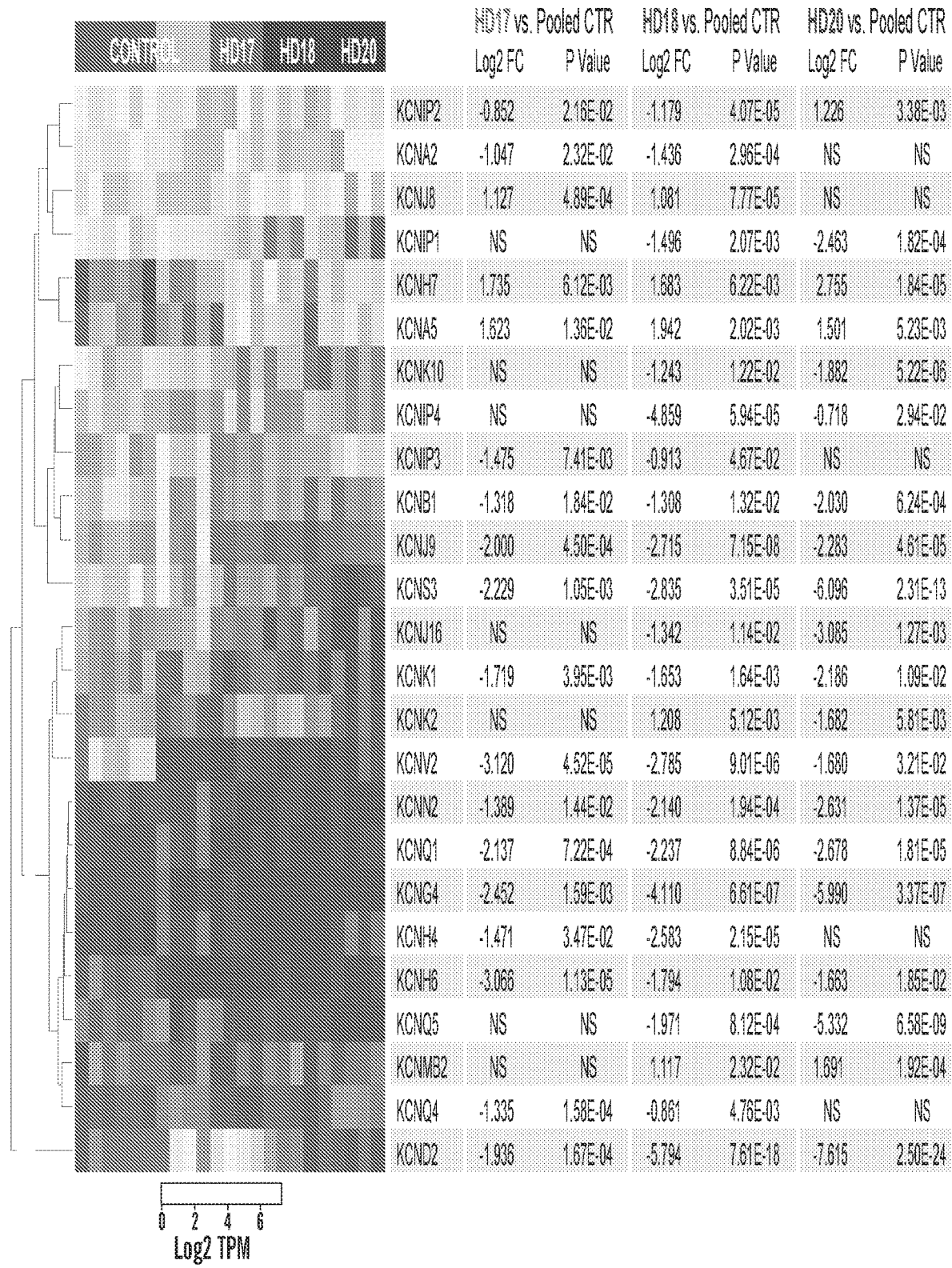
FIG. 7 shows HD-derived hGPCs showed marked dysregulation of potassium channel genes. Differential gene expression comparisons (FDR 5%, no fold change threshold) of each HD-derived hGPC line against pooled control hGPCs revealed 25 potassium channel genes that were dysregulated in at least 2 out of 3 HD-derived lines. NS=not significant.

Example 3—mHTT-Associated Differentiation Arrest Suppressed Potassium Channel Expression Among the functionally related genes most differentially dysregulated by mHtt expression were those encoding ion channels and transporters, in particular the potassium channels. This large group of genes includes 117 known members in the human genome (Pruitt et al., "NCBI Reference Sequences (RefSeq): A Curated Non-Redundant Sequence Database of Genomes, Transcripts and Proteins," *Nucleic Acids Research* 35:D61-D65 (2006), which is hereby incorporated by reference in its entirety), of which 93 were detectably expressed by hGPCs (raw counts>5 in at least 3 samples across the dataset). Among these, 25 of the 93 identified $K^+$ channel and transporter genes were dysregulated in the HD hGPCs relative to their pooled hESC GPC controls using a FC>2.0 cutoff and 5% FDR threshold; 23 of these remained significantly dysregulated even at a 1% FDR (FIG. 7). These genes included a number of inwardly rectifying $K^+$ channels, the coordinate suppression of which suggested a basis for the disrupted potassium buffering of the HD brain (Tong et al., "Astrocyte Kir4.1 Ion Channel Deficits Contribute to Neuronal Dysfunction in Huntington's Disease Model Mice," *Nat Neurosci* 17:694-703 (2014), which is hereby incorporated by reference in its entirety). To further refine and prioritize within this large set of coordinately dysregulated $K^+$ channel genes, the GENEA20 versus GENEA19 sibling pair comparison was included as an additional filtration. By this most stringent analysis, 4 genes (KCND2, KCNJ9, KCNQ1, and KCNS3) remained strongly and significantly downregulated both in all HD hGPC lines relative to pooled controls and within the sibling set of mHTT and normal hESC-derived hGPCs. Together, the dysregulated expression of these $K^+$ channel genes are of special significance given their role in maintaining stable interstitial $K^+$ levels and determining action potential thresholds. As such, the mHTT-associated suppression of the hGPC $K^+$ channels, which among other roles mediate the glial reuptake of synaptic $K^+$, may causally contribute to the neuronal hyper-excitability observed among striatal neurons in HD (Benraiss et al., "Human Glia can Both Induce and Rescue Aspects of Phenotype in Huntington Disease. *Nature Communications* 7:11758 (2016); Shin et al., "Expression of Mutant Huntingtin in Glial Cells Contributes to Neuronal Excitotoxicity," *J Cell Biol* 171:1001-1012 (2005); Tong et al., "Astrocyte Kir4.1 Ion Channel Deficits Contribute to Neuronal Dysfunction in Huntington's Disease Model Mice," *Nat Neurosci* 17:694-703 (2014), which are hereby incorporated by reference in their entirety).

In light of the concurrent dysregulation of glial differentiation as well as K$^+$ channel expression and the dependence of the latter upon the former, it was asked whether a common upstream regulator might exist that is dysregulated itself as a function of mHTT expression. Using Ingenuity Pathway Analysis (IPA), it was found that TCF7L2 was predicted as a positive regulator of a broad variety of glial differentiation-associated genes, including several that have been reported to regulate K$^+$ channel gene expression, such as the SOX10-modulated KCNB1 (Liu et al., "Chromatin Landscape Defined by Repressive Histone Methylation During Oligodendrocyte Differentiation," *J Neurosci* 35:352-365 (2015), which is hereby incorporated by reference in its entirety), which was downregulated in hGPCs derived from all three of the tested HD lines. Among these glial-differentiation-associated genes were a number whose expression was markedly deficient in mHTT glia relative to their controls (FIG. 6A). On that basis, RNA-seq datasets were queried for both TCF7L2 and TCF7L2-regulated transcripts and found that TCF7L2 was indeed differentially downregulated in HD relative to normal hGPCs, while TCF7L2-regulated genes were concomitantly downregulated (FIG. 6B). Since TCF7L2 has been strongly implicated in glial differentiation (and oligodendroglial differentiation in particular), these results further emphasized the cell-intrinsic nature of the glial differentiation block in HD.

Example 4—HD hGPCs Exhibited Impaired Myelinogenesis In Vivo

Since mHTT hGPCs appeared deficient in their acquisition of gene expression patterns typifying oligodendrocyte maturation and myelinogenesis, it was asked if hypomyelinated mice engrafted with HD GPCs were deficient in myelination competence relative to those engrafted with GPCs from a normal sibling. To this end, mHTT-expressing and control hGPCs, respectively derived from the sibling female GENEA20 and GENEA19 lines in matched cultures, were transplanted neonatally into immunodeficient shiverer mice using the described multisite injection protocol with bilateral hemispheric injections. This protocol yields a stereotypic pattern and time course of donor-derived myelination in host brains when using normal pluripotent stem cell-derived or tissue-derived hGPCs (Wang et al., "Human iPSC-Derived Oligodendrocyte Progenitor Cells can Myelinate and Rescue a Mouse Model of Congenital Hypomyelination," *Cell Stem Cell* 12:252-264 (2013b); Windrem et al., "Neonatal Chimerization with Human Glial Progenitor Cells can Both Remyelinate and Rescue the Otherwise Lethally Hypomyelinated Shiverer Mouse," *Cell Stem Cell* 2:553-565 (2008), which are hereby incorporated by reference in their entirety). In this case, while nonisogenic (no truly isogenic lines for normal and mutant Huntingtin have yet been reported), the use of sibling lines for this experiment minimized genetic variation to the extent possible. Using these paired lines and this in vivo model, the oligodendrocytic differentiation and myelination patterns of engrafted mice were assessed at 8, 13, and 18 weeks of age (n=3-5 mice per time point, totaling 12 HD hGPC-engrafted and 10 control hGPC-engrafted mice). The brains of these mice were cryo-sectioned, immunolabeled for both oligodendroglial and myelin antigens, and confocal imaged to compare the differentiation and myelination efficiency of HD and control-derived hESC hGPCs in vivo.

Figures 8A, 8B, 8C, 8D, 8E, 8F:
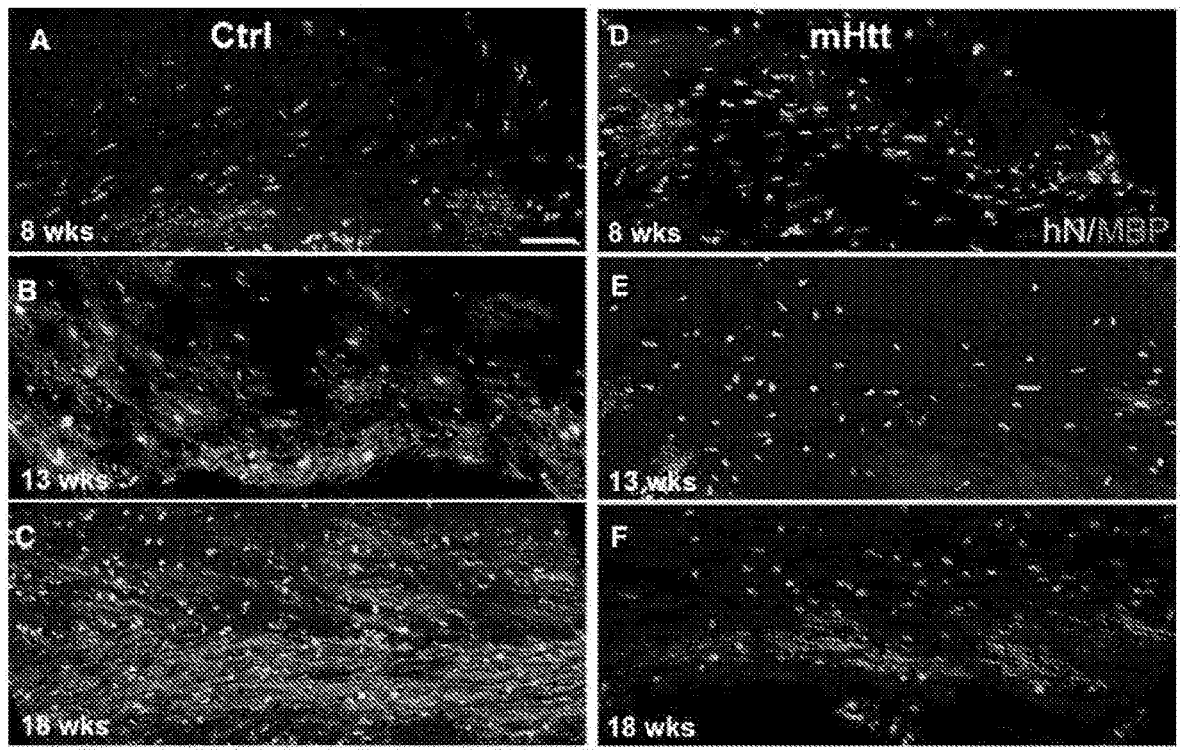
Figure 8G:
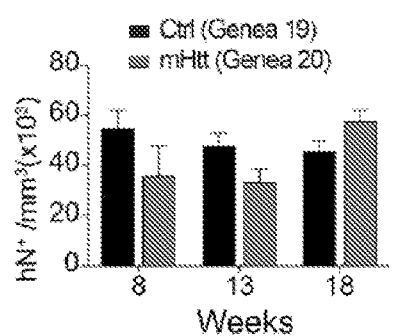
FIGS. 8G-8I show the density of engrafted human GPCs did not differ between control and mHTT hGPCs at any time point assessed (FIG. 8G), but the fraction of those hGPCs that differentiated as transferrin (TF)+ oligodendrocytes was significantly lower among mHTT-expressing hGPCs (FIG. 8H), resulting in fewer TF-defined oligodendrocytes in chimeras engrafted with mHTT hGPCs (FIG. 8I).
Figure 8H:
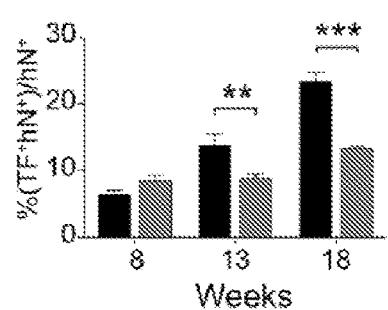
Figure 8I:
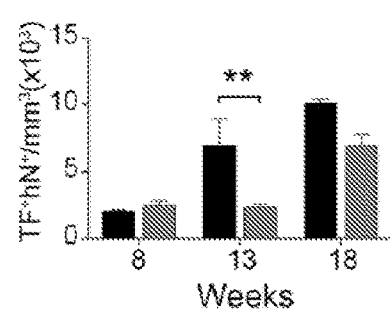
Figure 8J:
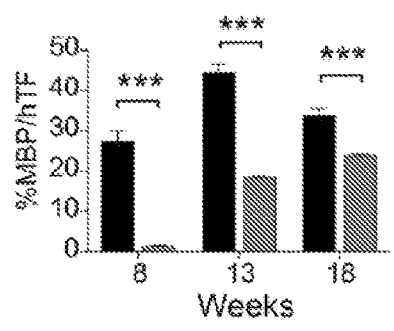
FIGS. 8J-8L show that among donor-derived oligodendrocytes, the proportion that became myelinogenic, as defined by MBP co-expression of human TF and MBP, was significantly lower in mHTT—than control hGPC-engrafted chimeric brains (FIG. 8J). Similarly, the fraction of all donor cells that developed MBP expression was significantly higher in mice engrafted with control compared to HD-derived hGPCs (FIG. 8K). Accordingly, myelin luminance, as assessed on MBP-immunostained sections, was significantly higher in control-engrafted corpus callosa than in corresponding mHTT GPC-engrafted white matter (FIG. 8L).
Figure 8K:
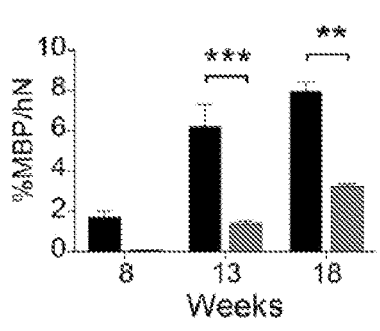
Figure 8L:
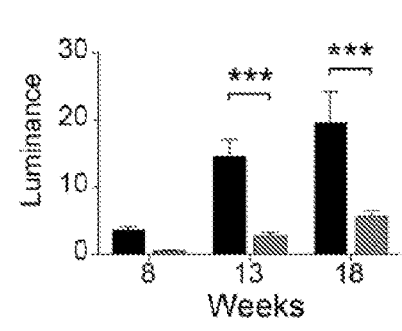

It was found that the appearance of both oligodendroglial phenotypic markers and indices of myelin protein production occurred significantly earlier in control hGPC-engrafted mice relative to HD hGPC-engrafted animals. Whereas the expression of axonally engaged myelin basic protein was apparent using control hGPCs by 8 weeks after neonatal graft, mice engrafted with HD hGPCs manifested no evident MBP immunolabeling by that time point (FIGS. 8A and 8D). By 12-13 weeks of age (a point by which mice engrafted with control hGPCs exhibited robust myelin production), only scattered islands of MBP expressed by immature oligodendroglia were noted in matched recipients of HD GPCs (FIGS. 8B and 8E). The relatively delayed myelination of HD GPC-engrafted white matter persisted for at least 4 months; by 18 weeks, whereas control GPC-engrafted mice exhibited dense callosal and capsular myelination, confluent regions of MBP-defined myelination were only just arising in the mHTT-engrafted brains (FIGS. 8C and 8F). Accordingly, the fractions of human donor cells that differentiated as transferrin$^+$ oligodendrocytes (FIGS. 8H and 8I) and their derivatives, MBP$^+$ myelinating oligodendrocytes (FIGS. 8J and 8K), were significantly higher in mice engrafted with GENEA19 control GPCs than in mice engrafted with GENEA20 mHTT GPCs. Similarly, myelin luminance, as assessed on MBP-immunostained sections, was significantly higher at both time points in control GPC-engrafted corpus callosa than in their mHTT GPC-engrafted counterparts (FIG. 8L). Nonetheless, neither the density nor distribution of engraftment by human GPCs differed significantly between control and HD-derived cells (FIGS. 8G, 8M, 8N), indicating that the myelination defect in HD hGPC-engrafted brains was due to an mHTT-associated impediment in donor cell oligodendrocytic differentiation and myelin production rather than in differential engraftment.

Figures 9A, 9B, 9C, 9D, 9E, 9F, 9G, 9H:
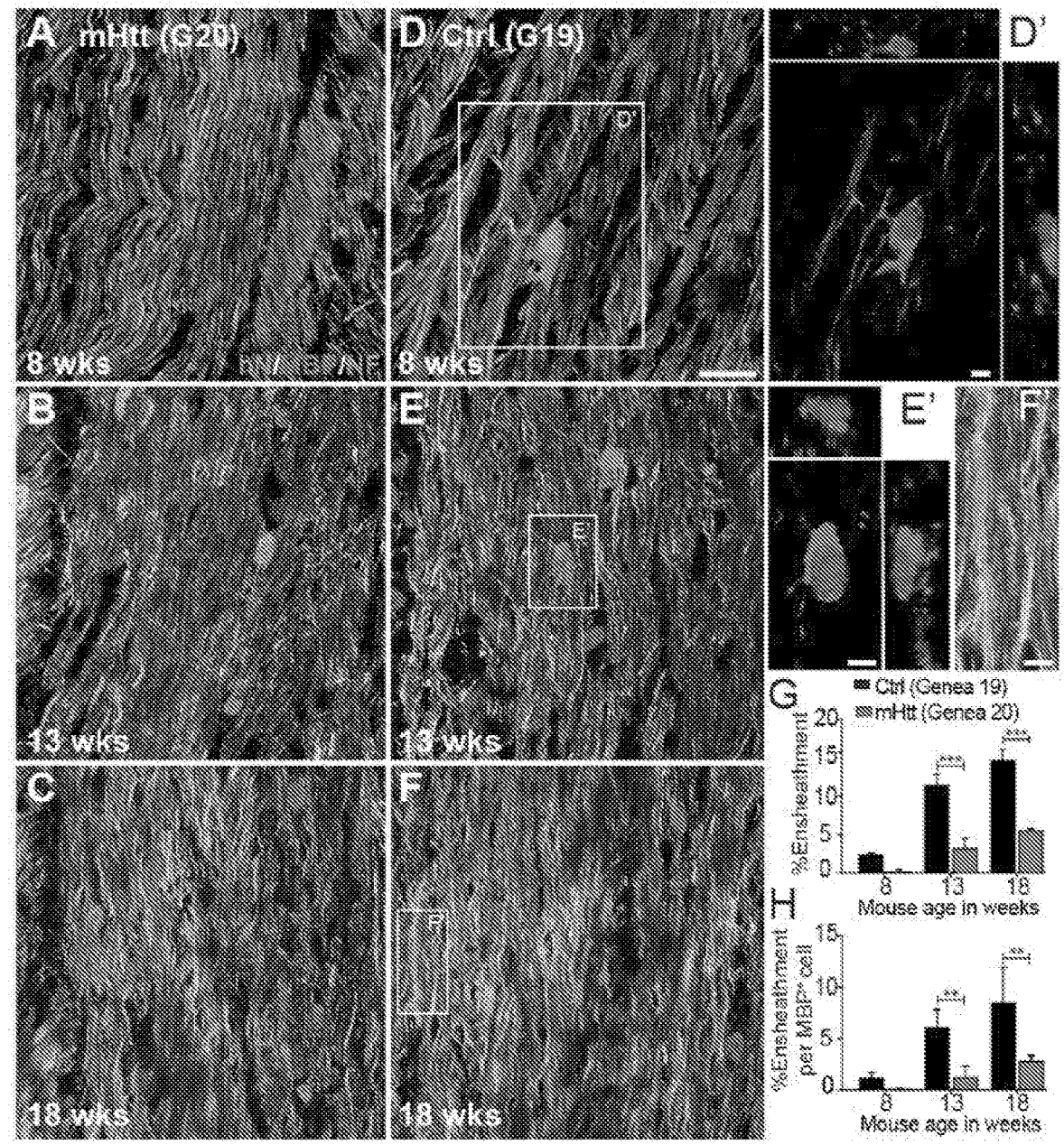
FIGS. 9A-9H show mHTT GPC-engrafted brains exhibited diminished and delayed axonal myelination.

The mHTT-associated delay in myelination had significant consequences in the rate and efficiency of axonal myelination. When callosal myelination was analyzed by high-resolution confocal imaging of individual callosal axons, it was evident that axonal ensheathment was impaired in mHTT hGPC- engrafted brains (FIGS. 9A-9F). At both the 13- and 18-week time points, the mHTT hGPC chimeric brains exhibited fewer myelinated axons (FIG. 9G); a greater proportion of those axons that myelinated did so incompletely along the length of visualized axons, while fewer axons were ensheathed per MBP$^+$ human oligodendrocyte identified (FIG. 9H). Together, these data indicate that shiverer mice rendered chimeric for mHTT-expressing hGPCs failed to myelinate as quickly or as well as those engrafted with normal hESC hGPCs, yielding relatively hypomyelinated animals with deficient axonal ensheathment. Thus, the mHTT-associated differentiation block suggested by the expression profiles of mHTT hGPCs appears to be reflected by their relative deficiency in oligodendrocytic differentiation competence, leading to hypomyelination in vivo.

Figure 10:
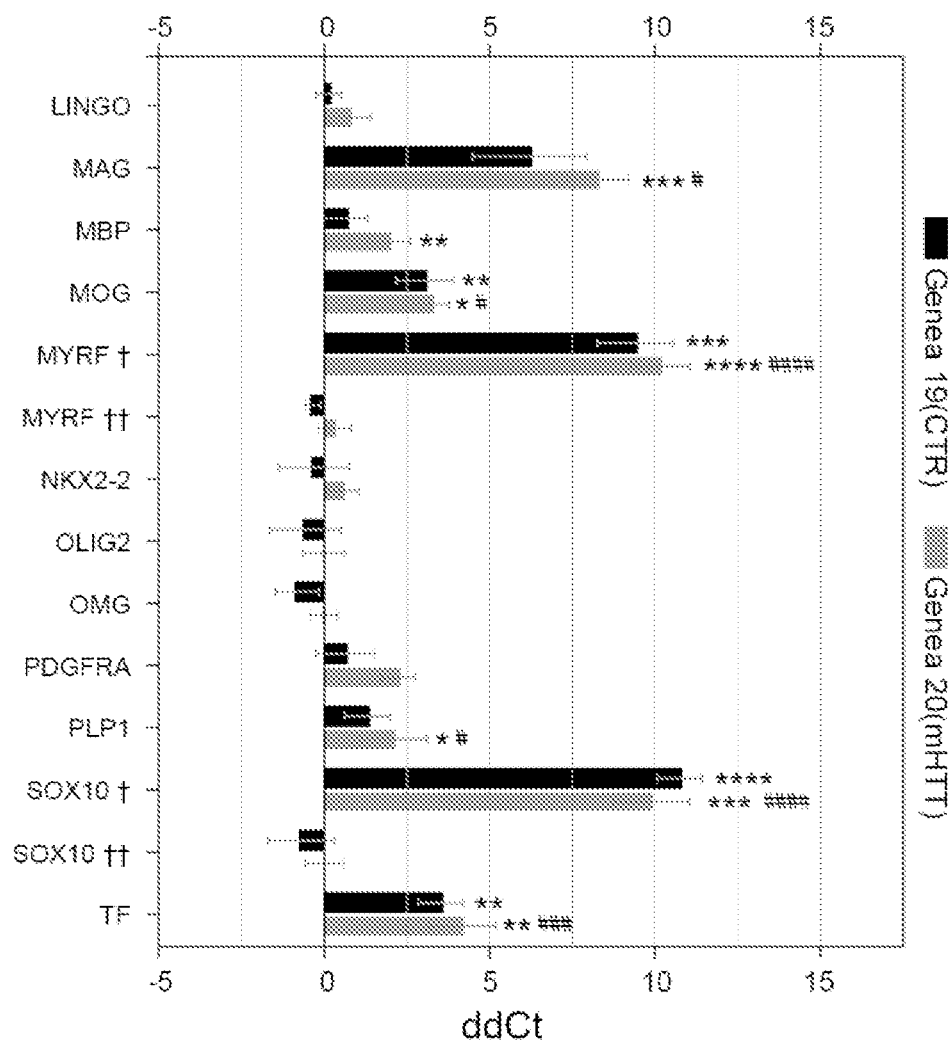
FIG. 10 shows SOX10-MYRF transduction restores myelin gene expression in mHTT GPCs. This figure shows a graphical representation of the qPCR data outlined in Table 1 below.

Example 5—Myelin Gene Expression and Myelinogenesis In Vivo Could Be Rescued by SOX10 and MYRF In light of the primacy of SOX10 and MYRF in regulating myelin synthesis (Bujalka et al., "MYRF is a Membrane-Associated Transcription Factor that Autoproteolytically Cleaves to Directly Activate Myelin Genes," *PLoS Biology* 11:e1001625 (2013); Emery et al., "Myelin Gene Regulatory Factor is a Critical Transcriptional Regulator Required for CNS Myelination," *Cell* 138:172-185 (2009); Lopez- Anido et al., "Differential Sox10 Genomic Occupancy in Myelinating Glia," *Glia* 63:1897-1914 (2015), which are hereby incorporated by reference in their entirety) and their role as terminal effectors of myelin gene expression, the data suggested that the transcriptional activation of SOX10 and MYRF might be sufficient to rescue the myelination defect of HD. On that basis, it was next asked whether the forced expression of SOX10 and MYRF in mHTT-expressing hGPCs rescued the expression of MAG, MBP, and other critical genes involved in myelin biosynthesis. To this end, expression of SOX10 and MYRF was induced in both mHTT and normal control hESC-derived hGPCs (GENEA20 and GENEA19, respectively) via plasmid transfection using a bicistronic plasmid in which both genes were placed under the control of the constitutive EF1a promoter. Their expression was then compared with that of downstream myelinogenic genes, including MAG, MBP, MOG, PDGFRA, PLP1, TF, and LINGO1, in SOX10-MYRF and control plasmid-transfected cells using qPCR. It was found that overexpression of SOX10-MYRF indeed rescued the expression of most myelin-associated genes in the transfected mHTT hGPCs (Table 1; FIG. 10).

On the basis of these data, it was next asked whether SOX10 and MYRF overexpression was sufficient to rescue downstream oligodendrocyte differentiation and myelinogenesis. To this end, a doxycycline-regulated dual vector lentiviral transduction strategy was developed, which allowed the doxycycline (DOX)-triggered, interdependent overexpression of SOX10 and MYRF with concurrent expression of CD4 to permit FACS-based immunoisolation of SOX10-MYRF-transduced hGPCs (FIG. 11A). The effects of SOX10 and MYRF overexpression in mHTT-expressing hGPCs was first assessed by transducing matched sets of 180 days in vitro (DIV) GENEA20-derived hGPCs with DOX-regulated lentiviral SOX10/MYRF and then exposing some cultures to DOX while leaving matched control cultures untreated. It was confirmed that in cells raised in the absence of DOX, SOX10 and MYRF expression was no different than that of untransduced GENEA20-derived hGPCs. After an additional week in vitro, cells were then immunostained for the oligodendrocytic sulfatide recognized by 04, which is expressed by lineage-restricted, largely post-mitotic human oligodendrocytes. Without DOX, the mHTT hGPCs were maintained as such and expressed no detectable 04. In contrast, those mHTT hGPCs raised in DOX, with upregulated SOX10 and MYRF expression, exhibited a sharp and significant increment in oligodendrocyte differentiation, with >15% expressing 04 immunoreactivity (FIGS. 11B-11D).

Since the induction of SOX10 and MYRF expression appeared sufficient to rescue oligodendrocyte differentiation from mHTT hGPCs in vitro, it was next asked if SOX10 and MYRF expression was similarly sufficient to rescue myelinogenesis in vivo. To this end, GENEA20-derived HD hGPCs were transduced with DOX-regulated lentiviral SOX10/MYRF as above using the vector system by which concurrent SOX10 and MYRF expression was reported by CD4 expression, sorted the cells on CD4, and transplanted the SOX10/MYRF-transduced mHTT hGPCs into neonatal shiverer mice. At 9 weeks of age, some of the transplanted mice were given DOX (orally, introduced into their water ad lib) so as to trigger SOX10 and MYRF expression, while others were not given DOX, thereby serving as matched controls (FIG. 11E). At 13 weeks of age (a time point by which normal hGPCs typically initiate myelination, while untreated mHTT hGPCs have not yet done so; FIGS. 11F and 11G), the mice were sacrificed and their brains sectioned and immunostained for MBP. It was found that DOX(+) mice in which donor-derived hGPCs SOX10 and MYRF were induced exhibited significant numbers of MBP+ myelinating oligodendrocytes in the host's engrafted white matter. Quantitatively, DOX(+) mice engrafted with SOX10/MYRF-transduced, DOX-regulated GENEA20 GPCs exhibited robust myelinogenesis: 28.6%±0.8% (n=3 mice; mean±SEM) of donor cells expressed MBP by 13 weeks, while no donor cells in identically engrafted DOX(-) mice (n=6 mice) developed detectable MBP expression ($p<0.0001$). By way of comparison, 18.1%±2.1% (n=5) of normal GENEA19-derived GPCs developed MBP expression by that same time point, indicating that the SOX10/MYRF-transduced HD hGPCs were at least as efficient as normal hGPCs in MBP-defined myelinogenesis in vivo.

In DOX(+) mice engrafted with SOX10/MYRF-transduced GENEA20 hGPCs, the resultant oligodendrocytes proved sufficient to induce the formation of nodes of Ranvier by resident shiverer axons, which exhibited the typical clustering of βIV—spectrin flanked by CASPR1 that characterizes nodal architecture (FIGS. 11L and 11M). In contrast, by that same time point, no donor cells in DOX(-) control mice had developed MBP expression (FIGS. 11H-11J), nor were clearly defined nodes observed, despite analogous donor cell engraftment (FIG. 11K). These data indicated that the forced expression of SOX10 and MYRF was sufficient to rescue both oligodendrocyte differentiation and myelination by mHTT-expressing hGPCs.

Example 7—mHTT Impairs Human Astroglial Differentiation In Vivo

Since hGPCs give rise to astrocytes as well as oligodendrocytes, the mHTT-associated defect in oligodendroglial lineage progression, along with the RNA expression data indicating a transcriptional impediment to glial differentiation upstream of the astrocyte-oligodendrocyte fate choice, suggested an analogous impediment to astrocytic differentiation. On that basis, it was next asked if mice neonatally injected with mHTT-expressing hGPCs (GENEA20 derived) exhibited any differences in astrocytic differentiation in vivo relative to mice injected with normal HTT sibling control hGPCs (GENEA19). To that end, the same mice examined earlier for the effect of HD genotype on myelinogenesis were used to assess its effect on the maturation of glial fibrillary acidic protein (GFAP)-defined white matter astrocytes. The control and HD hGPC-engrafted shiverer brains were immunostained at 8, 13, and 18 weeks after neonatal graft using a species-specific anti-human GFAP antibody.

It was found that astrocytic maturation from engrafted hGPCs was markedly deficient in the HD (GENEA20) hGPC-engrafted brains assessed (n=12 total, across the 3 time points) relative to their control (GENEA19) hGPC-engrafted counterparts (n=10). Focusing on the most rapidly and heavily engrafted white matter compartments of the corpus callosum and internal capsules, it was found that GFAP-defined astrocytic differentiation by HD hGPCs was significantly diminished relative to that of control GPCs and remained so through the 18-week observation point (FIGS. 12A-12F). To validate this observation quantitatively, those brains sacrificed at both 13 weeks and 18 weeks were scored. At 13 weeks, the control hGPC-engrafted mice showed appreciable GFAP+ astrocytic maturation, such that 5.9%±0.5% of human donor cells in the corpus callosum expressed GFAP (n=4 mice; included 170 GFAP$^+$ out of 2,669 total scored donor cells); in contrast, only 3.3%±0.3% of human cells were GFAP+ in mHTT GPC-engrafted callosa (n=5 mice; 60 GFAP+ out of 2,153 scored donor cells) (p=0.026) (FIG. 12I). By 18 weeks, the mHTT-dependent suppression of astrocytic maturation remained pronounced; by that point, 8.5%±1.0% of control-derived cells had developed a GFAP+ astrocytic phenotype (n=3 mice; 209 GFAP+ out of 2,452 scored donor cells), while only 4.9%±0.8% of mHTT-expressing human donor cells did so (n=4 mice; 147 GFAP+ out of 3,522 scored donor cells) (p<0.005) (FIG. 12I). Together, these data indicate that astrocytic differentiation by mHTT-expressing hESC GPCs is significantly delayed relative to normal hESC GPCs (F=16.31 [1.16 degrees of freedom (df)], 2-way ANOVA; p=0.0009 overall). As a result, one might expect that the developmental circuit integration as well as the adult function of astrocytes might be impaired in HD.

Example 8—mHTT GPC White Matter Astrocytes Developed Abnormal Fiber Distributions and Domains In light of the diminished and delayed astrocytic differentiation noted in the mHTT hGPC-engrafted mice, it was next asked whether the morphologies developed by those HD astrocytes that did mature were normal or whether their mature architectures ultimately differed from those of their more rapidly developing control hGPC-derived counterparts. Gross assessment revealed that the mature astrocytic morphologies of mHTT-expressing and control astrocytes differed in that the mHTT-expressing, HD-derived astrocytes typically failed to manifest the degree of radial symmetry of their control-derived counterparts (FIGS. 12G and 12H). To investigate this observation, Sholl analysis was used to assess the complexity of individual astroglial morphologies; Sholl analysis is based on the number of intersections of cellular processes with concentric circles placed at sequentially more distant radii (Sholl, D. A., "Dendritic Organization in the Neurons of the Visual and Motor Cortices of the Cat," *J Anat* 87:387-406 (1953), which is hereby incorporated by reference in its entirety). By imaging anti-human GFAP-immunostained cells in z stacks of 150-mm sections and reconstructing these in Neurolucida (MBF Biosciences), the fiber architectures of donor-derived astrocytes in the white matter of mice engrafted with two different lines of mHTT hESC hGPCs (GENEA18 and GENEA 20) was compared to those engrafted with hGPCs derived from two control hESC lines (C27 iPSCs and GENEA19 hESCs, the latter sibling to GENEA20). Sholl analysis revealed that the fiber complexity of the mHTT-expressing astrocytes was substantially diminished relative to astrocytes derived from their sibling control hGPCs (FIGS. 13A-13D). This effect was particularly evident in the comparison of mHTT astrocytes derived from GENEA20 hESCs to normal astrocytes derived from their matched GENEA19 siblings (FIGS. 12J-12P). The human astrocytes in the mHTT hGPC-engrafted chimeras differed significantly from those in the normal GPC-engrafted mice, with less fiber network complexity (FIG. 12J) and characterized by fewer yet longer processes (FIGS. 12K-12M). When the 3-dimensional Neurolucida tracings (FIGS. 12O and 12P) were additionally assessed by Fan-in radial analysis to assess the extent to which the fiber domain of each cell occupied its immediate volumetric environment (Dang et al., "Formoterol, A Long-Acting Beta2 Adrenergic Agonist, Improves Cognitive Function and Promotes Dendritic Complexity in a Mouse Model of Down syndrome," *Biol Psychiatry* 75:179-188 (2014), which is hereby incorporated by reference in its entirety), it was found that mHTT astrocytes exhibited significantly more regions that were unoccupied by glial processes than did control-derived astrocytes (FIGS. 12N-12P), indicative of a discontiguous and incomplete domain structure.

To better understand the transcriptional concomitants to these HD-associated morphological abnormalities in astrocyte morphology, the gene expression patterns of HD versus control-derived astrocytes were next assessed. To do so, CD140a-defined hGPCs were generated as per the standard protocol and then directed toward astrocytic differentiation by transitioning the cells to serum-containing media supplemented with 20 ng/mL BMP4. The cells were then sorted on the basis of CD44, which among brain cells is differentially expressed by astrocytes and their committed precursor cells (Cai et al., "CD44-Positive Cells are Candidates for Astrocyte Precursor Cells in Developing Mouse Cerebellum," *Cerebellum* 11:181-193 (2012); Liu et al., "Chromatin Landscape Defined by Repressive Histone Methylation During Oligodendrocyte Differentiation," *J Neurosci* 35:352-365 (2015), which are hereby incorporated by reference in their entirety). RNA-seq was then performed on the extracted RNA of HD and control-derived CD44-defined astrocytes, which were confirmed as such by their virtually uniform expression of GFAP. This analysis revealed significant differences in gene expression by mHTT-expressing astroglia relative to control-derived CD44+ astroglia (FIGS. 14A-14C). Network analysis revealed the differential expression of four discrete modules, which included functional ontologies referable to (1) synaptic, post-synaptic, and receptor-associated genes; (2) endosomal transcripts; (3) desmosomal and cell-cell junction genes; and extracellular matrix components (FIGS. 14D-14H). Of these, the largest set of differentially expressed genes were those referable to synaptic and receptor modulation; these included a number of genes that regulate fiber outgrowth and motility, including MYL7 and MYLK2, the myosin light chain-7, and myosin light chain kinase-2, which were both sharply downregulated in mHTT-expressing astrocytes relative to controls (FIG. 14E). Importantly, the glial myosins and their kinases are involved not only in glial fiber elaboration but also in astroglial calcium signaling (Cotrina et al., "Cytoskeletal Assembly and ATP Release Regulate Astrocytic Calcium Signaling," *J. Neurosco.* 18:8794-8804 (1998), which is hereby incorporated by reference in its entirety). Their deficient expression in HD astroglia might then contribute to the abnormal morphological development of HD astrocytes (Khakh et al., "Unravelling and Exploiting Astrocyte Dysfunction in Huntington's Disease," *Trends Neurosci.* 40:422-437 (2017); Octeau et al., "An Optical Neuron-Astrocyte Proximity Assay at Synaptic Distance Scales," *Neuron* 98:49-66 (2018), which are hereby incorporated by reference in their entirety) while predicting aberrant signaling within the glial syncytium of the HD brain (Jiang et al., "Dysfunctional Calcium and Glutamate Signaling in Striatal Astrocytes from Huntington's Disease Model Mice," *J. Neurosci.* 36:3453-3470 (2016), which is hereby incorporated by reference in its entirety). Together, these data serve to emphasize that HD is associated with deficient astrocytic differentiation and functional development, as well as with impaired oligodendrocytic maturation and myelination.

Discussion of Examples

These experiments suggest that white matter failure in HD is a product of an mHTT-dependent block in differentiation by affected hGPCs, such that mRNAs encoding a group of critical glial lineage transcription factors are differentially downregulated in mHTT-expressing hGPCs. The mHTT-associated inhibition of oligodendroglial differentiation in particular, as manifested by the downregulated expression of NKX2.2, OLIG2, and SOX10, is accompanied by the diminished expression of the SOX10-regulated myelin regulatory factor MYRF. This results in the suppression of myelination, which requires the MYRF-dependent transcription of critical mRNAs associated with myelin biogenesis, such as MAG and MBP (Bujalka et al., "MYRF is a Membrane-Associated Transcription Factor that Autoproteolytically Cleaves to Directly Activate Myelin Genes," *PLoS Biology* 11:e1001625 (2013); Emery et al., "Myelin Gene Regulatory Factor is a Critical Transcriptional Regulator Required for CNS Myelination," *Cell* 138:172-185 (2009), which are hereby incorporated by reference in their entirety). Interestingly, the downregulation of MYRF has been similarly noted in the mature oligodendrocytes of HD transgenic mice expressing especially long CAG repeats (150Q and 250Q) (Jin et al., "Early White Matter Abnormalities, Progressive Brain Pathology and Motor Deficits in a Novel Knock-in Mouse Model of Huntington's Disease," *Hum. Mol. Genet.* 24:2508-2527 (2015), which is hereby incorporated by reference in its entirety). These data reveal that in humans, the mHTT-associated block in glial differentiation occurs at an earlier stage than previously appreciated and is apparent in bipotential hGPCs that generate astrocytes as well as oligodendrocytes. As such, it was found that mHTT significantly impedes the development of both glial lineages in HD and, importantly, that this developmental arrest occurs in human GPCs expressing CAG repeat expansion lengths of 40-48Q, which typify human HD.

These expression data implicating the mHTT-dependent suppression of NKX2.2, OLIG2, and SOX10 in the white matter deficiency of HD suggested that efforts to overexpress or otherwise activate the transcription of SOX10 and MYRF might be sufficient to relieve the myelination defect of this disease. This was found to be the case, in that forced expression of SOX10 and MYRF in mHTT-expressing hGPCs rescued the expression of critical genes involved in myelin biogenesis and restored myelination by HD-derived glia in vivo. As such, the targeted activation or upregulation of SOX10 and MYRF might serve as a means of restoring the myelination competence of mHTT-expressing oligodendrocytes in HD.

Besides the defects in oligodendrocyte maturation and myelination associated with mHTT, it was noted that astrocytic differentiation was also impaired, as might have been expected given the dysregulation of glial transcription as early as the NKX2.2 and OLIG2 stages, proximal to the astrocyte-oligodendrocyte fate choice. Such defective astrocytic maturation of HD hGPCs suggests that the HD phenotype might have a significant developmental component, in that any delay in astrocytic differentiation by mHTT-expressing hGPCs might impair developmental synaptogenesis and circuit formation, each of which depend upon astrocytic guidance (Clarke et al., "Glia Keep Synapse Distribution Under Wraps," *Cell* 154:267-268 (2013); Ullian et al., "Control of Synapse Number by Glia," *Science* (New York, NY) 291:657-661 (2001), which are hereby incorporated by reference in their entirety). In addition, any such disease-dependent delay in astrocytic maturation might be expected to contribute to the delayed (and ultimately deficient myelination of HD, given the metabolic dependence of oligodendrocytes upon local astrocytes (Amaral et al., "Metabolic aspects of neuron-oligodendrocyte-astrocyte interactions," *Front Endocrinol (Lausanne)* 4:54 (2013), which is hereby incorporated by reference in its entirety). It remains to be seen whether the rescue of astrocytic maturation by HD-derived hGPCs might relieve these effects on synaptic development and organization; if so, one may predict that astrocytic replacement might be sufficient to rescue the synaptic pathology of HD in a manner in which the rescue of oligodendrocytic differentiation appears sufficient to relieve the myelination defect of HD.

Besides their contributions to neural network formation and synaptic architecture, both hGPCs and astrocytes are intimately involved both in maintaining adult interstitial ion homeostasis and in the regulation of neuronal excitability. It was thus intriguing to note that the arrested terminal differentiation of mHTT-expressing hGPCs was associated with the widespread suppression of several families of glial potassium channels. These included the inwardly rectifying $K^+$ channels of the KCNJ family, including KCNJ8 and KCNJ9, among others. This mHTT-associated suppression of inwardly rectifying $K^+$ channels, which are responsible for potassium import into cells, might contribute to the hyper-excitability of HD neurons by inhibiting the glial reuptake of synaptically released $K^+$ (Shin et al., "Expression of Mutant Huntingtin in Glial Cells Contributes to Neuronal Excitotoxicity," *J Cell Biol* 171:1001-1012 (2005), which is hereby incorporated by reference in its entirety). In that regard, Khakh and colleagues have reported a deficit in astrocytic expression of the inwardly rectifying channel Kir4.1 (KCNJ10) in mouse models of HD (Tong et al., "Astrocyte Kir4.1 Ion Channel Deficits Contribute to Neuronal Dysfunction in Huntington's Disease Model Mice," *Nat Neurosci* 17:694-703 (2014), which is hereby incorporated by reference in its entirety), which might similarly reflect the effect of disrupted glial maturation on potassium channel expression and glial $K^+$ uptake. In mHTT-expressing human GPCs, arrested at a stage before terminal astrocytic maturation, it appears that a large set of $K^+$ channel transcripts are coordinately suppressed, suggesting the inhibition of a shared upstream activator of $K^+$ channel gene expression. While the upstream regulators of these potassium channel genes have not yet been identified, it is reasonable to posit that the mHTT-dependent suppression of terminal glial differentiation might lead to a failure in the development of glial potassium homeostatic mechanisms that would otherwise regulate and protect neuronal activity.

Together, these observations suggest that any disruption in astrocytic maturation by HD hGPCs might be expected to significantly influence both the development and adult performance of neural networks in HD. Importantly, a corollary of these findings is that the replacement of mHTT-expressing hGPCs by their wild-type or genetically corrected counterparts might be sufficient to restore functional astrocytes and oligodendroglia to affected HD brain. This possibility was first suggested by the ability of neonatally delivered wild-type hGPCs to outcompete diseased hGPCs in models of congenital hypo-myelination (Windrem et al., "Neonatal Chimerization with Human Glial Progenitor Cells can Both Remyelinate and Rescue the Otherwise Lethally Hypomyelinated Shiverer Mouse," *Cell Stem Cell* 2:553-565 (2008), which is hereby incorporated by reference in its entirety), and it has similarly been noted that neonatal glial replacement is sufficient to correct deficient potassium homeostasis in HD transgenic mice as well (Benraiss et al., "Human Glia can Both Induce and Rescue Aspects of Phenotype in Huntington Disease. *Nature Communications* 7:11758 (2016), which is hereby incorporated by reference in its entirety). Whether such competitive dominance of healthy over diseased cells may occur in adult HD remains to be established, but should this prove feasible, such a strategy of glial replacement might prove a realistic therapeutic avenue for disease amelioration in HD.

It will be appreciated that variants of the above-disclosed and other features and functions, or alternatives thereof, may be combined into many other different systems or applications. Various presently unforeseen or unanticipated alternatives, modifications, variations, or improvements therein may be subsequently made by those skilled in the art which are also intended to be encompassed by the following claims.

What is claimed:

1. A method of treating or inhibiting onset of Huntington's disease, said method comprising:
   selecting a subject having or at risk of having hypomyelination; and
   administering to the selected subject one or more modulators of a gene or protein encoded thereof involved in the NKX2.2→OLIG2→SOX10→MYRF regulatory cascade, wherein the method results in an increase in myelination in the subject.

2. The method of claim 1, wherein the gene or protein encoded therefrom is selected from the group consisting of a SOX10 gene or protein encoded therefrom, a MYRF gene or protein encoded therefore, an OLIG2 gene or protein encoded therefrom, a TCF7L2 gene or protein encoded therefrom, and a NKX2.2 gene or protein encoded therefrom, or any combination thereof.

3. The method of claim 1, wherein said administering is carried out using intracerebral delivery, intrathecal delivery, intranasal delivery, or via direct infusion into brain ventricles.

4. The method of claim 1, further comprising:
   administering to the selected subject a preparation of human glial progenitor cells.

5. The method of claim 4, wherein the preparation of glial progenitor cells are astrocyte-biased glial progenitor cells.

6. The method of claim 4, wherein glial progenitor cells of the preparation are A2B5$^+$, CD140a$^+$, and/or CD44$^+$.

7. The method of claim 4, wherein said preparation of glial progenitor cells is administered to the striatum, forebrain, brain stem, and/or cerebellum of the subject.

8. The method of claim 1, wherein the subject is human.

9. The method of claim 1, wherein the modulator upregulates expression of said gene or protein encoded therefrom.

10. The method of claim 1, wherein the modulator is selected from the group consisting of:
   a) a nucleic acid molecule;
   b) a peptide; and
   c) a small molecule.

11. The method of claim 10, wherein the modulator is a nucleic acid molecule comprising a nucleotide sequence encoding a protein involved in the NKX2.2→OLIG2→SOX10→MYRF regulatory cascade.

12. The method of claim 11, wherein said protein encoded by the nucleic acid molecule is selected from the group consisting of:
   a) a SOX10 protein;
   b) a MYRF protein; and
   c) any combination thereof.

13. The method of claim 11, wherein the nucleic acid molecule comprises an expression vector.

14. The method of claim 13, wherein the expression vector is a viral vector selected from the group consisting of an adenovirus vector, adeno-associated virus vector, retrovirus vector, lentivirus vector, and herpes virus vector.

15. The method of claim 13, wherein the expression vector is a plasmid.

16. The method of claim 11, wherein the nucleotide sequence encoding the protein is operably linked to a promoter.

17. The method of claim 16, wherein the promoter is an inducible promoter.

18. The method of claim 4, wherein the human glial progenitor cells are genetically modified to express a gene or protein encoded thereof that is involved in the NKX2.2→OLIG2→SOX10→MYRF regulatory cascade.

19. The method of claim 17, wherein the gene or protein encoded thereof is selected from the group consisting of:
   a) a SOX10 gene or protein encoded therefrom;
   b) a MYRF gene or protein encoded therefrom; and
   c) any combination thereof.

* * * * *

SEQUENCE LISTING

```
<160> NUMBER OF SEQ ID NOS: 28

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
accttcgctt tcatctccaa c                                          21

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
cgatgatgag ggtcttgatg tc                                         22

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
ggaccctatt ctcaccatct tc                                         22

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
cacaccagta ctctccatca tc                                         22

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
cggagttgtg cacgtagtag                                            20

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
```

```
atcttcacac agaaagggac ag                                          22

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
cgaatcacga ggtcaggagt                                             20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
gcccaccact atgctcagtt                                             20

<210> SEQ ID NO 9
<211> LENGTH: 21
<212> TYPE: DNA
<213> ORGANISM: Artificial Sequence
<220> FEATURE:
<223> OTHER INFORMATION: Primer

<400> SEQUENCE: 9
acactggatg caatggtgtt a                                           21

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
cagcaactcc agtgtgaaga                                             20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
catcctgtcc ttccgtgaat                                             20

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
gaagtggaag tggtagtctg tg                                          22

<210> SEQ ID NO 13
<211> LENGTH: 23
<212> TYPE: DNA
```

```
<213> ORGANISM: Artificial Sequence
<220> FEATURE:
<223> OTHER INFORMATION: Primer

<400> SEQUENCE: 13
tttatggcca tgtaaacgtt ctg                                              23

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
gcaacaatca ccaccgatat t                                                21

<210> SEQ ID NO 15
<211> LENGTH: 17
<212> TYPE: DNA
<213> ORGANISM: Artificial Sequence
<220> FEATURE:
<223> OTHER INFORMATION: Primer

<400> SEQUENCE: 15
gtgggagact ccgggta                                                     17

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16
tgagattgga tatgaccatc agc                                              23

<210> SEQ ID NO 17
<211> LENGTH: 23
<212> TYPE: DNA
<213> ORGANISM: Artificial Sequence
<220> FEATURE:
<223> OTHER INFORMATION: Primer

<400> SEQUENCE: 17
gagggaagag acaaccacaa atg                                              23

<210> SEQ ID NO 18
<211> LENGTH: 24
<212> TYPE: DNA
<213> ORGANISM: Artificial Sequence
<220> FEATURE:
<223> OTHER INFORMATION: Primer

<400> SEQUENCE: 18
gaccacaaca ttgagcaata agag                                             24

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
gaggaggact tggttgatgt t                                                21
```

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
tgagatgcta ctgaggcatt g                                              21

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
gtggctccaa ccttctgtcc                                                20

<210> SEQ ID NO 22
<211> LENGTH: 19
<212> TYPE: DNA
<213> ORGANISM: Artificial Sequence
<220> FEATURE:
<223> OTHER INFORMATION: Primer

<400> SEQUENCE: 22
gcagggaaac cagtgtagc                                                 19

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
ccagtttgac tactctgacc a                                              21

<210> SEQ ID NO 24
<211> LENGTH: 22
<212> TYPE: DNA
<213> ORGANISM: Artificial Sequence
<220> FEATURE:
<223> OTHER INFORMATION: Primer

<400> SEQUENCE: 24
tataggagaa ggccgagtag ag                                             22

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
aggaatgacc ctctatccca                                                20

<210> SEQ ID NO 26
<211> LENGTH: 21
<212> TYPE: DNA
<213> ORGANISM: Artificial Sequence
<220> FEATURE:

```
<223> OTHER INFORMATION: Primer

<400> SEQUENCE: 26
gcatgtcaga ccctcactat c                                               21

<210> SEQ ID NO 27
<211> LENGTH: 22
<212> TYPE: DNA
<213> ORGANISM: Artificial Sequence
<220> FEATURE:
<223> OTHER INFORMATION: Primer

<400> SEQUENCE: 27
tgtggtcaca cggaaagata ag                                              22

<210> SEQ ID NO 28
<211> LENGTH: 24
<212> TYPE: DNA
<213> ORGANISM: Artificial Sequence
<220> FEATURE:
<223> OTHER INFORMATION: Primer

<400> SEQUENCE: 28
gtcagttacg ttgcttccaa atag                                            24
```